(12) United States Patent
Balocchi et al.

(10) Patent No.: US 9,057,716 B2
(45) Date of Patent: Jun. 16, 2015

(54) BACTERICIDAL ANTIBODY ASSAYS TO ASSESS IMMUNOGENICITY AND POTENCY OF MENINGOCOCCAL CAPSULAR SACCHARIDE VACCINES

(75) Inventors: Cristiana Balocchi, Siena (IT); Enrico Luzzi, Siena (IT); Marilena Paludi, Siena (IT); Marzia Monica Giuliani, Siena (IT); John Donnelly, Moraga, CA (US); Elena Mori, Siena (IT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/820,481

(22) PCT Filed: Sep. 2, 2011

(86) PCT No.: PCT/US2011/050436
§ 371 (c)(1),
(2), (4) Date: Apr. 16, 2013

(87) PCT Pub. No.: WO2012/031271
PCT Pub. Date: Mar. 8, 2012

(65) Prior Publication Data
US 2013/0196352 A1    Aug. 1, 2013

Related U.S. Application Data

(60) Provisional application No. 61/380,220, filed on Sep. 4, 2010.

(51) Int. Cl.
| | |
|---|---|
| G01N 33/569 | (2006.01) |
| G01N 33/53 | (2006.01) |
| G01N 33/15 | (2006.01) |
| A61K 39/095 | (2006.01) |
| A61K 39/00 | (2006.01) |

(52) U.S. Cl.
CPC .............. *G01N 33/15* (2013.01); *A61K 39/095* (2013.01); *G01N 33/56911* (2013.01); *G01N 2333/22* (2013.01); *A61K 2039/6037* (2013.01); *A61K 2039/6068* (2013.01)

(58) Field of Classification Search
CPC .................... G01N 2333/22; G01N 33/56911; G01N 2469/20
USPC ................... 435/7.32, 32, 330, 340, 810, 975
See application file for complete search history.

(56) References Cited

U.S. PATENT DOCUMENTS

2003/0068336 A1* 4/2003 Ryall ......................... 424/250.1

FOREIGN PATENT DOCUMENTS

| WO | WO-00/77518 A2 | 12/2000 |
|---|---|---|
| WO | WO-01/40473 A2 | 6/2001 |
| WO | WO-03/069342 A1 | 8/2003 |
| WO | WO-2005/032583 A2 | 4/2005 |
| WO | 2006/034320 A2 | 3/2006 |
| WO | WO 2006/034320 * | 3/2006 |
| WO | WO-2007/054820 | 5/2007 |

OTHER PUBLICATIONS

Joseph et al (Clinical and Diagnostic Laboratory Immunology, Jan. 2004, vol. 11, No. 1, p. 1-5).*
Frasch, C. et al. (Jun. 2009) "Bactericidal Antibody is the Immunologic Surrogate of Protection Against Meningococcal Disease," Vaccine 27( Suppl 2):B112-B116.
Giuliani, M. et al. (Jul. 2006) "A Universal Vaccine for Serogroup B Meningococcus," Proceedings of the National Academy of Sciences of USA 103(29):10834-10839.
Granoff, D. (Dec. 2001) "Assessing Efficacy of Haemophilus Influenzae Type B Combination Vaccines," Clinical Infectious Diseases: An Official Publication of the Infectious Diseases Society of America 33(Suppl 4):S278-S287.
Granoff, D. and Harris, S. (Jun. 2004) "Protective Activity of Group C Anticapsular Antibodies Elicited in Two-year-olds by an Investigational Quadrivalent *Neisseria Meningitidis*-Diphtheria Toxoid Conjugate Vaccine," The Pediatric Infectious Disease Journal 23(6):490-497.
Hou et al. (2005) "Protective antibody responses elicited by a meningococcal outer membrane vesicle vaccine with overexpressed genome-derived neisserial antigen 1870," J. Inf. Disease 192:580-590.
Jodar, L. et al. (Jul. 2003) "Serological Criteria for Evaluation and Licensure of New Pneumococcal Conjugate Vaccine Formulations for Use in Infants," Vaccine 21(23):3265-3272.
Li, S. et al. (Apr. 2002) "Inverse Relationship Between Six Week Postvaccination Varicella Antibody Response to Vaccine and Likelihood of Long Term Breakthrough Infection," The Pediatrician Infectious Disease Journal 21(4):337-342.
Masignani et al. (2003) "Vaccination against *Neisseria meningitidis* using three variants of the lipoprotein GNA1870," J. Exp. Med. 197(6):789-799.
Miura, K. et al. (Aug. 2007) "Transmission-Blocking Activity Induced by Malaria Vaccine Candidates Pfs25/Pvs25 is a Direct and Predictable Function of Antibody Titer," Malaria Journal 6(1):107.
Qin, L. et al. (Nov. 2007) "A Framework for Assessing Immunological Correlates of Protection in Vaccine Trials," The Journal of Infectious Diseases 196(9):1304-1312.
Shin, S. et al. (Dec. 2005) "A Predictive Model for the Level of sIgA Based on IgG Levels Following the Oral Administration of Antigens Expressed in *Saccharomyces Cerevisiae*," Journal of Veterinary Science 6(4):305-309.
Spellberg, B. et al. (Apr. 2008) "Antibody Titer Threshold Predicts Anti-Candidal Vaccine Efficacy Even Though the Mechanism of Protection is Induction of Cell-Mediated Immunity," The Journal of Infectious Diseases 197(7):967-971.
Strady, C. et al. (Jun. 2000) "Predictive Factors for the Neutralizing Antibody Response Following Pre-exposure Rabies Immunization: Validation of a New Booster Dose Strategy," Vaccine 18(24):2661-2667.

(Continued)

*Primary Examiner* — Padma V Baskar
(74) *Attorney, Agent, or Firm* — Lisa M. Matovcik

(57) ABSTRACT

The disclosure provides compositions, methods and kits for assessing immunogenicity, potency, or both, of meningococcal capsular saccharide vaccines. The assessment is based upon measurement of binding of a bactericidal antibody to a capsular saccharide component in the vaccine.

22 Claims, 32 Drawing Sheets

(56) References Cited

OTHER PUBLICATIONS

Wu, J. et al. (Jun. 1999) "Hepetitis B Vaccination in High-Risk Infants: 10-year Follow-up," The Journal of Infectious Diseases 179(6):1319-1325.

Zelnik, V. et al. (Mar. 2004) "An Enzyme-linked Immunosorbent Assay (ELISA) for Detection of Marek's Disease Virus-Specific Antibodies and its Application in an Experimental Vaccine Trial," Journal of Veterinary Medicine. B, Infectious Diseases and Veterinary Public Health 51(2):61-67.

Moe, Gregory R., et al., "Sequential Immunization with Vesicles Prepared from Heterologous *Neisseria meningitidis* Strains Elicits Broadly Protective Serum Antibodies to Group B Strains," Infect. Immun., 70(11): 6021-6031 (2002).

Tsang, R.S.W., et al., "Serological Specificities of Murine Hybridoma Monoclonal Antibodies against *Neisseria meningitidis* Serogroups B, C, Y, and W135 and Evaluation of Their Usefulness as Serogrouping Reagents by Indirect Whole-Cell Enzyme-Linked Immunosorbent Assay," Clin. Diag. Lab. Immunol. 12(1): 152-156 (2005).

Chatterjee et al. (2010). "The immunogenicity and safety of a reduced PRP-content DTPw-HBV/Hib vaccine when administered according to the accelerated EPI schedule," BMC Infect Dis, 10:298.

Donnelly et al. (2010). "Qualitative and quantitative assessment of meningococcal antigens to evaluate the potential strain coverage of protein-based vaccines," PNAS 107(45):1949019495.

Drow et al. (1979). "Indirect sandwich enzyme-linked immunosorbent assay for rapid detection of Haemophilus influenzae type b infection," J Clin Microbiol, 10(4):442-50.

Findlow et al. (2006). "Comparison and correlation of neisseria meningitidis serogroup B immunologic assay results and human antibody responses following three doses of the Norwegian meningococcal outer membrane vesicle vaccine MenBvac," Infect Immun, 74(8):4557-65.

Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.

Poirier et al. (2000). "In vitro potency assay for hepatitis A vaccines: development of a unique economical test," Biologicals, 28(4):247-56.

Rosenqvist et al. (1990). "Serogroup determination of Neisseria meningitidis by whole-cell ELISA, dot-blotting and agglutination," APMIS: acta pathologica, microbiologica, et immunologica Scandinavica 98(6):501-506.

Sarafian et al. (1982). "Detection of gonococcal antigens by an indirect sandwich enzyme-linked immunosorbent assay," J Med Microbiol, 15(4):541-50.

Sippel et al. (1984). "Detection of Neisseria meningitidis group A, Haemophilus influenzae type b, and Streptococcus pneumoniae antigens in cerebrospinal fluid specimens by antigen capture enzyme-linked immunosorbent assays," J Clin Microbiol, 20(2):259-65.

Sugasawara et al. (1984). "Enzyme-linked immunosorbent assay with a monoclonal antibody for detecting group A meningococcal antigens in cerebrospinal fluid," J Clin Microbiol. 19(2):230-4.

Yero et al. (2007). "Identification by genomic immunization of a pool of DNA vaccine candidates that confer protective immunity in mice against Neisseria meningitidis serogroup B," Vaccine, 25(28):5175-88.

* cited by examiner

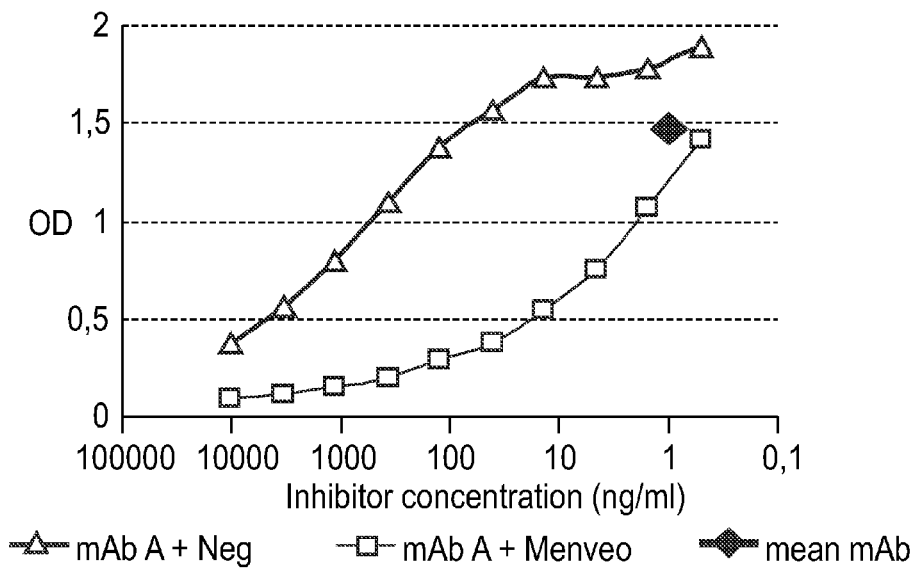
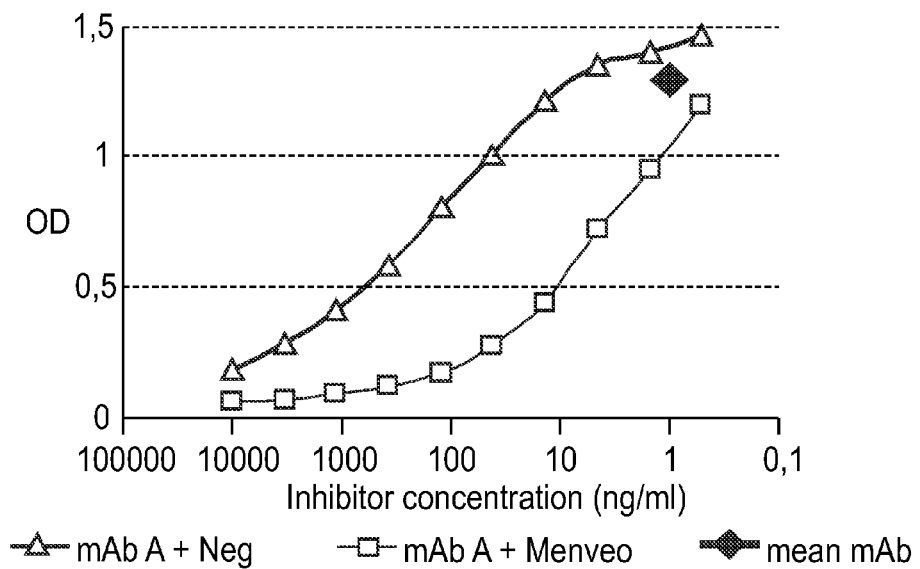

FIG. 1C mAb anti-C inhibition with oligo C and Menveo coating PS

△ mAb C + Neg    □ mAb C + Menveo    ◆ mean mAb

FIG. 1D mAb anti-C inhibition with oligo C and Menveo coating CONJ

△ mAb C + Neg    □ mAb C + Menveo    ◆ mean mAb

FIG. 1E
mAb anti-W inhibition with oligo W and Menveo coating PS

△ mAb W + Neg   □ mAb W + Menveo   ◆ mean mAb

FIG. 1F
mAb anti-W inhibition with oligo W and Menveo coating CONJ

△ mAb W + Neg   □ mAb W + Menveo   ◆ mean mAb mAb anti-Y inhibition with oligo Y and Menveo coating PS mAb

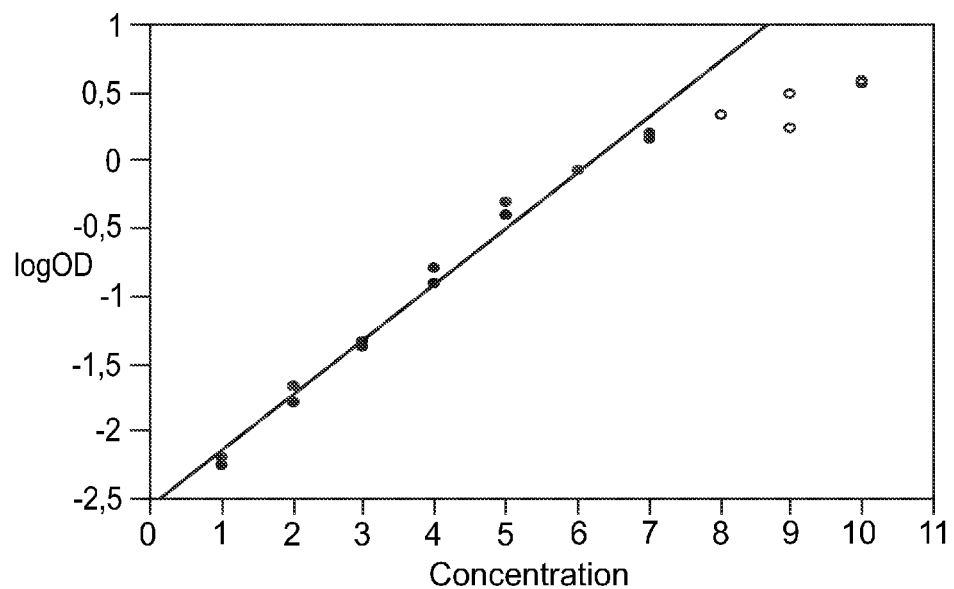
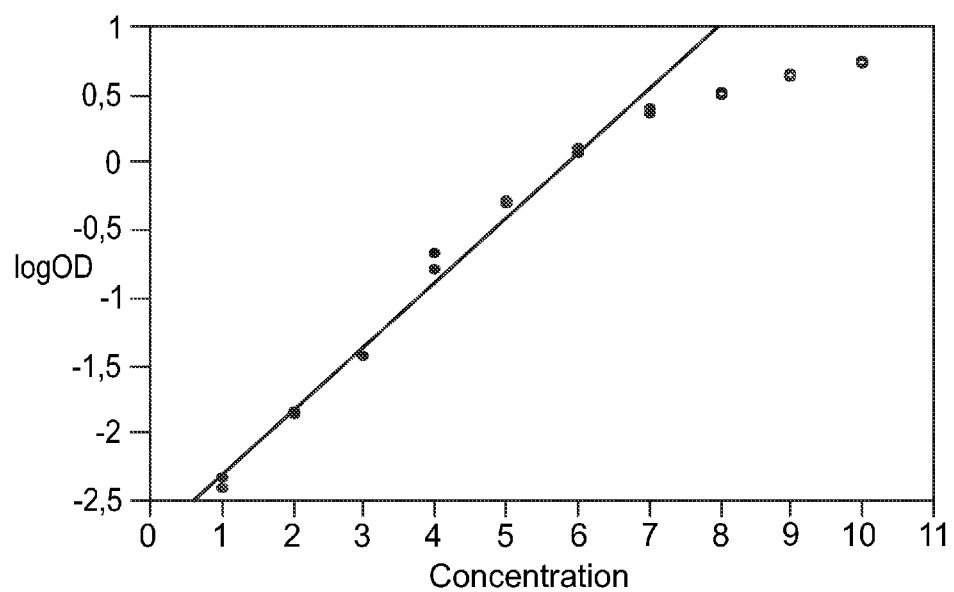

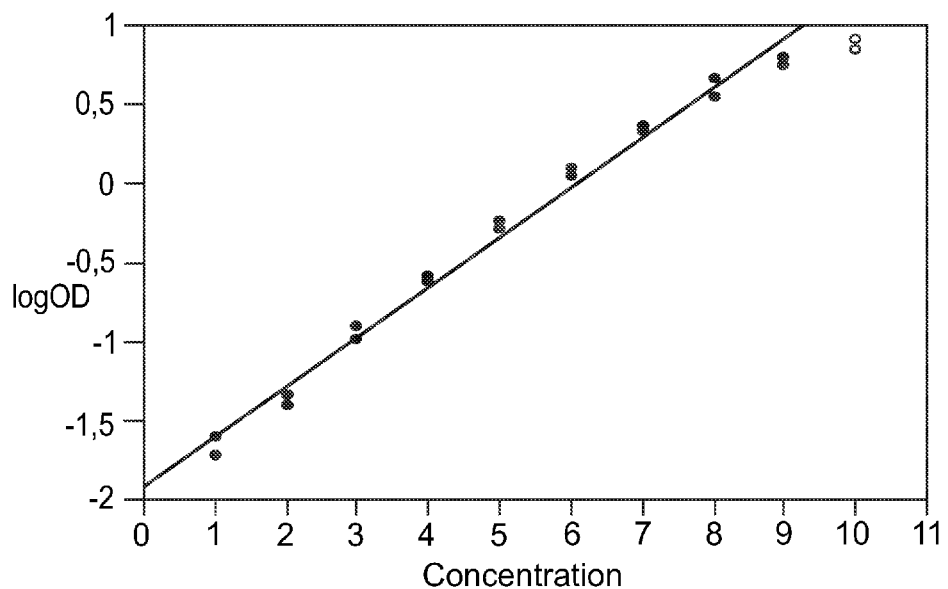
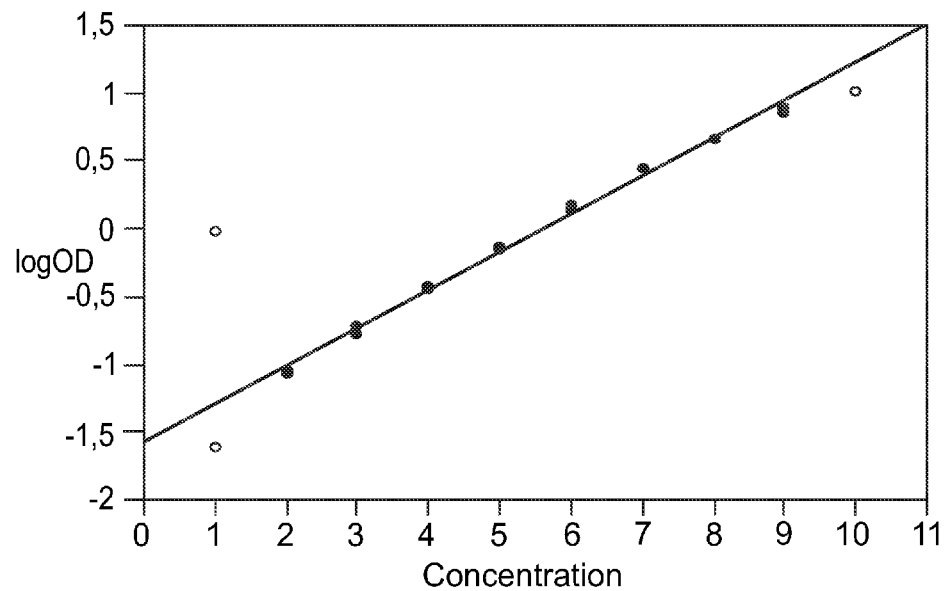

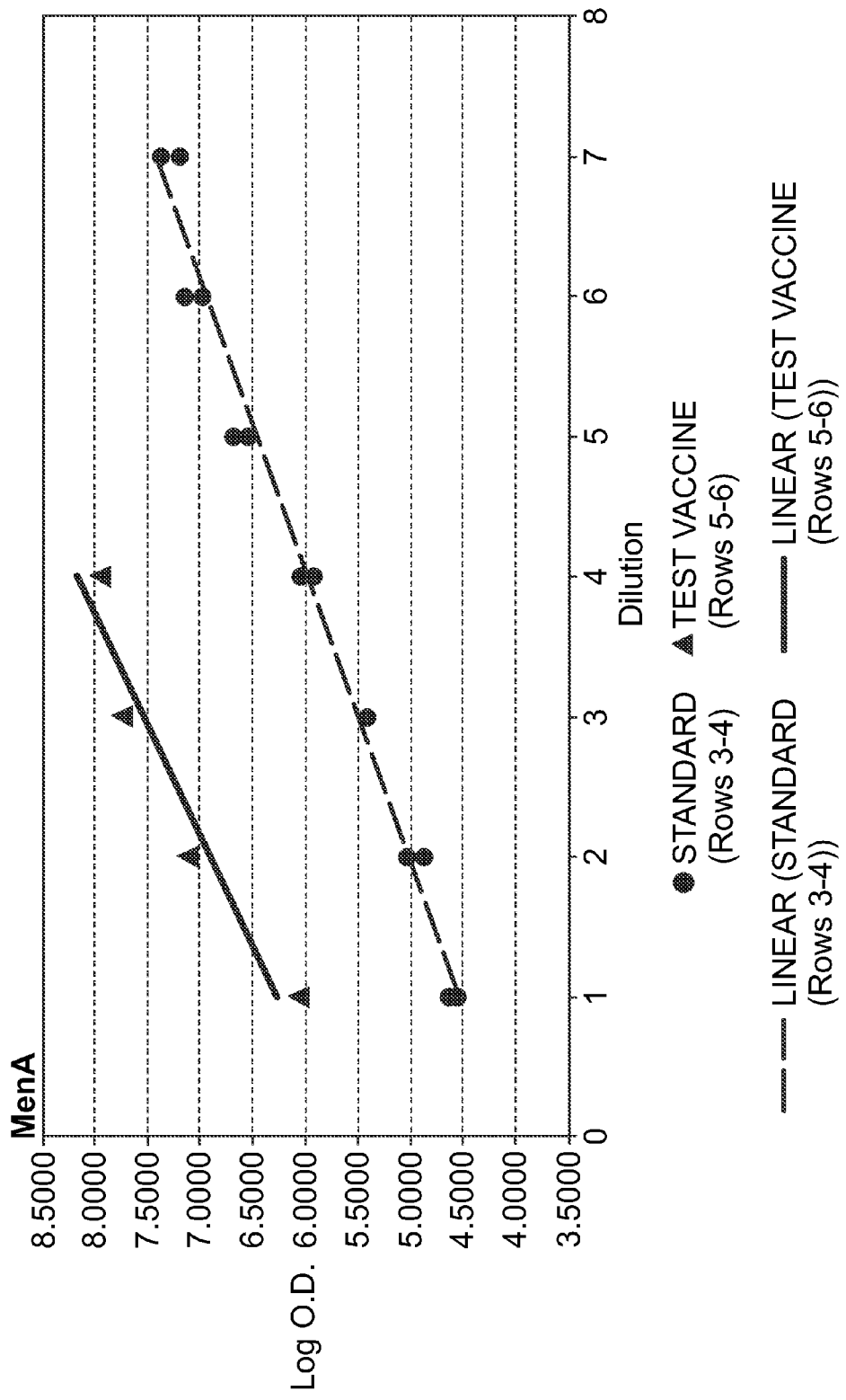

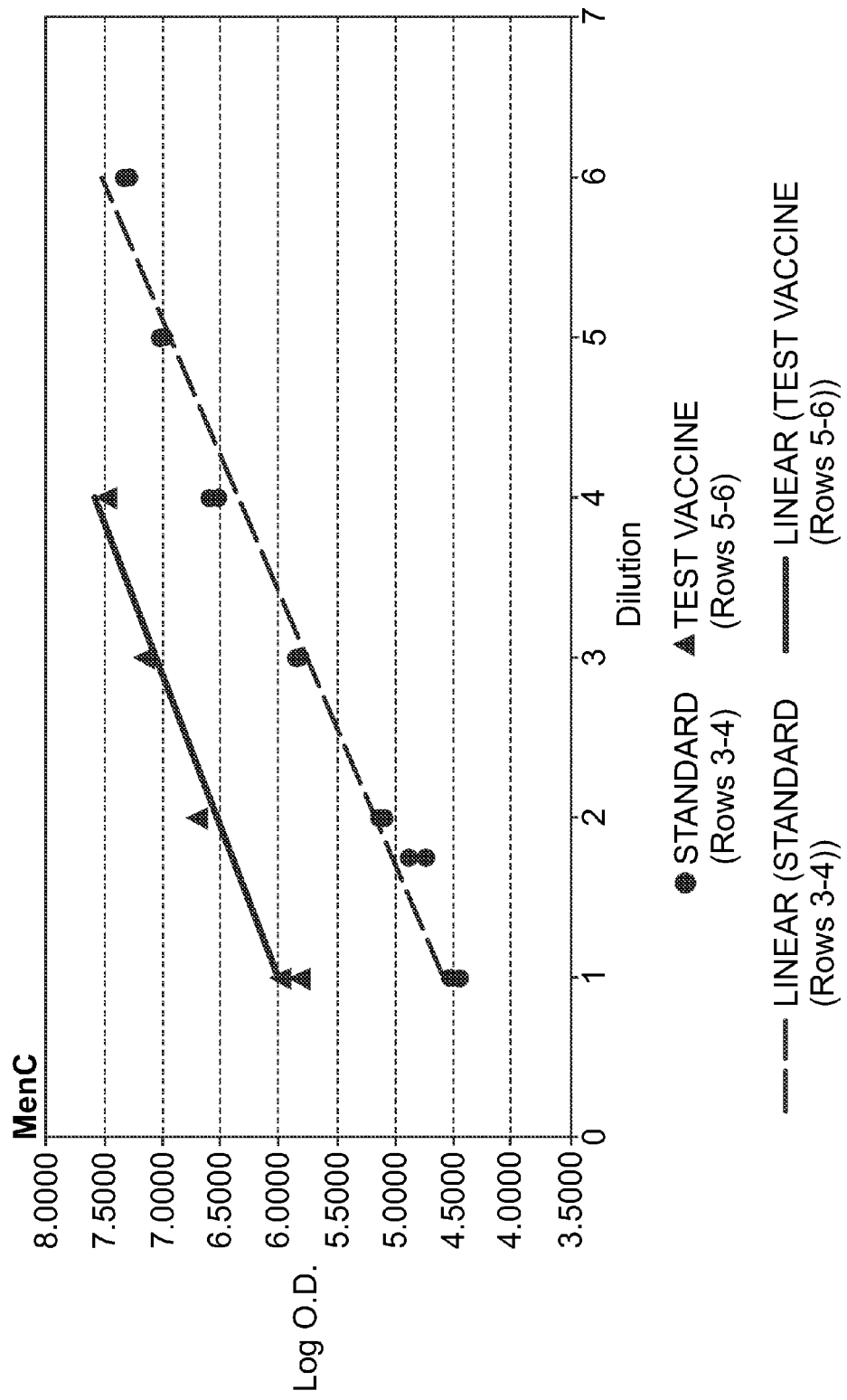

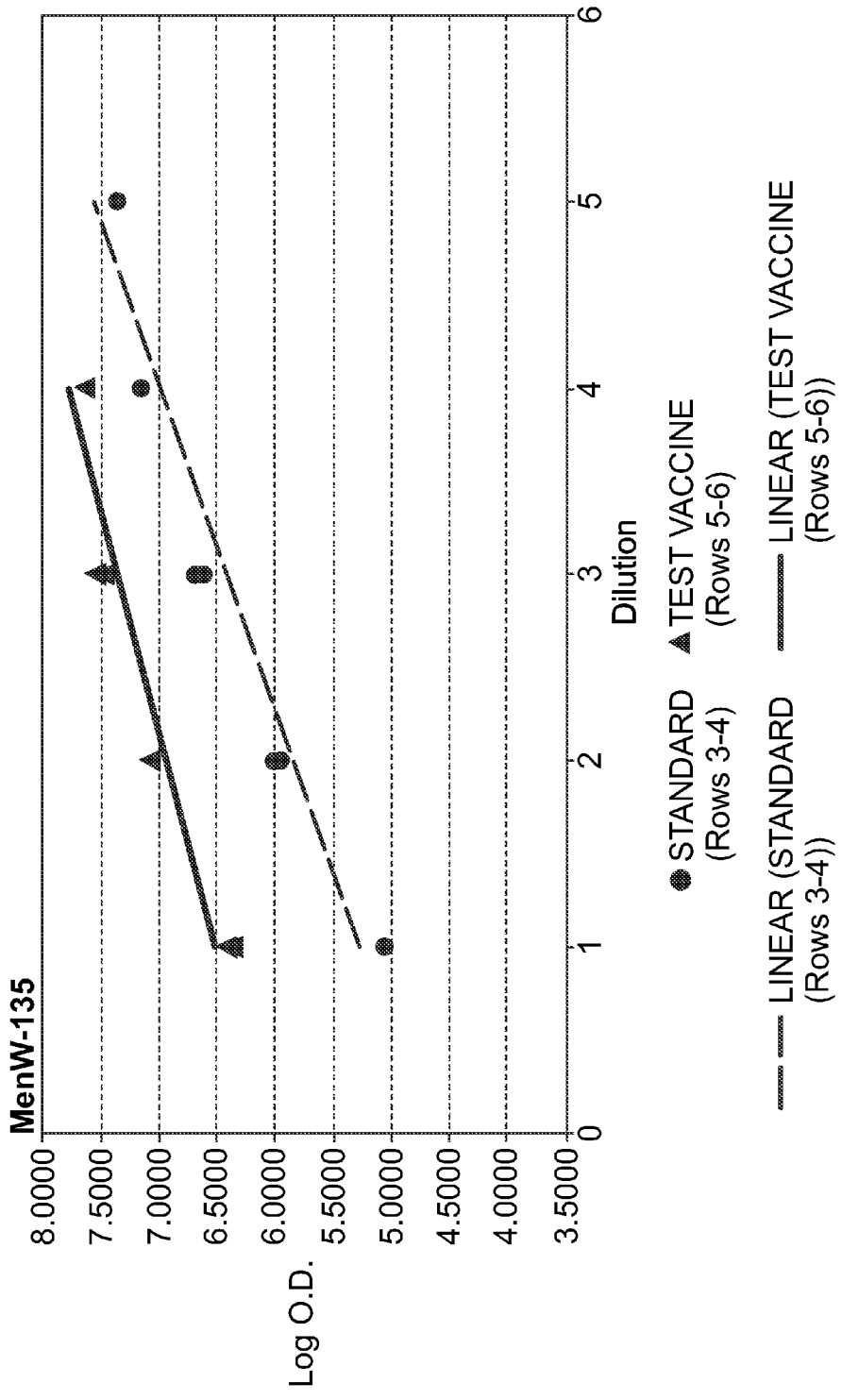

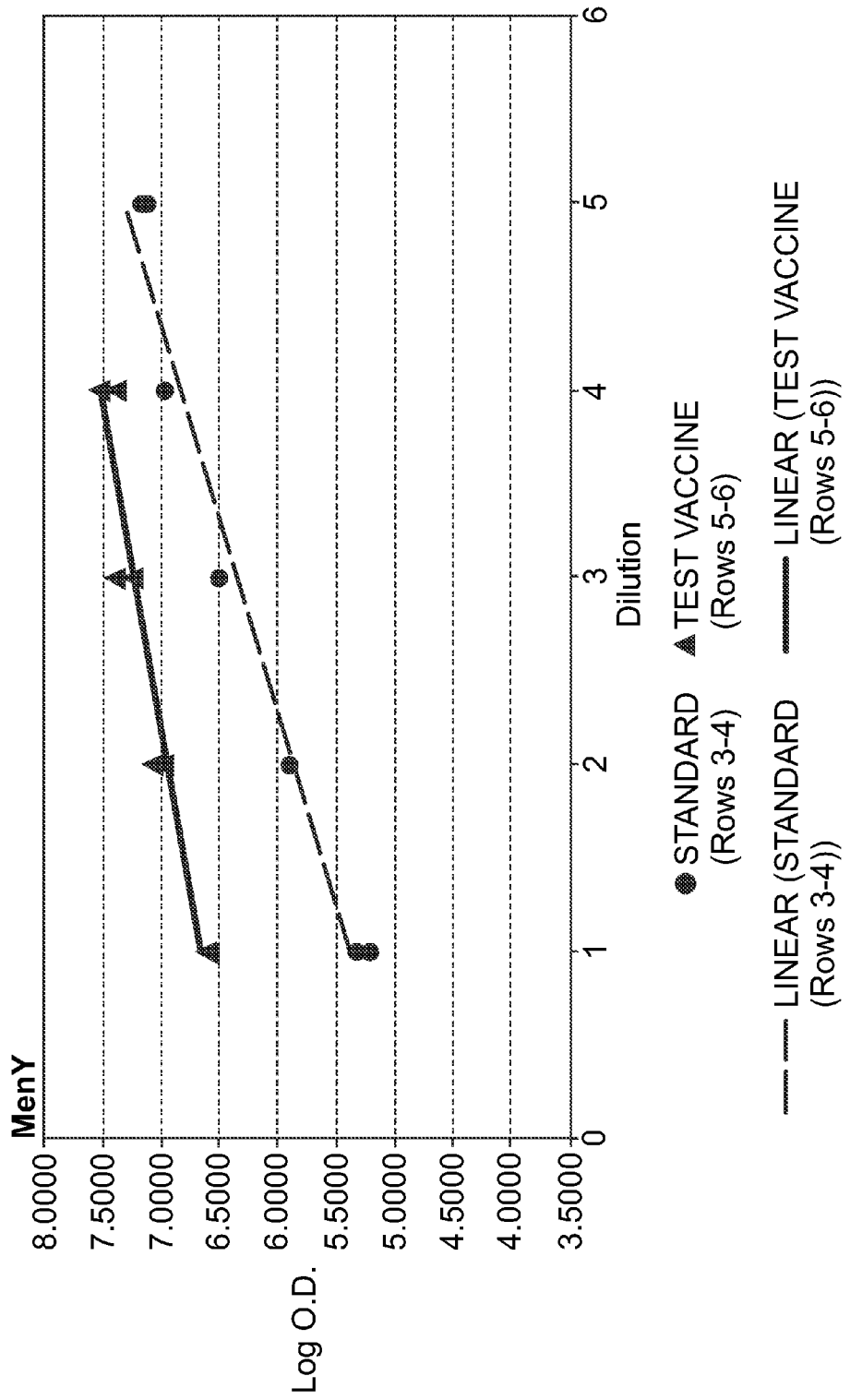

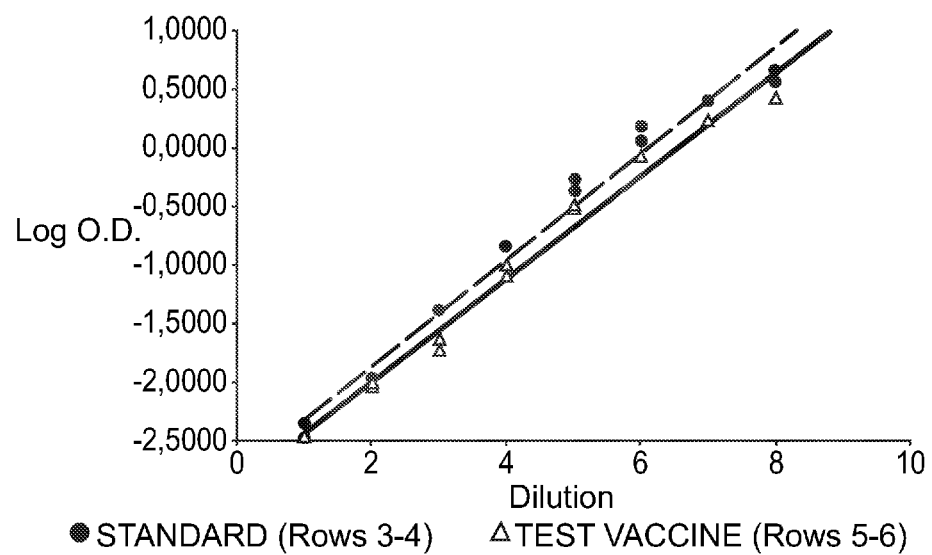
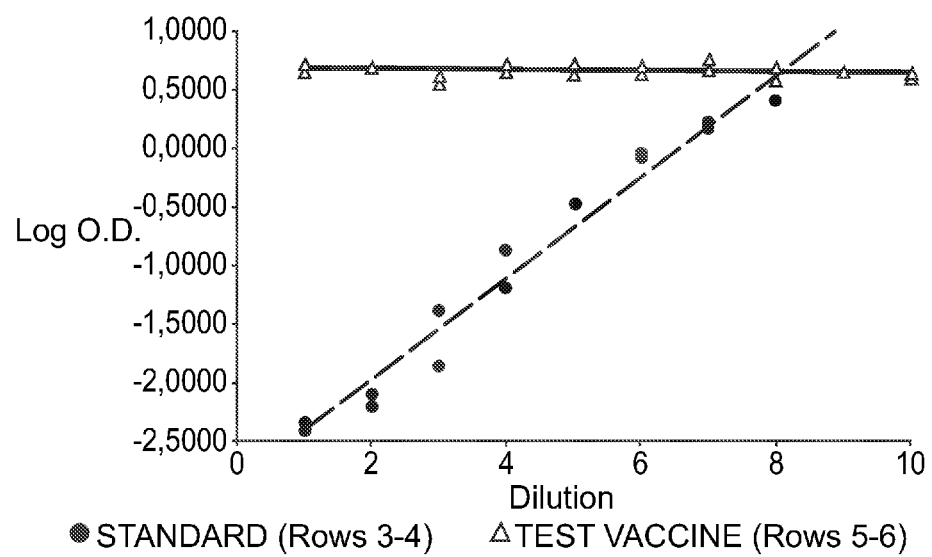

BACTERICIDAL ANTIBODY ASSAYS TO ASSESS IMMUNOGENICITY AND POTENCY OF MENINGOCOCCAL CAPSULAR SACCHARIDE VACCINES

RELATED APPLICATION

This application is the U.S. National Phase of International Application No. PCT/US2011/050436, filed Sep. 2, 2011 and published in English, which claims the benefit of U.S. Provisional Application No. 61/380,220, filed Sep. 4, 2010, the complete contents of which are hereby incorporated herein for all purposes.

FIELD OF THE INVENTION

The present invention relates to the field of assays for assessing immunogenicity, potency, or both, of meningococcal capsular saccharide vaccines. In certain embodiments, the present invention relates to use of bactericidal antibody binding as a proxy to assess immunogenicity, potency, or both, rather than immunizing an animal model or merely assessing physical characteristics such as length of saccharide.

BACKGROUND

*Neisseria meningitidis* (meningococcus) is a Gram negative human pathogen. It colonizes the pharynx, causing meningitis and, occasionally, septicemia in the absence of meningitis. It is closely related to *N. gonorrhoeae*, although one feature that clearly differentiates meningococcus is the presence of a polysaccharide capsule that is present in all pathogenic meningococci.

Based on the organism's capsular polysaccharide, twelve serogroups of *N meningitidis* have been identified (A, B, C, H, I, K, L, 29E, W135, X, Y and Z). Group A is the pathogen most often implicated in epidemic disease in sub-Saharan Africa. Serogroups B and C are responsible for the vast majority of cases in USA and in most developed countries. Serogroups W135 and Y are responsible for the remaining cases in USA and developed countries.

A tetravalent vaccine of capsular polysaccharides from serogroups A, C, Y and W135 has been known for many years and has been licensed for human use. Although effective in adolescents and adults, it induces a poor immune response and short duration of protection and cannot be used in infants. This is because polysaccharides are T cell-independent antigens that induce a weak immune response that cannot be boosted. The polysaccharides in this vaccine are not conjugated and are present at a 1:1:1:1 ratio. MENCEVAX ACWY™ contains 50 μg of each purified polysaccharide once reconstituted from its lyophilized form.

Conjugate vaccines against serogroup C have been approved for human use, and include MENJUGATE™, MENINGITEC™ and NEISVAC-C™. Mixtures of conjugates from serogroups A+C+W135+Y have also been approved for human use, and include MENVEO™ and MENACTRA™.

With the proliferation of meningococcal capsular saccharide vaccines, there is a need for methods of assessing the immunogenicity, potency, or both, of each batch of vaccine after manufacture to ensure that each batch will produce the expected immune response without having to immunize a test animal with a sample from each such batch or rely upon mere physical characterization of the capsular saccharide components. Any such method must meet strict governmental regulatory requirements for release of a vaccine that are set by agencies such as the U.S. Food and Drug Administration (the FDA) in the United States and the European Medicines Agency (the EMEA) in Europe. Therefore correlates for immunogenicity, potency, or both that may work in a laboratory will not necessarily meet the requirements of regulatory agencies given that the vaccine will be administered to a human subject. It is therefore an object of the invention to provide methods for assessing immunogenicity, potency, or both, of meningococcal capsular saccharide vaccines that meet the exacting standards of governmental regulatory agencies by measuring binding to a bactericidal antibody specific for the capsular saccharide.

SUMMARY

The disclosure provides compositions, methods and kits for assessing immunogenicity, potency, or both, of meningococcal capsular saccharide vaccines.

One aspect includes methods of assessing immunogenicity of a meningococcal capsular saccharide vaccine for regulatory release including contacting the meningococcal capsular saccharide vaccine with a bactericidal antibody and optionally a control saccharide; assessing the immunogenicity of the meningococcal capsular saccharide vaccine by measuring the binding of the bactericidal antibody to the meningococcal capsular saccharide vaccine or optionally to the control saccharide; and releasing the meningococcal capsular saccharide vaccine if the immunogenicity meets regulatory requirements for release, where the meningococcal capsular saccharide vaccine comprises at least two saccharides selected from (i) an *N. meningitidis* serogroup A capsular saccharide, (ii) an *N. meningitidis* serogroup C capsular saccharide, (iii) an *N. meningitidis* serogroup W capsular saccharide, and (iv) an *N. meningitidis* serogroup Y capsular saccharide, and where the bactericidal antibody binds to one of the at least two saccharides and, optionally, to the control saccharide. In one embodiment, the regulatory release requirements comprise a minimum immunogenicity requirement and a measurement reliability requirement where the measurement reliability requirement can be a coefficient of variation of the measurements being less than a maximum value such as 15% for the coefficient of variation of repeatability (all antigens). In another embodiment that can be combined with the preceding embodiment, the regulatory requirements are determined by the U.S. Food and Drug Administration or the European Medicines Agency. In certain embodiments that can be combined with the preceding embodiments, the at least two saccharides are (i) and (ii); are (ii) and (iv); or are all four saccharides (i)-(iv). In another embodiment that can be combined with any of the preceding embodiments, the at least two saccharides are conjugated to a carrier protein. In another embodiment, the carrier protein can be: diphtheria toxoid; tetanus toxoid; CRM197; protein D from *H. influenzae* or a combination of the foregoing. In another embodiment that can be combined with any of the preceding embodiments, the meningococcal capsular saccharide vaccine is formulated for intramuscular injection. In another embodiment that can be combined with any of the preceding embodiments, the meningococcal capsular saccharide vaccine further comprises an aluminum hydroxide and/or aluminum phosphate adjuvant. In another embodiment that can be combined with any of the preceding embodiments, the meningococcal capsular saccharide vaccine does not include any mercurial material. In another embodiment that can be combined with any of the preceding embodiments, the meningococcal capsular saccharide vaccine further comprises one or more of the following further antigens: (i) a conjugated capsular saccharide from

*Haemophilus influenzae* type B; (ii) a conjugated capsular saccharide from *Streptococcus pneumoniae*; (iii) a protein antigen from *N. meningitidis* serogroup B; (iv) a diphtheria antigen; (v) a tetanus antigen; (vi) a cellular or whole cell pertussis antigen; (vii) one or more acellular pertussis antigens; (viii) an antigen from hepatitis B virus; (ix) one or more poliovirus antigen(s); and (x) an antigen from hepatitis A virus. In another embodiment that can be combined with any of the preceding embodiments, the meningococcal capsular saccharide vaccine further comprises a sugar alcohol or sucrose. In another embodiment that can be combined with any of the preceding embodiments, the optional control saccharide is included, the binding of the bactericidal antibody to the control saccharide is measured and the meningococcal capsular saccharide vaccine competes with the control saccharide for binding to the bactericidal antibody. In another embodiment that can be combined with any of the preceding embodiments including the control saccharide, wherein the control saccharide is selected from the group consisting of: a native capsular polysaccharide from the same serogroup as one of the at least two saccharides, a capsular oligosaccharide from the same serogroup as one of the at least two saccharides, a synthetic saccharide, a conjugate of any of the preceding, or a combination of one or more of the preceding. In another embodiment that can be combined with any of the preceding embodiments including the control saccharide, measuring the binding includes adding a secondary antibody that binds to the bactericidal antibody wherein the secondary antibody is conjugated to an enzyme that catalyzes a detectable reaction such as alkaline phosphatase or horseradish peroxidase. In another embodiment that can be combined with any of the preceding embodiments including the control saccharide, measuring the binding includes serially diluting the meningococcal capsular saccharide vaccine. In another embodiment, the serial dilution includes at least one, at least two, at least three, at least four, or at least five points in a linear portion of an inhibition curve calculated with measurements from the serial dilution. In another embodiment, the immunogenicity is assessed by comparing the inhibition curve with a reference inhibition curve for a reference capsular saccharide of the same serogroup of known immunogenicity. In another embodiment, the comparing is performed by taking the anti-log of the difference between the reference inhibition curve intercept for the reference capsular saccharide and the inhibition curve intercept for the meningococcal capsular saccharide vaccine divided by the common slope. In another embodiment that can be combined with any of the preceding embodiments including a serial dilution, the serial dilution is in a multiwell plate such as a 96 well microtiter plate or a 384 well microtiter plate. In another embodiment that can be combined with any of the preceding embodiments including the control saccharide and a multiwell plate, the control saccharide is bound to a surface of at least one well of the multiwell plate. In another embodiment that can be combined with any of the preceding embodiments including a serial dilution, wherein the serial dilution is a series of 2- or 3-fold dilutions if the control saccharide is from serogroups C, Y, or W or a series of 5-fold dilutions if the control saccharide is from serogroup A.

Another aspect includes more general methods of assessing immunogenicity of a meningococcal capsular saccharide vaccine comprising contacting the meningococcal capsular saccharide vaccine with a bactericidal antibody and optionally a control saccharide; and assessing the immunogenicity of the meningococcal capsular saccharide vaccine by measuring the binding of the bactericidal antibody to the meningococcal capsular saccharide vaccine or optionally to the control saccharide, where the meningococcal capsular saccharide vaccine comprises at least two saccharides selected from (i) an *N. meningitidis* serogroup A capsular saccharide, (ii) an *N. meningitidis* serogroup C capsular saccharide, (iii) an *N. meningitidis* serogroup W capsular saccharide, and (iv) an *N. meningitidis* serogroup Y capsular saccharide, and where the bactericidal antibody binds to one of the at least two saccharides and, optionally, to the control saccharide. In certain embodiments, the at least two saccharides are (i) and (ii); are (ii) and (iv); or include all four saccharides (i)-(iv). In another embodiment that can be combined with any of the preceding embodiments, the at least two saccharides are conjugated to a carrier protein. In another embodiment, the carrier protein can be: diphtheria toxoid; tetanus toxoid; CRM197; protein D from *H. influenzae* or a combination of the foregoing. In another embodiment that can be combined with any of the preceding embodiments, the meningococcal capsular saccharide vaccine is formulated for intramuscular injection. In another embodiment that can be combined with any of the preceding embodiments, the meningococcal capsular saccharide vaccine further comprises an aluminum hydroxide and/or aluminum phosphate adjuvant. In another embodiment that can be combined with any of the preceding embodiments, the meningococcal capsular saccharide vaccine does not include any mercurial material. In another embodiment that can be combined with any of the preceding embodiments, the meningococcal capsular saccharide vaccine further comprises one or more of the following further antigens: (i) a conjugated capsular saccharide from *Haemophilus influenzae* type B; (ii) a conjugated capsular saccharide from *Streptococcus pneumoniae*; (iii) a protein antigen from *N. meningitidis* serogroup B; (iv) a diphtheria antigen; (v) a tetanus antigen; (vi) a cellular or whole cell pertussis antigen; (vii) one or more acellular pertussis antigens; (viii) an antigen from hepatitis B virus; (ix) one or more poliovirus antigen(s); and (x) an antigen from hepatitis A virus. In another embodiment that can be combined with any of the preceding embodiments, the meningococcal capsular saccharide vaccine further comprises a sugar alcohol or sucrose. In another embodiment that can be combined with any of the preceding embodiments, the optional control saccharide is included, the binding of the bactericidal antibody to the control saccharide is measured and the meningococcal capsular saccharide vaccine competes with the control saccharide for binding to the bactericidal antibody. In another embodiment that can be combined with any of the preceding embodiments including the control saccharide, wherein the control saccharide is selected from the group consisting of: a native capsular polysaccharide from the same serogroup as one of the at least two saccharides, a capsular oligosaccharide from the same serogroup as one of the at least two saccharides, a synthetic saccharide, a conjugate of any of the preceding, or a combination of one or more of the preceding. In another embodiment that can be combined with any of the preceding embodiments including the control saccharide, measuring the binding includes adding a secondary antibody that binds to the bactericidal antibody wherein the secondary antibody is conjugated to an enzyme that catalyzes a detectable reaction such as alkaline phosphatase or horseradish peroxidase. In another embodiment that can be combined with any of the preceding embodiments including the control saccharide, measuring the binding includes serially diluting the meningococcal capsular saccharide vaccine. In another embodiment, the serial dilution includes at least one, at least two, at least three, at least four, or at least five points in a linear portion of an inhibition curve calculated with measurements from the serial dilution. In another embodiment, the immunogenicity is assessed by comparing the inhibition curve with a reference inhibition curve for a reference capsular saccharide of the same serogroup of known immunogenicity. In another embodiment, the comparing is performed by taking the anti-log of the difference between the reference inhibition curve intercept for the reference capsular saccharide and the inhibition curve intercept for the meningococcal capsular saccharide vaccine divided by the common slope. In another embodiment that can be combined with any of the preceding embodiments including a serial dilution, the serial dilution is in a multiwell plate such as a 96 well microtiter plate or a 384 well microtiter plate. In another embodiment that can be combined with any of the preceding embodiments including the control saccharide and a multiwell plate, the control saccharide is bound to a surface of at least one well of the multiwell plate. In another embodiment that can be combined with any of the preceding embodiments including a serial dilution, wherein the serial dilution is a series of 2- or 3-fold dilutions if the control saccharide is from serogroups C, Y, or W or a series of 5-fold dilutions if the control saccharide is from serogroup A.

Yet another aspect includes kit for assessing immunogenicity of a meningococcal capsular saccharide vaccine for release that include a multiwell plate; a control saccharide to bind to a surface of at least one of the wells; and a bactericidal antibody, where the meningococcal capsular saccharide vaccine comprises at least two saccharides selected from (i) an *N. meningitidis* serogroup A capsular saccharide, (ii) an *N. meningitidis* serogroup C capsular saccharide, (iii) an *N. meningitidis* serogroup W capsular saccharide, and (iv) an *N. meningitidis* serogroup Y capsular saccharide, and where the bactericidal antibody sample binds to one of the at least two saccharides and the control saccharide. In one embodiment, the kits may further include a bactericidal antibody dilution buffer, wherein the bactericidal antibody dilution buffer optionally includes a detergent (e.g., TWEEN 20™). In another embodiment that may be combined with the preceding embodiment, the kits also include a vaccine dilution buffer. In another embodiment that may be combined with either of the preceding embodiments, the control saccharide may be a native capsular polysaccharide from the same serogroup as one of the at least two saccharides, a capsular oligosaccharide from the same serogroup as one of the at least two saccharides, a synthetic saccharide, or a conjugate of any of the preceding. In another embodiment that may be combined with any of the preceding embodiments, the control saccharide is the native capsular polysaccharide. In another embodiment that may be combined with any of the preceding embodiments, the bactericidal antibody is stored at −20° C. in a buffer that includes a serum albumin protein. In another embodiment that may be combined with any of the preceding embodiments, the kit comprises a specific bactericidal antibody for each of the at least two bactericidal antibodies saccharides, one of which is the bactericidal antibody.

Another aspect includes methods of assessing potency of a meningococcal capsular saccharide vaccine for regulatory release including contacting the meningococcal capsular saccharide vaccine with a bactericidal antibody and optionally a control saccharide; assessing the potency of the meningococcal capsular saccharide vaccine by measuring the binding of the bactericidal antibody to the meningococcal capsular saccharide vaccine or optionally to the control saccharide; and releasing the meningococcal capsular saccharide vaccine if the potency meets regulatory requirements for release, where the meningococcal capsular saccharide vaccine comprises at least two saccharides selected from (i) an *N. meningitidis* serogroup A capsular saccharide, (ii) an *N. meningitidis* serogroup C capsular saccharide, (iii) an *N. meningitidis* serogroup W capsular saccharide, and (iv) an *N. meningitidis* serogroup Y capsular saccharide, and where the bactericidal antibody binds to one of the at least two saccharides and, optionally, to the control saccharide. In one embodiment, the regulatory release requirements comprise a minimum potency requirement and a measurement reliability requirement where the measurement reliability requirement can be a coefficient of variation of the measurements being less than a maximum value such as 15% for the coefficient of variation of repeatability (all antigens) of. In another embodiment that can be combined with the preceding embodiment, the regulatory requirements are determined by the U.S. Food and Drug Administration or the European Medicines Agency. In certain embodiments that can be combined with the preceding embodiments, the at least two saccharides are (i) and (ii); are (ii) and (iv); or are all four saccharides (i)-(iv). In another embodiment that can be combined with any of the preceding embodiments, the at least two saccharides are conjugated to a carrier protein. In another embodiment, the carrier protein can be: diphtheria toxoid; tetanus toxoid; CRM197; protein D from *H. influenzae* or a combination of the foregoing. In another embodiment that can be combined with any of the preceding embodiments, the meningococcal capsular saccharide vaccine is formulated for intramuscular injection. In another embodiment that can be combined with any of the preceding embodiments, the meningococcal capsular saccharide vaccine further comprises an aluminum hydroxide and/or aluminum phosphate adjuvant. In another embodiment that can be combined with any of the preceding embodiments, the meningococcal capsular saccharide vaccine does not include any mercurial material. In another embodiment that can be combined with any of the preceding embodiments, the meningococcal capsular saccharide vaccine further comprises one or more of the following further antigens: (i) a conjugated capsular saccharide from *Haemophilus influenzae* type B; (ii) a conjugated capsular saccharide from *Streptococcus pneumoniae*; (iii) a protein antigen from *N. meningitidis* serogroup B; (iv) a diphtheria antigen; (v) a tetanus antigen; (vi) a cellular or whole cell pertussis antigen; (vii) one or more acellular pertussis antigens; (viii) an antigen from hepatitis B virus; (ix) one or more poliovirus antigen(s); and (x) an antigen from hepatitis A virus. In another embodiment that can be combined with any of the preceding embodiments, the meningococcal capsular saccharide vaccine further comprises a sugar alcohol or sucrose. In another embodiment that can be combined with any of the preceding embodiments, the optional control saccharide is included, the binding of the bactericidal antibody to the control saccharide is measured and the meningococcal capsular saccharide vaccine competes with the control saccharide for binding to the bactericidal antibody. In another embodiment that can be combined with any of the preceding embodiments including the control saccharide, wherein the control saccharide is selected from the group consisting of: a native capsular polysaccharide from the same serogroup as one of the at least two saccharides, a capsular oligosaccharide from the same serogroup as one of the at least two saccharides, a synthetic saccharide, a conjugate of any of the preceding, or a combination of one or more of the preceding. In another embodiment that can be combined with any of the preceding embodiments including the control saccharide, measuring the binding includes adding a secondary antibody that binds to the bactericidal antibody wherein the secondary antibody is conjugated to an enzyme that catalyzes a detectable reaction such as alkaline phosphatase or horseradish peroxidase. In another embodiment that can be combined with any of the preceding embodiments including the control saccharide, measuring the binding includes serially diluting the meningococcal capsular saccharide vaccine. In another embodiment, the serial dilution includes at least one, at least two, at least three, at least four, or at least five points in a linear portion of an inhibition curve calculated with measurements from the serial dilution. In another embodiment, the potency is assessed by comparing the inhibition curve with a reference inhibition curve for a reference capsular saccharide of the same serogroup of known potency. In another embodiment, the comparing is performed by taking the anti-natural log of the difference between the reference inhibition curve intercept for the reference capsular saccharide and the inhibition curve intercept for the meningococcal capsular saccharide vaccine divided by the common slope. In another embodiment that can be combined with any of the preceding embodiments including a serial dilution, the serial dilution is in a multiwell plate such as a 96 well microtiter plate or a 384 well microtiter plate. In another embodiment that can be combined with any of the preceding embodiments including the control saccharide and a multiwell plate, the control saccharide is bound to a surface of at least one well of the multiwell plate. In another embodiment that can be combined with any of the preceding embodiments including a serial dilution, wherein the serial dilution is a series of 2- or 3-fold dilutions if the control saccharide is from serogroups C, Y, or W or a series of 5-fold dilutions if the control saccharide is from serogroup A.

Still another aspect includes more general methods of assessing potency of a meningococcal capsular saccharide vaccine comprising contacting the meningococcal capsular saccharide vaccine with a bactericidal antibody and optionally a control saccharide; and assessing the potency of the meningococcal capsular saccharide vaccine by measuring the binding of the bactericidal antibody to the meningococcal capsular saccharide vaccine or optionally to the control saccharide, where the meningococcal capsular saccharide vaccine comprises at least two saccharides selected from (i) an *N. meningitidis* serogroup A capsular saccharide, (ii) an *N. meningitidis* serogroup C capsular saccharide, (iii) an *N. meningitidis* serogroup W capsular saccharide, and (iv) an *N. meningitidis* serogroup Y capsular saccharide, and where the bactericidal antibody binds to one of the at least two saccharides and, optionally, to the control saccharide. In certain embodiments, the at least two saccharides are (i) and (ii); are (ii) and (iv); or include all four saccharides (i)-(iv). In another embodiment that can be combined with any of the preceding embodiments, the at least two saccharides are conjugated to a carrier protein. In another embodiment, the carrier protein can be: diphtheria toxoid; tetanus toxoid; CRM197; protein D from *H. influenzae* or a combination of the foregoing. In another embodiment that can be combined with any of the preceding embodiments, the meningococcal capsular saccharide vaccine is formulated for intramuscular injection. In another embodiment that can be combined with any of the preceding embodiments, the meningococcal capsular saccharide vaccine further comprises an aluminum hydroxide and/or aluminum phosphate adjuvant. In another embodiment that can be combined with any of the preceding embodiments, the meningococcal capsular saccharide vaccine does not include any mercurial material. In another embodiment that can be combined with any of the preceding embodiments, the meningococcal capsular saccharide vaccine further comprises one or more of the following further antigens: (i) a conjugated capsular saccharide from *Haemophilus influenzae* type B; (ii) a conjugated capsular saccharide from *Streptococcus pneumoniae*; (iii) a protein antigen from *N. meningitidis* serogroup B; (iv) a diphtheria antigen; (v) a tetanus antigen; (vi) a cellular or whole cell pertussis antigen; (vii) one or more acellular pertussis antigens; (viii) an antigen from hepatitis B virus; (ix) one or more poliovirus antigen(s); and (x) an antigen from hepatitis A virus. In another embodiment that can be combined with any of the preceding embodiments, the meningococcal capsular saccharide vaccine further comprises a sugar alcohol or sucrose. In another embodiment that can be combined with any of the preceding embodiments, the optional control saccharide is included, the binding of the bactericidal antibody to the control saccharide is measured and the meningococcal capsular saccharide vaccine competes with the control saccharide for binding to the bactericidal antibody. In another embodiment that can be combined with any of the preceding embodiments including the control saccharide, wherein the control saccharide is selected from the group consisting of: a native capsular polysaccharide from the same serogroup as one of the at least two saccharides, a capsular oligosaccharide from the same serogroup as one of the at least two saccharides, a synthetic saccharide, a conjugate of any of the preceding, or a combination of one or more of the preceding. In another embodiment that can be combined with any of the preceding embodiments including the control saccharide, measuring the binding includes adding a secondary antibody that binds to the bactericidal antibody wherein the secondary antibody is conjugated to an enzyme that catalyzes a detectable reaction such as alkaline phosphatase or horseradish peroxidase. In another embodiment that can be combined with any of the preceding embodiments including the control saccharide, measuring the binding includes serially diluting the meningococcal capsular saccharide vaccine. In another embodiment, the serial dilution includes at least one, at least two, at least three, at least four, or at least five points in a linear portion of an inhibition curve calculated with measurements from the serial dilution. In another embodiment, the potency is assessed by comparing the inhibition curve with a reference inhibition curve for a reference capsular saccharide of the same serogroup of known potency. In another embodiment, the comparing is performed by taking the anti-log of the difference between the reference inhibition curve intercept for the reference capsular saccharide and the inhibition curve intercept for the meningococcal capsular saccharide vaccine divided by the common slope. In another embodiment that can be combined with any of the preceding embodiments including a serial dilution, the serial dilution is in a multiwell plate such as a 96 well microtiter plate or a 384 well microtiter plate. In another embodiment that can be combined with any of the preceding embodiments including the control saccharide and a multiwell plate, the control saccharide is bound to a surface of at least one well of the multiwell plate. In another embodiment that can be combined with any of the preceding embodiments including a serial dilution, wherein the serial dilution is a series of 2 or 3-fold dilutions if the control saccharide is from serogroups C, Y, or W or a series of 5-fold dilutions if the control saccharide is from serogroup A.

Yet another aspect includes kit for assessing potency of a meningococcal capsular saccharide vaccine for release that include a multiwell plate; a control saccharide to bind to a surface of at least one of the wells; and a bactericidal antibody, where the meningococcal capsular saccharide vaccine comprises at least two saccharides selected from (i) an *N. meningitidis* serogroup A capsular saccharide, (ii) an *N. meningitidis* serogroup C capsular saccharide, (iii) an *N. meningitidis* serogroup W capsular saccharide, and (iv) an *N. meningitidis* serogroup Y capsular saccharide, and where the bactericidal antibody sample binds to one of the at least two saccharides and the control saccharide. In one embodiment, the kits may further include a bactericidal antibody dilution buffer, wherein the bactericidal antibody dilution buffer optionally includes a detergent (e.g., TWEEN 20™). In another embodiment that may be combined with the preceding embodiment, the kits also include a vaccine dilution buffer. In another embodiment that may be combined with either of the preceding embodiments, the control saccharide may be a native capsular polysaccharide from the same serogroup as one of the at least two saccharides, a capsular oligosaccharide from the same serogroup as one of the at least two saccharides, a synthetic saccharide, or a conjugate of any of the preceding. In another embodiment that may be combined with any of the preceding embodiments, the control saccharide is the native capsular polysaccharide. In another embodiment that may be combined with any of the preceding embodiments, the bactericidal antibody is stored at −20° C. in a buffer that includes a serum albumin protein. In another embodiment that may be combined with any of the preceding embodiments, the kit comprises a specific bactericidal antibody and a control saccharide for each of the at least two saccharides in the meningococcal capsular saccharide vaccine.

SUMMARY OF THE DRAWINGS

FIGS. 1A-1H shows a comparison of inhibition curves obtained with a negative control (triangles) and a reference standard (the Menveo vaccine—squares) with bactericidal monoclonal antibodies in plates coated with native polysaccharide (panel A), (panel C), (panel E), and (panel G) and with oligosaccharide-$CRM_{197}$ conjugates (panel B), (panel D), (panel F), and (panel H).

FIGS. 4A-4F show the MenW135 Linear Plot of log OD versus log concentration for the six plates (circles identify points excluded from the linear regression analysis due to being outside the linear range, while the solid dots are the points included in the analysis).

FIGS. 5A-5F show the MenY Linear Plot of log OD versus log concentration for the six plates (circles identify points excluded from the linear regression analysis due to being outside the linear range, while the solid dots are the points included in the analysis).

FIGS. 6A-6D show the comparison between the Standard curve (dark grey diamonds) and negative controls for MenA, C, W135 and Y antigens ("test vaccine"—light grey circles). Panel (A) shows the plot of log OD vs. log concentration for MenA. Panel (B) shows the plot of log OD vs. log concentration for MenC. Panel (C) shows the plot of log OD vs. log concentration for MenW135. Panel (D) shows the plot of log OD vs. log concentration for MenY.

FIGS. 7A-7B: Panel (A) shows the plot of log OD vs. log concentration for mAb anti MenW135 inhibited by Standard vaccine (light grey circles) and oligoW-CRM conj (dark grey triangle); p-value=0.66. Panel (B) shows the plot of log OD vs. log concentration for mAb anti MenW-135 inhibited by Standard vaccine (light grey circles) and oligoC-CRM conj (dark grey triangles); p-value=0.00.

DETAILED DESCRIPTION OF THE PREFERRED EMBODIMENTS

Figure 1G:
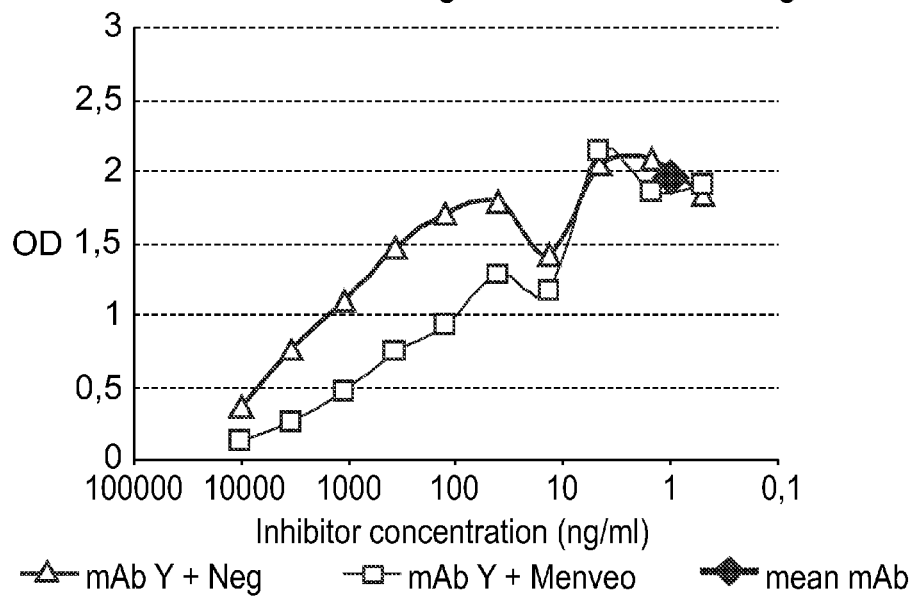
Figure 1H:
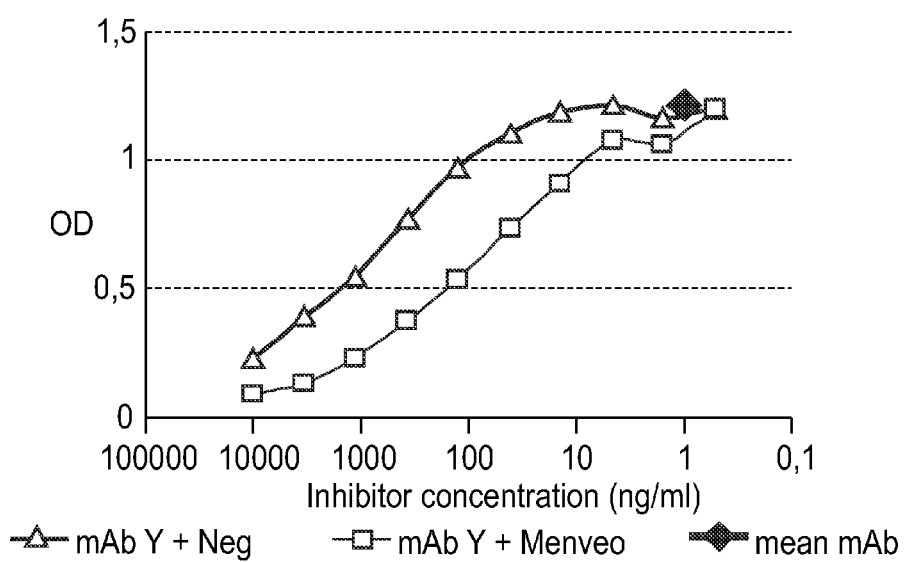
Figure 2A:
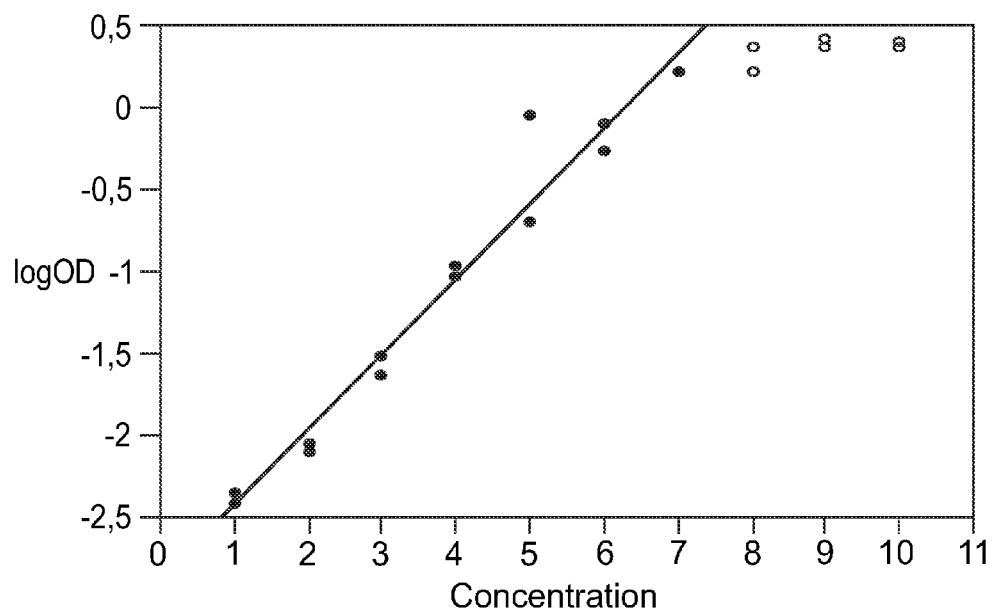
FIGS. 2A-2F show the MenA Linear Plot of logOD versus log concentration for the six plates (circles identify points excluded from the linear regression analysis due to being outside the linear range, while the solid dots are the points included in the analysis).
Figure 2B:
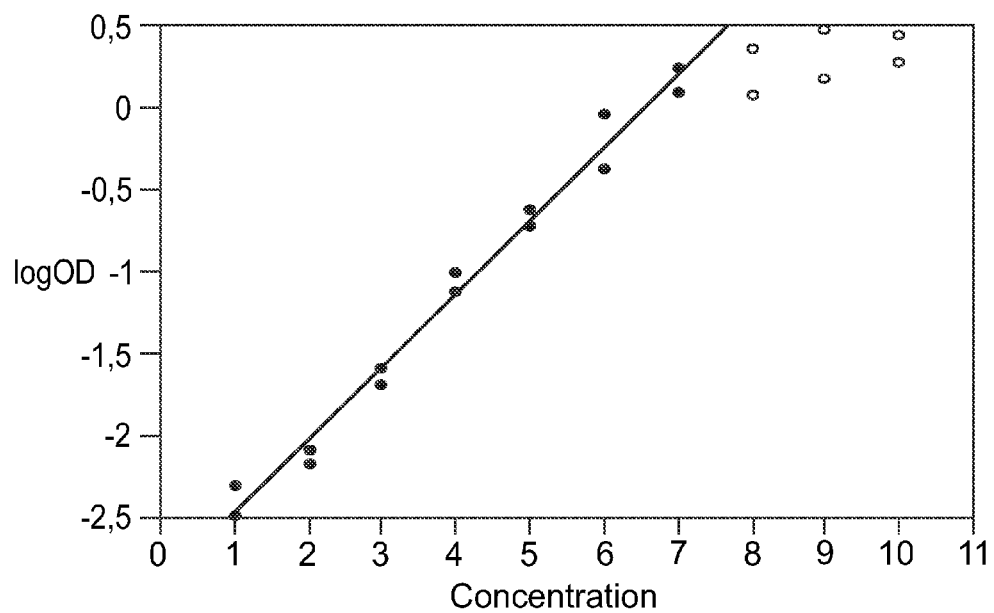
Figure 2C:
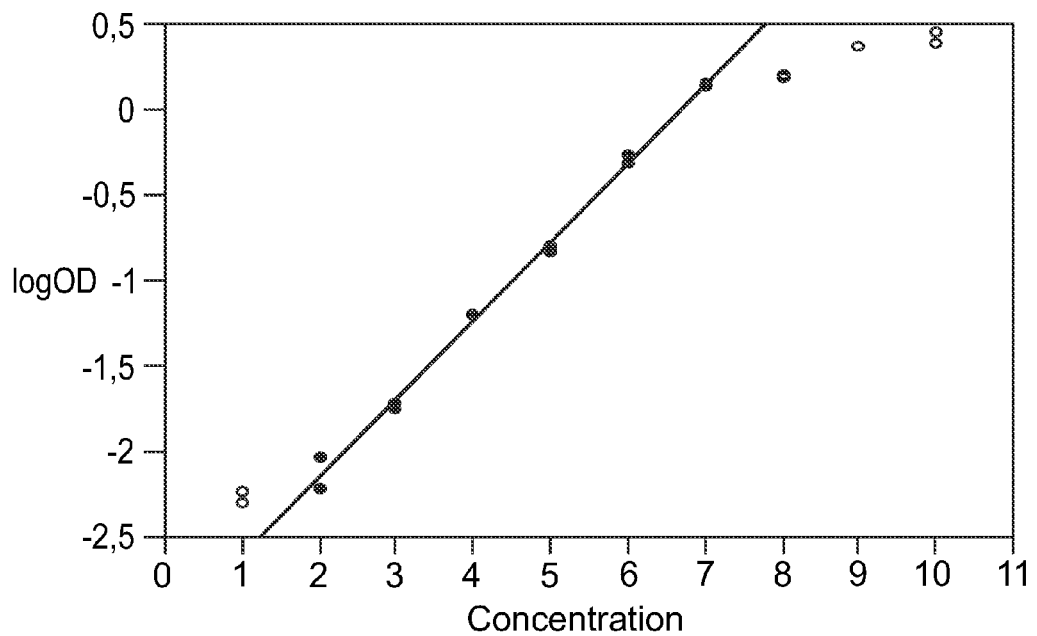
Figure 2D:
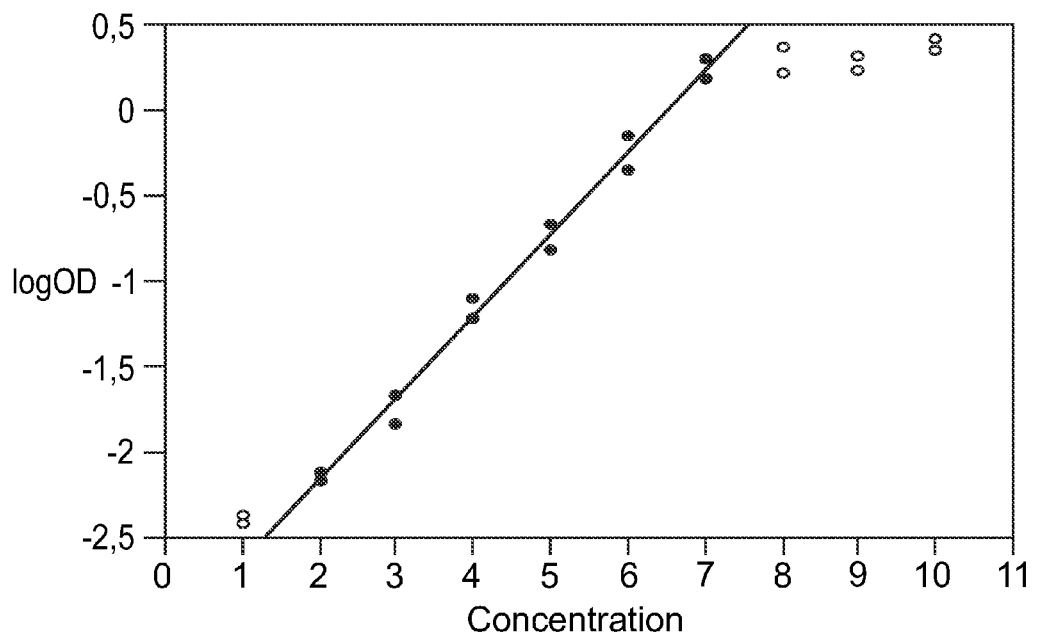
Figure 2E:
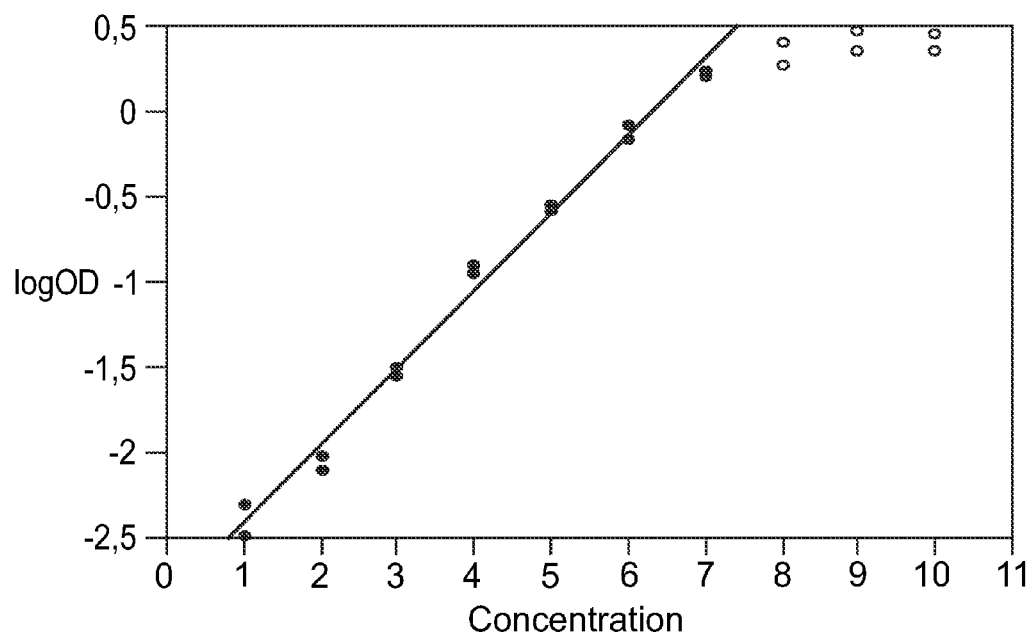
Figure 2F:
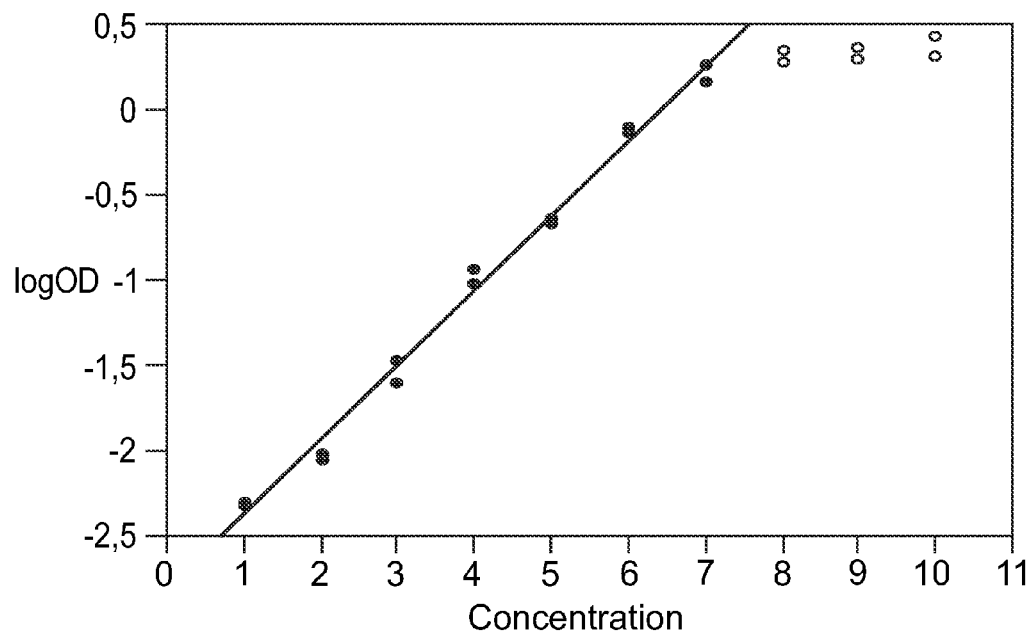
Figure 3A:
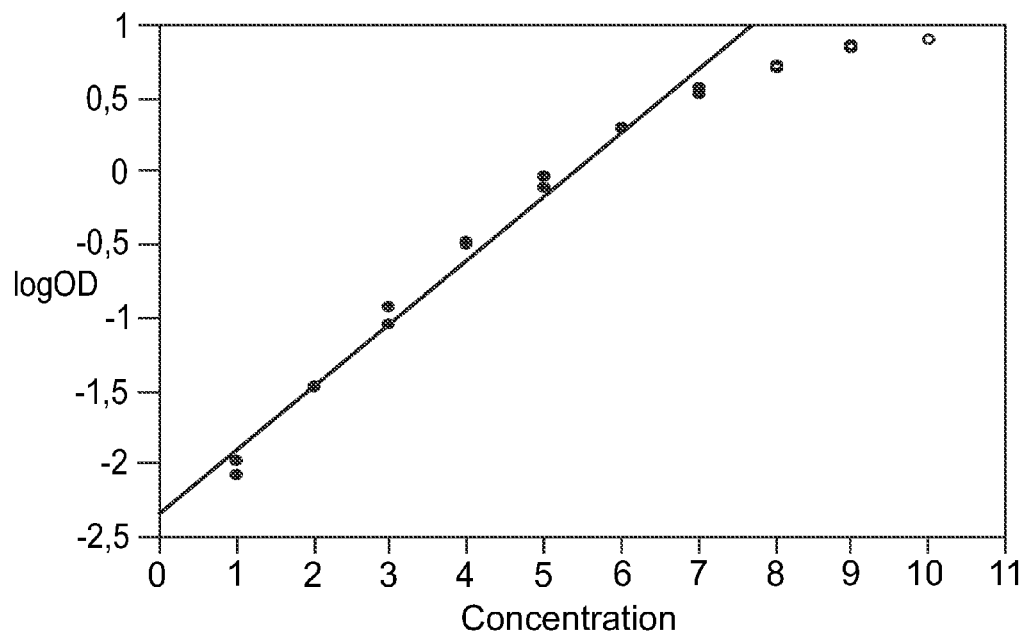
FIGS. 3A-3F show the MenC Linear Plot of log OD versus log concentration for the six plates (circles identify points excluded from the linear regression analysis due to being outside the linear range, while the solid dots are the points included in the analysis).
Figure 3B:
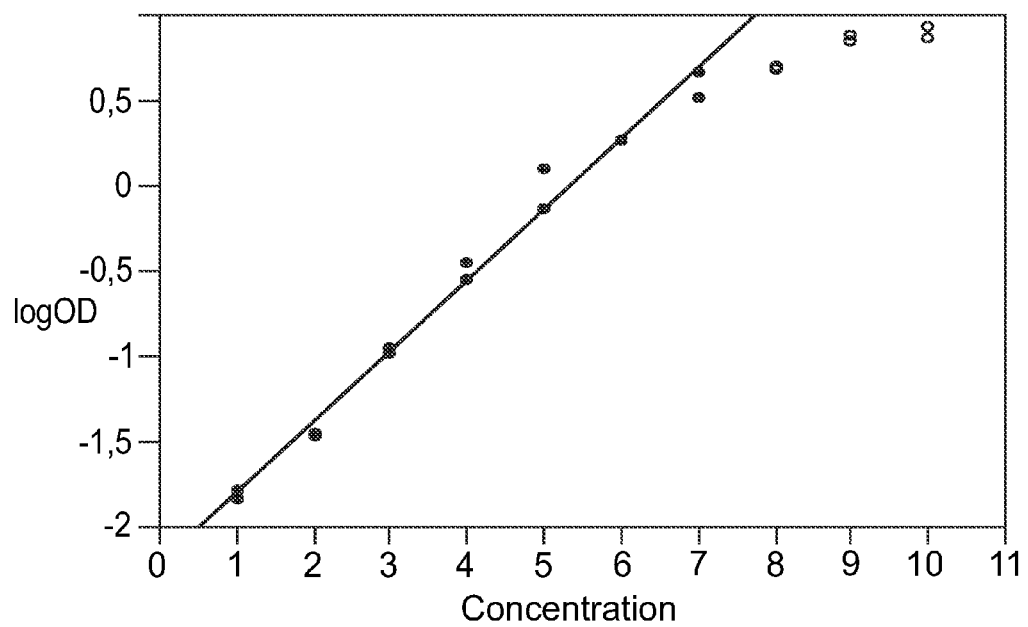
Figure 3C:
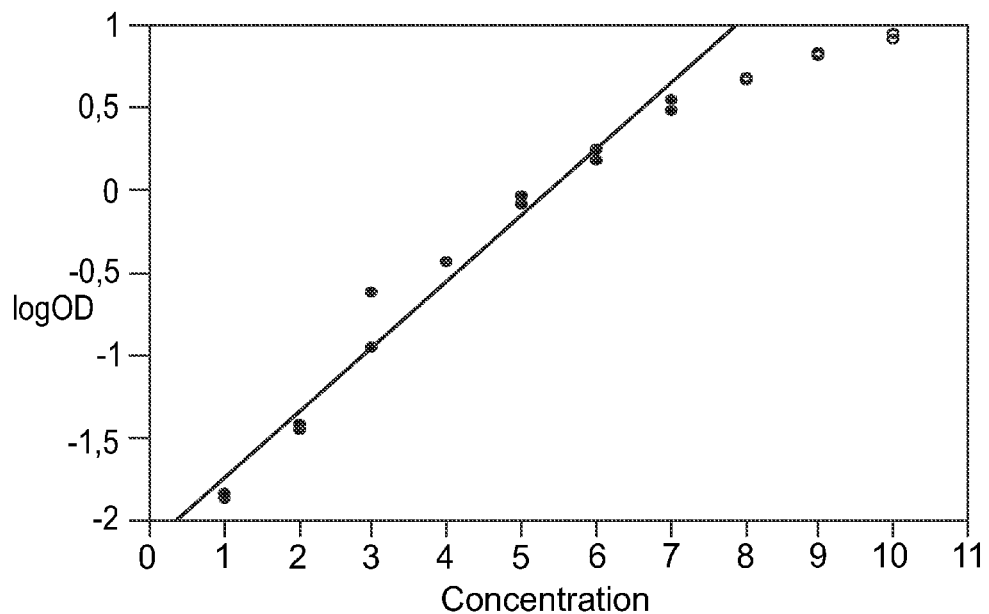
Figure 3D:
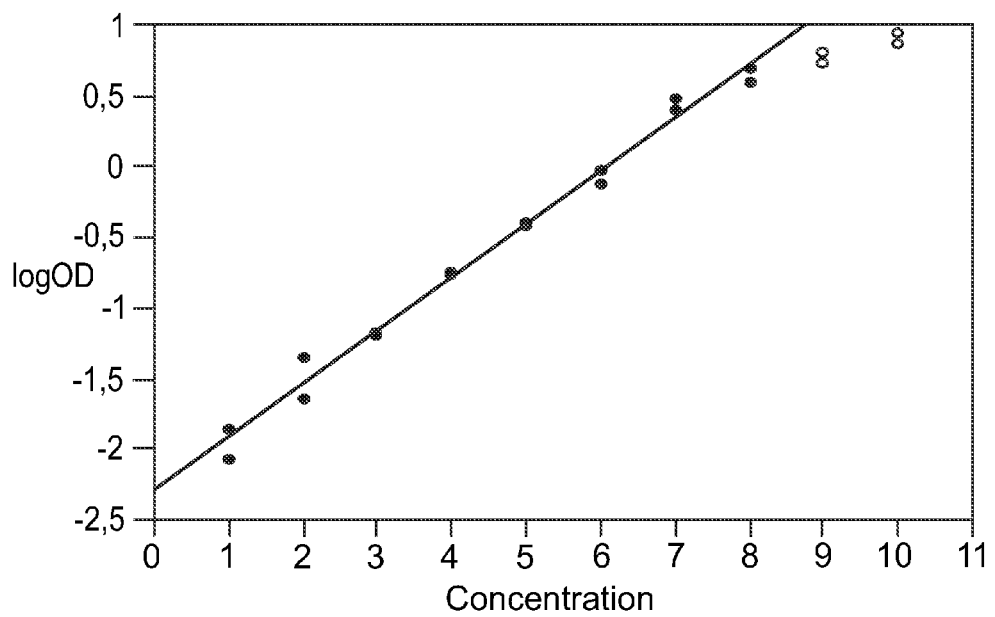
Figure 3E:
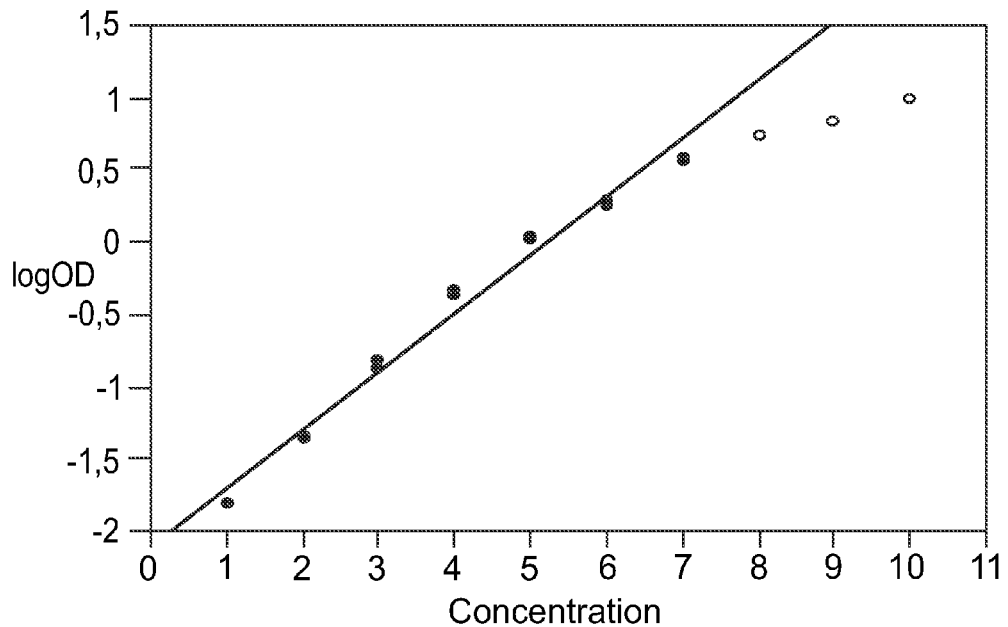
Figure 3F:
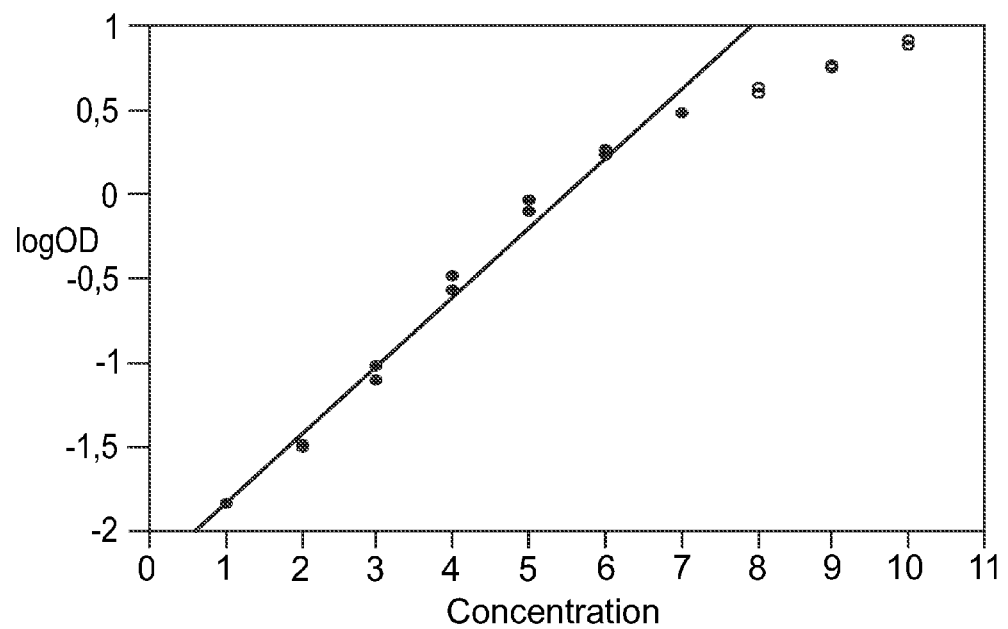
Figure 4C:
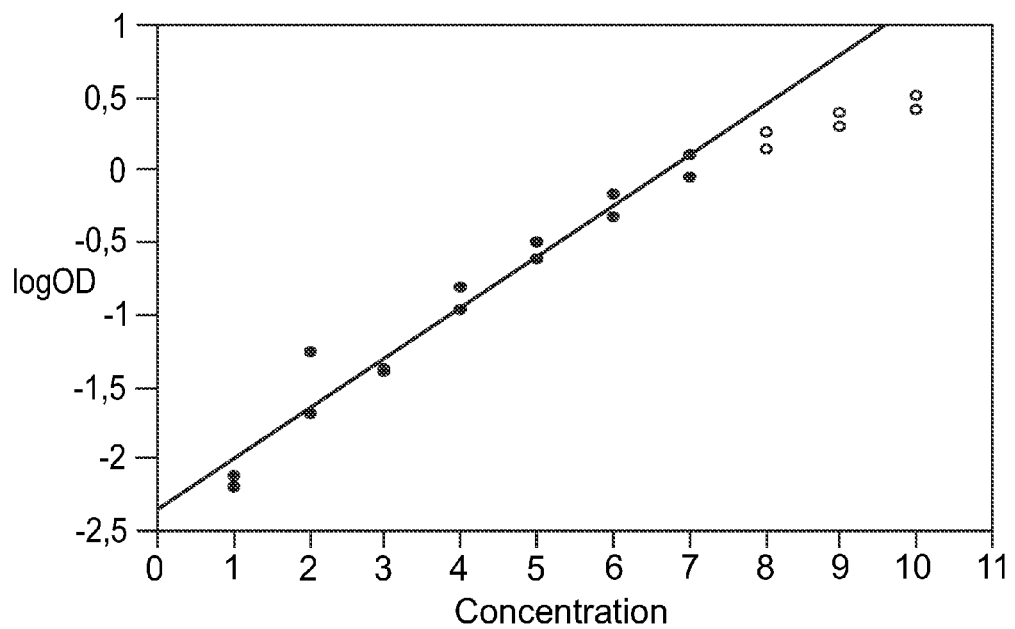
Figure 4D:
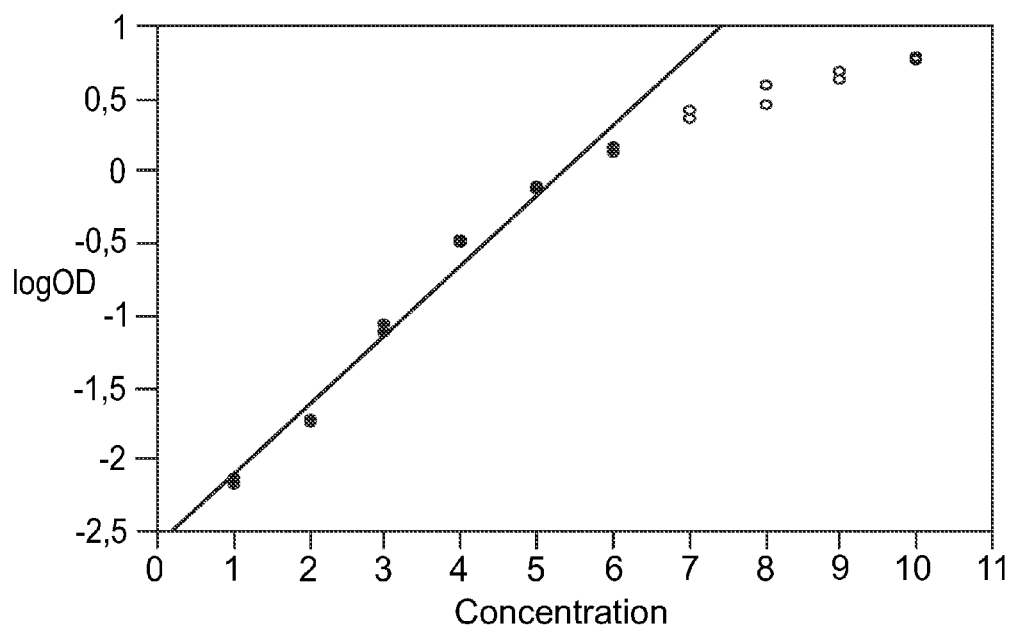
Figure 4E:
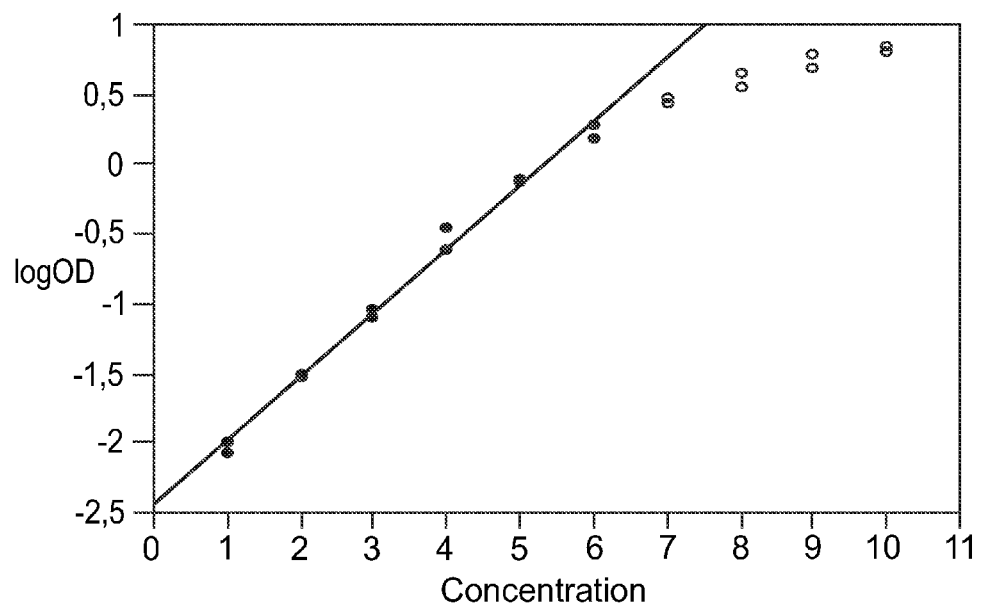
Figure 4F:
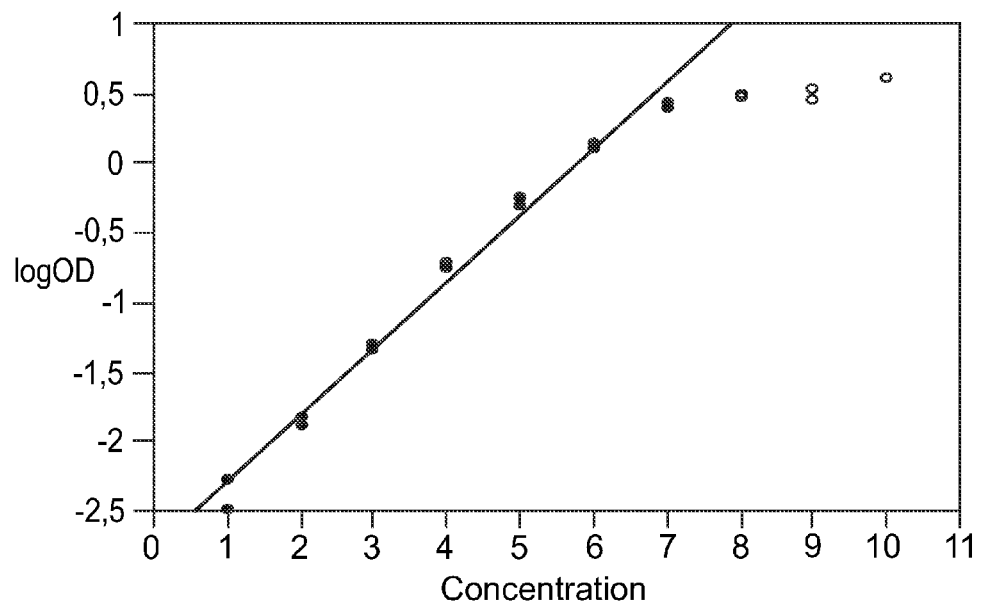
Figure 5A:
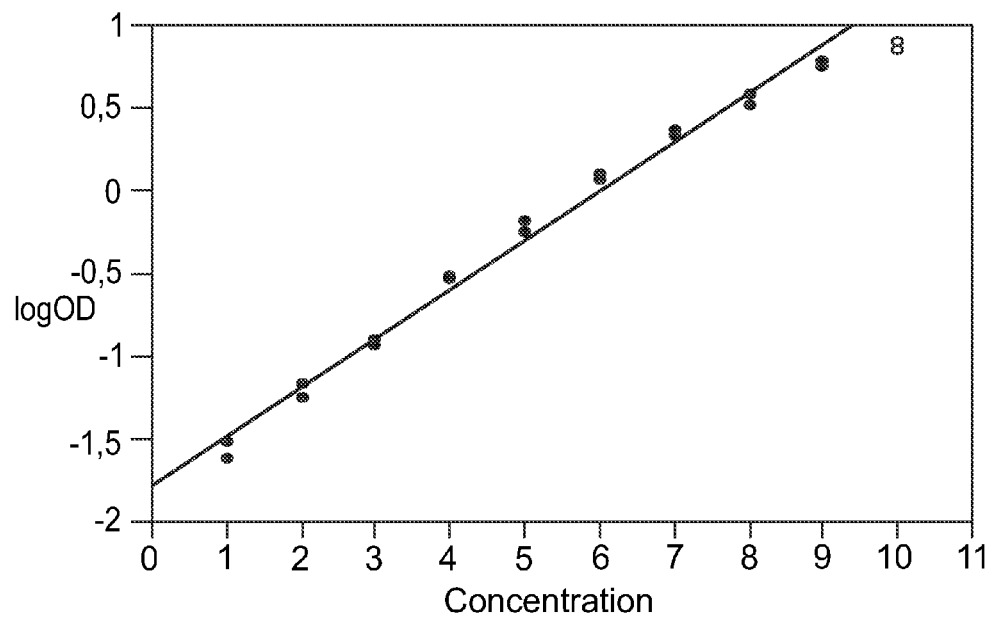
Figure 5B:
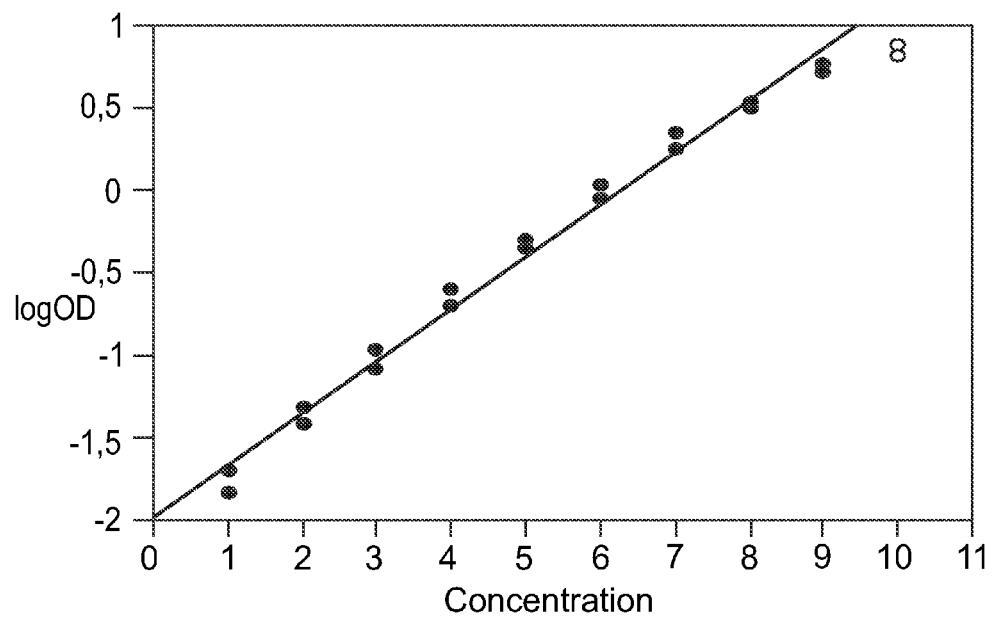
Figure 5E:
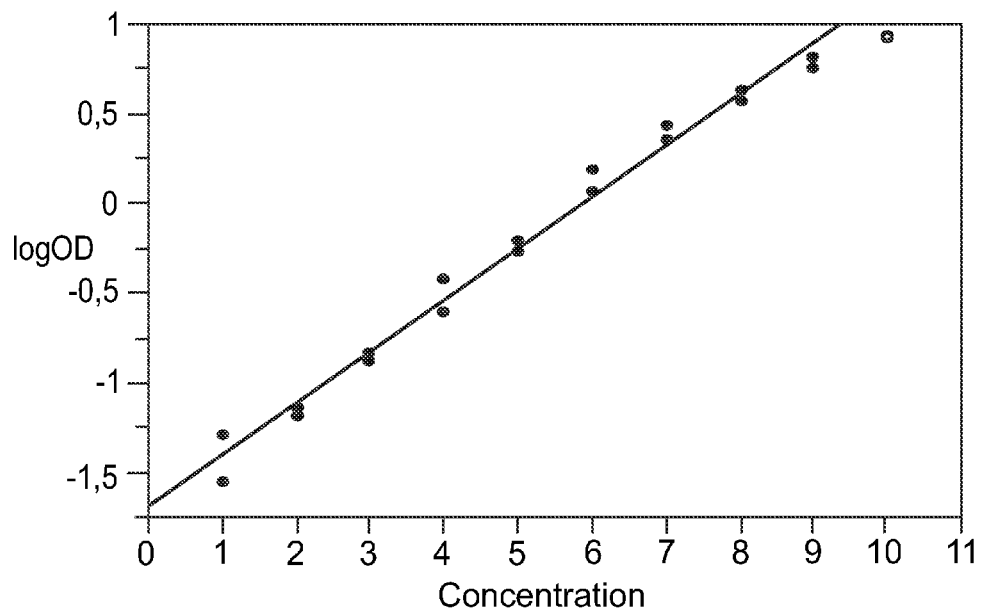
Figure 5F:
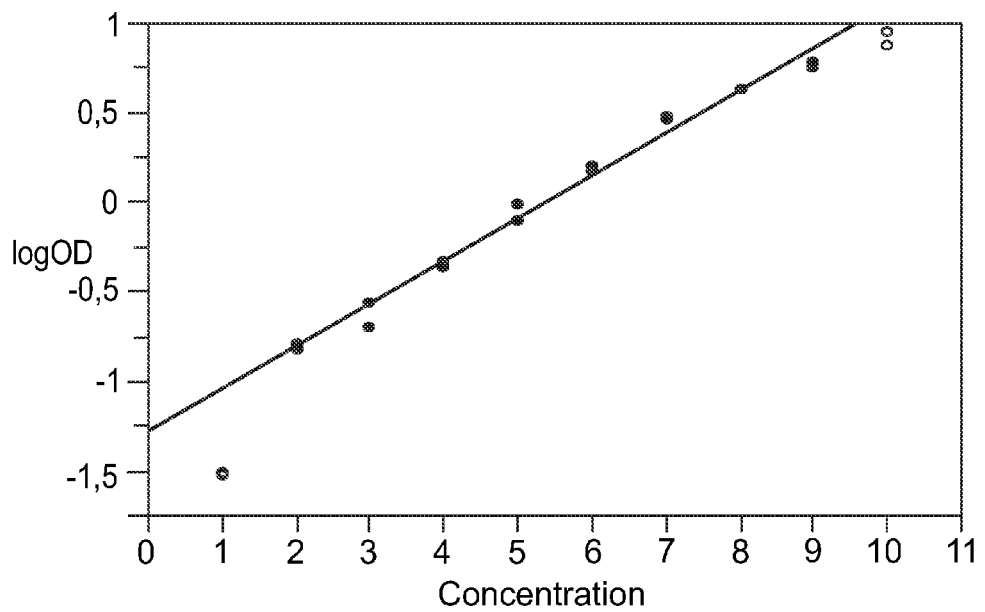
Figure 8A:
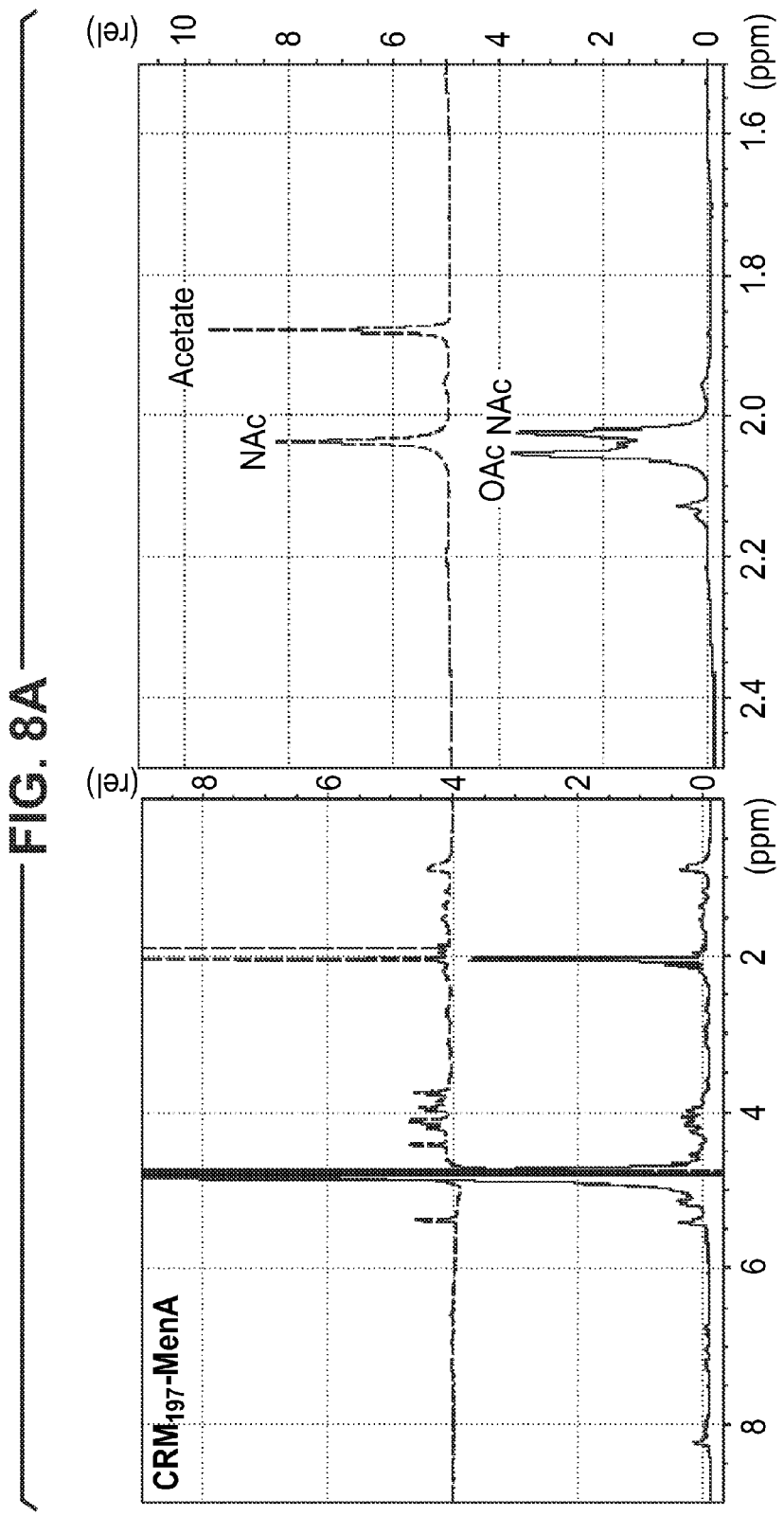
FIGS. 8A-8D: $^1$H NMR profiles of $CRM_{197}$-MenA (Panel A), -MenC (Panel B), -$MenW_{135}$ (Panel C) and -MenY (Panel D) conjugate samples before (dotted line) and after de-O-acetylation (solid line).
Figure 8B:
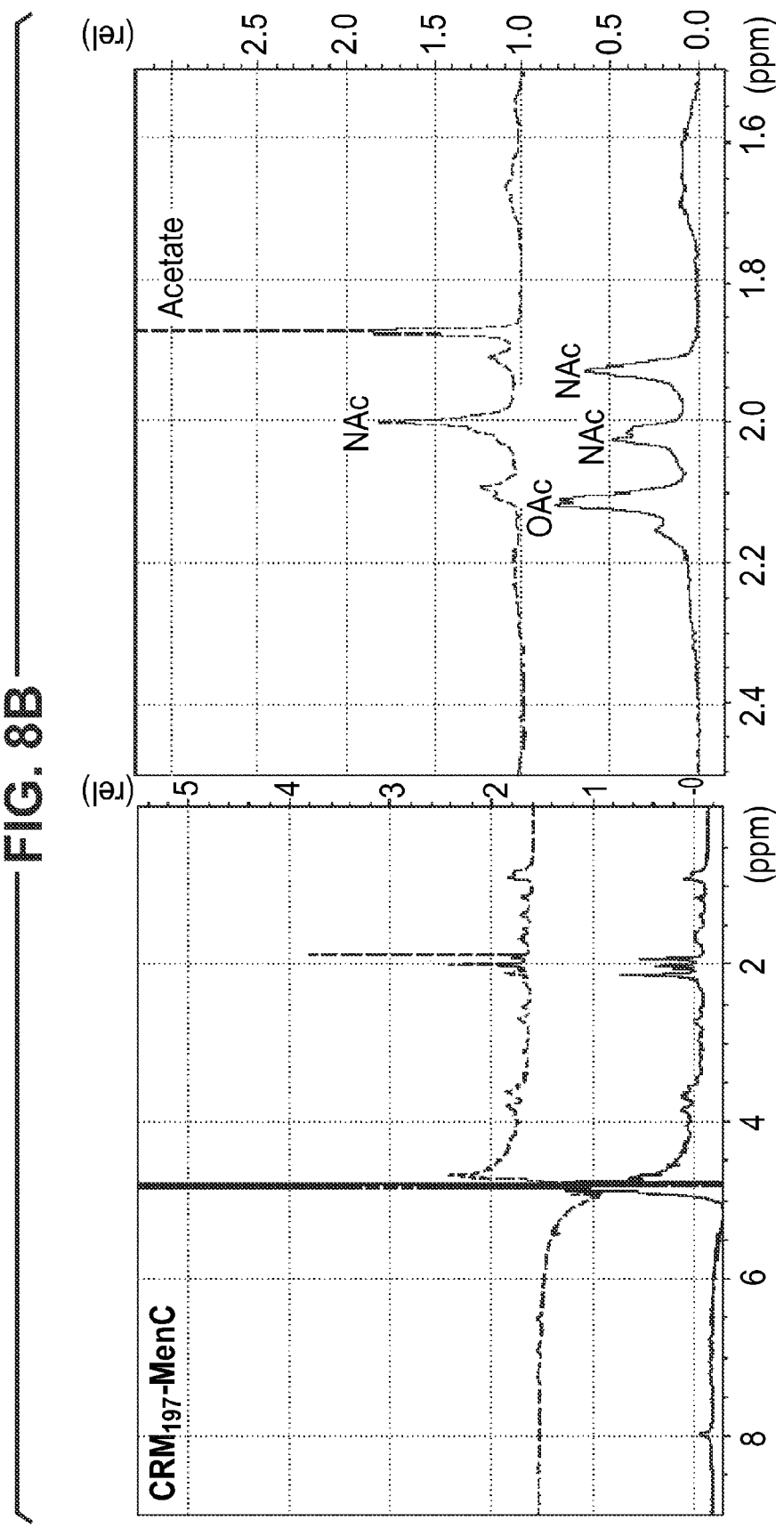
Figure 8C:
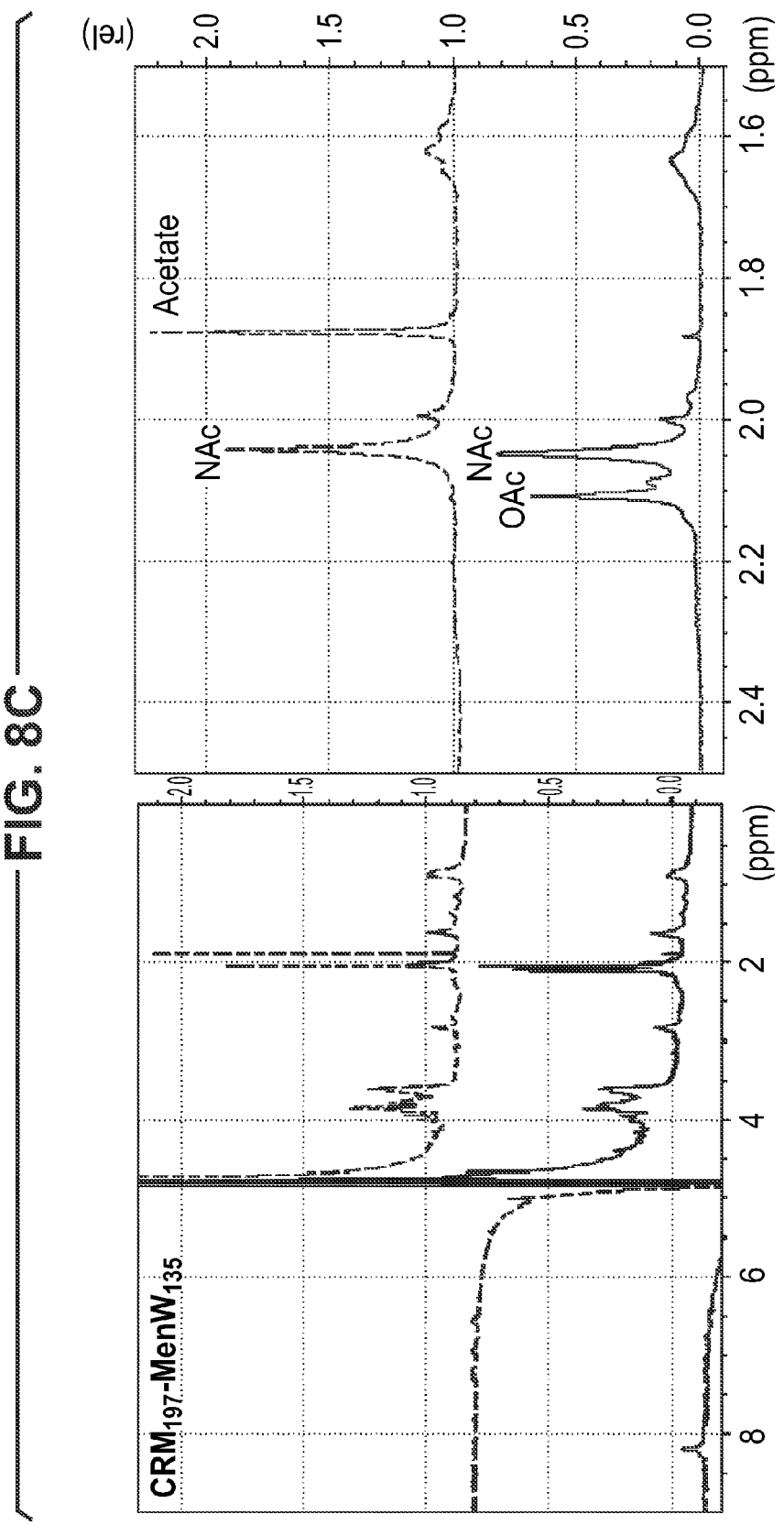
Figure 8D:
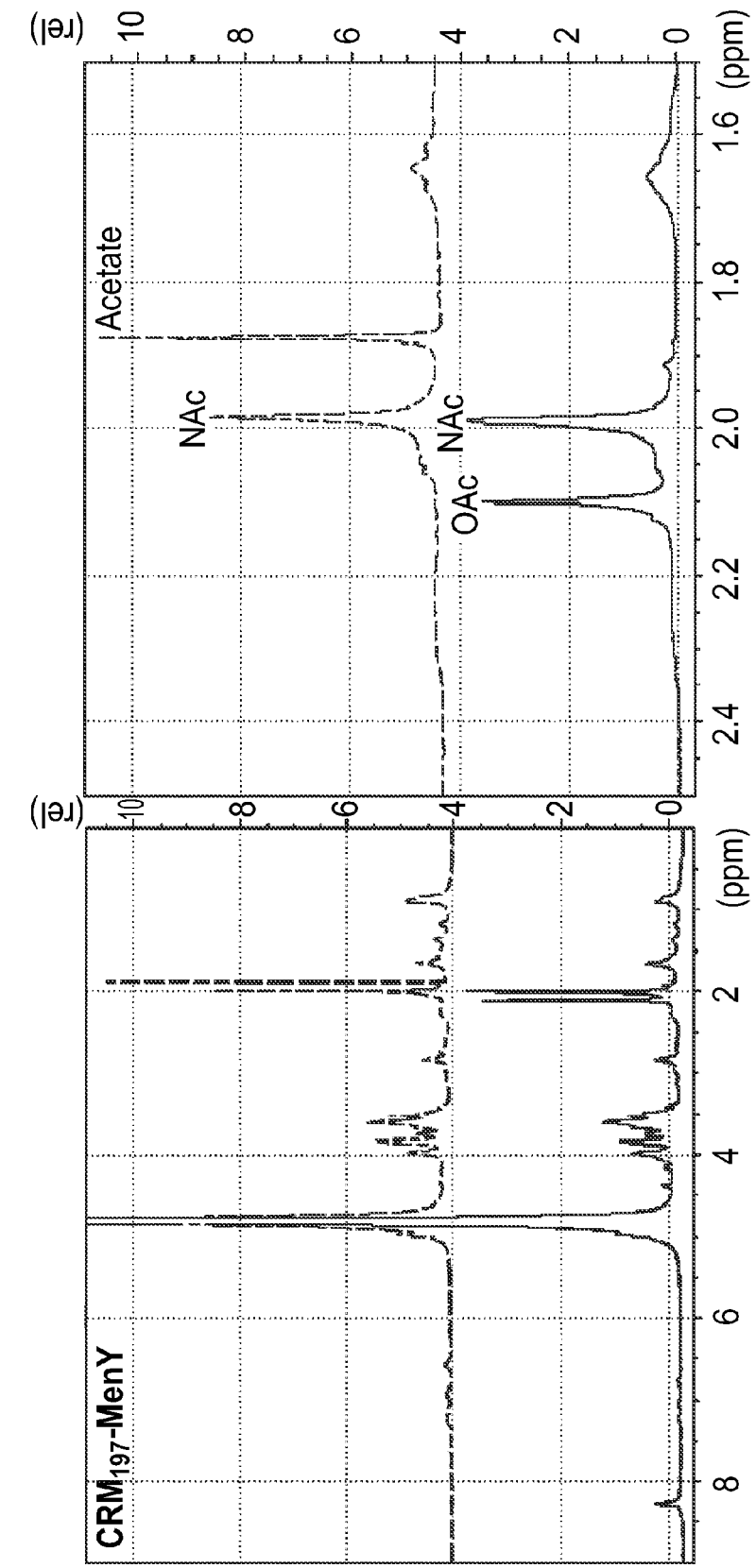

The disclosure provides methods, compositions, and kits for assessing the immunogenicity, potency, or both, of meningococcal capsular polysaccharide vaccines. The disclosed methods, compositions and kits are based upon an assay whereby a bactericidal antibody binding to the polysaccharide of the vaccine can be used as an accurate proxy for the immunogenicity, potency, or both, of the vaccine to avoid testing of vaccine lots for immunogenicity, potency, or both, prior to release or use, for example, by immunizing a control animal. Applicants have appreciated that there is a correlation between the antigenicity of meningococcal capsular polysaccharide vaccines with respect to bactericidal antibodies and the immunogenicity of such vaccines. Applicants have also appreciated that there is a correlation between the antigenicity of meningococcal capsular polysaccharide vaccines with respect to bactericidal antibodies and the potency of such vaccines. The disclosed methods, compositions and kits may be used to assess immunogenicity, potency, or both, to meet governmental regulatory criteria for release of manufacturing lots of vaccine.

Meningococcal Capsular Saccharide Vaccines

The vaccines assayed include capsular saccharides from at least two of serogroups A, C, W135 and Y of *Neisseria meningitidis*. In certain embodiments, such vaccines may further comprise an antigen from one or more of the following: (a) *N. meningitidis*, serogroup B (e.g., an outer membrane vesicle or one or more recombinant polypeptide antigens; (b) *Haemophilus influenzae* type B; (c) *Staphylococcus aureus*, (d) groups A and/or B *streptococcus*, (e) pathogenic *E. coli*, and/or (f) *Streptococcus pneumoniae*.

In certain embodiments the vaccines assayed include capsular saccharides from serogroups C and Y of *N. meningitidis*. In certain embodiments the vaccines assayed include capsular saccharides from serogroups C, W135 and Y of *N. meningitidis*. In certain embodiments the vaccines assayed include capsular saccharides from serogroups A, C, W135 and Y of *N. meningitidis*. In certain embodiments the vaccines assayed include capsular saccharides from *H. influenzae* type B and serogroups C and Y of *N. meningitidis*. In certain embodiments the vaccines assayed include capsular saccharides from *H. influenzae* type B and serogroups C, W135 and Y of *N. meningitidis*. In certain embodiments the vaccines assayed include capsular saccharides from *H. influenzae* type B and serogroups A, C, W135 and Y of *N. meningitidis*. In certain embodiments the vaccines assayed include capsular saccharides from *S. pneumoniae* and serogroups C and Y of *N. meningitidis*. In certain embodiments the vaccines assayed include capsular saccharides from *S. pneumoniae* and serogroups C, W135 and Y of *N. meningitidis*. In certain embodiments the vaccines assayed include capsular saccharides from *S. pneumoniae* and serogroups A, C, W135 and Y of *N. meningitidis*. In certain embodiments the vaccines assayed include capsular saccharides from *H. influenzae* type B, *S. pneumoniae* and serogroups C and Y of *N. meningitidis*. In certain embodiments the vaccines assayed include capsular saccharides from *H. influenzae* type B, *S. pneumoniae* and serogroups C, W135 and Y of *N. meningitidis*. In certain embodiments the vaccines assayed include capsular saccharides from *H. influenzae* type B, *S. pneumoniae* and serogroups A, C, W135 and Y of *N. meningitidis*.

The capsular saccharides of each of these four serogroups of *N. meningitidis* are well characterized. The capsular saccharide of serogroup A meningococcus is a homopolymer of ($\alpha 1 \rightarrow 6$)-linked N-acetyl-D-mannosamine-1-phosphate, with partial O-acetylation in the C3 and C4 positions. The acetyl groups can be replaced with blocking groups to prevent hydrolysis (see, e.g., WO03/080678), and such modified saccharides are still serogroup A capsular saccharides as disclosed herein. The serogroup C capsular saccharide is a homopolymer of ($\alpha 2 \rightarrow 9$)-linked sialic acid (N-acetyl neuraminic acid ("NeuNAc")). Most serogroup C strains have O-acetyl groups at C-7 and/or C-8 of the sialic acid residues, but about 15% of clinical isolates lack these O-acetyl groups. The saccharide structure is written as $\rightarrow 9$)-Neu p NAc 7/8OAc-($\alpha 2 \rightarrow$. The serogroup W135 saccharide is a polymer of sialic acid-galactose disaccharide units. Like the serogroup C saccharide, it has variable O-acetylation, but at sialic acid 7 and 9 positions. The structure is written as: $\rightarrow 4$)-D-Neup5Ac(7/9OAc)-$\alpha$-(2$\rightarrow$6)-D-Gal-$\alpha$-(1$\rightarrow$. The serogroup Y saccharide is similar to the serogroup W135 saccharide, except that the disaccharide repeating unit includes glucose instead of galactose. Like serogroup W135, it has variable O-acetylation at sialic acid 7 and 9 positions.

The serogroup Y structure is written as: $\rightarrow 4$)-D-Neup5Ac(7/9OAc)-$\alpha$-(2$\rightarrow$6)-D-Glc-$\alpha$-(1$\rightarrow$.

The capsular saccharides may be native capsular saccharides obtained from a meningococcal bacteria of the requisite serogroup. The native capsular saccharide may be modified by any method available to one of skill in the art so long as the capsular saccharide retains at least one epitope that elicits serum bactericidal antibodies. Exemplary modifications are detailed below. In addition to native and modified capsular saccharides, the capsular saccharides may be chemically synthesized as long as the as the synthesized compound (saccharide, saccharide analog, etc.) includes at least one epitope that elicits serum bactericidal antibodies that bind to capsular saccharides. All such native, modified and chemically synthesized capsular saccharides are within the scope of the meningococcal capsular saccharides disclosed herein. Exemplary modifications and chemical syntheses are described below.

The capsular saccharides in the vaccines may be O-acetylated as described above (e.g., with the same O-acetylation pattern as seen in native capsular saccharides), or they may be partially or totally de-O-acetylated at one or more positions of the saccharide rings, or they may be hyper-O-acetylated relative to the native capsular saccharides.

The capsular saccharides in the vaccines may be shorter than the native capsular saccharides seen in bacteria. Thus the saccharides may be partially depolymerized, which typically occurs after purification but before conjugation. Depolymerization reduces the chain length of the saccharides. A preferred depolymerization method involves the use of hydrogen peroxide (see, e.g., WO02/058737). Hydrogen peroxide is added to a saccharide (e.g., to give a final $H_2O_2$ concentration of 1%), and the mixture is then incubated (e.g., at about 55° C.) until a desired chain length reduction has been achieved. Another depolymerization method involves acid hydrolysis (see, e.g., WO03/007985). Other depolymerization methods are known to the skilled person. The capsular saccharides used in the vaccines may be obtainable by any of these depolymerization methods. Depolymerization can be used in order to provide an optimum chain length for immunogenicity and/or to reduce chain length for physical manageability of the saccharides. Native capsular saccharides are typically referred to as capsular polysaccharides while depolymerized capsular saccharides are typically referred to as capsular oligosaccharides.

Chemically synthesized capsular saccharides may have the same chemical structure as the native or modified capsular saccharides, but chemical synthesis allows for introduction of alternative chemical structures that can have superior properties. By way of example, meningococcal capsular saccharides from serogroup A can be synthesized to have a phosphonate $\alpha 1 \rightarrow 6$ linkage rather than the native phosphate linkage to improve stability of the capsular saccharides (see, e.g., WO2006/120576).

The vaccines may be formulated to give substantially a 1:1:1:1 ratio (measured as mass of saccharide), e.g., the mass of each serogroup's saccharide is within ±10% of each other, though other ratios will not affect the methods disclosed herein. A typical quantity of meningococcal antigen per serogroup in a composition is between 1 μg and 20 μg, e.g., between 2 and 10 μg per serogroup, or about 4 μg or about 5 μg. As an alternative to a 1:1:1:1 ratio, a double serogroup A dose may be used (2:1:1:1).

Conjugates

One or more of the capsular saccharides in the vaccines may be conjugates. Conjugation is used to enhance the immunogenicity of saccharides. Conjugation converts the immune response from T-independent to T-dependent. This allows priming for immunological memory. Conjugation is particularly useful for pediatric vaccines and is a well known technique.

Typical carrier proteins for use in conjugates are bacterial toxins or toxoids, such as diphtheria toxin (or its $CRM_{197}$ mutant) and tetanus toxin. Other known carrier proteins include the *N. meningitidis* outer membrane protein, synthetic peptides, heat shock proteins, pertussis proteins, cytokines, lymphokines, hormones, growth factors, artificial proteins comprising multiple human $CD4^+$ T cell epitopes from various pathogen-derived antigens, protein D from *H. influenzae*, pneumococcal surface protein PspA, iron-uptake proteins, toxin A or B from *C. difficile*, etc. Covalent conjugation is preferred.

It is possible to use more than one carrier protein in the vaccines assayed. Thus different carrier proteins can be used for different serogroups, e.g., serogroup A saccharides might be conjugated to $CRM_{197}$ while serogroup C saccharides might be conjugated to diphtheria toxoid. It is also possible to use more than one carrier protein for a particular saccharide antigen, e.g., serogroup A saccharides might be in two groups, with some conjugated to $CRM_{197}$ and others conjugated to diphtheria toxoid. In general, however, it is preferred to use the same carrier protein for all meningococcal saccharides in the composition, and more preferably for all saccharides (i.e., including any non-meningococcal conjugates that may be present).

A single carrier protein might carry more than one saccharide antigen (see, e.g., GB 0323103.2). For example, a single carrier protein might have conjugated to it saccharides from serogroups A and C. To achieve this goal, saccharides can be mixed prior to the conjugation reaction. In general, however, it is much more common to have separate conjugates for each serogroup.

Conjugates in the vaccines may have saccharide:protein ratio (w/w) of between 1:15 (i.e., excess protein) and 15:1 (i.e., excess saccharide), between 1:10 and 10:1, or between 1:5 and 5:1. Excess carrier protein is typical, but not necessary for practice of the disclosed method.

Conjugates may be used in conjunction with free carrier protein (see, e.g., (WO96/40242). When a given carrier protein is present in both free and conjugated form in a vaccine, however, the unconjugated form is preferably no more than 5% of the total amount of the carrier protein in the composition as a whole, and more preferably present at less than 2% by weight.

Any suitable conjugation reaction can be used, with any suitable linker where necessary. The saccharide will typically be activated or functionalized prior to conjugation. Activation may involve, for example, cyanylating reagents such as CDAP (e.g., 1-cyano-4-dimethylamino pyridinium tetrafluoroborate). Other suitable techniques use carbodiimides, hydrazides, active esters, norborane, p-nitrobenzoic acid, N-hydroxysuccinimide, S-NHS, EDC, and TSTU.

Linkages via a linker group may be made using any known procedure, for example, the procedures described in U.S. Pat. Nos. 4,882,317 and 4,695,624. One type of linkage involves reductive amination of the polysaccharide, coupling the resulting amino group with one end of an adipic acid linker group, and then coupling a protein to the other end of the adipic acid linker group. Other linkers include B-propionamido, nitrophenyl-ethylamine, haloacyl halides, glycosidic linkages, 6-aminocaproic acid, ADH, $C_4$ to $C_{12}$ moieties, etc. As an alternative to using a linker, direct linkage can be used. Direct linkages to the protein may comprise oxidation of the saccharide followed by reductive amination with the protein, as described in, for example, U.S. Pat. Nos. 4,761,283 and 4,356,170.

Conjugates may be prepared separately and then mixed for use in the vaccine. After mixing, the concentration of the mixed conjugates can be adjusted, e.g., with sterile pyrogen-free, phosphate-buffered saline. The conjugates can be tested for immunogenicity before mixing, after mixing or both.

Further Antigenic Components of the Vaccines

In addition to meningococcal capsular saccharides, the vaccines assayed may include other antigens without conflicting with the disclosed methods and therefore such vaccines shall still be meningococcal capsular saccharide vaccines as disclosed herein. By way of example, the meningococcal capsular saccharide vaccines may include any of the following antigens:

1. A Capsular Saccharide from *S. pneumoniae*.

The capsular saccharides may include saccharides from more than one serotype of *S. pneumoniae*. For example, mixtures of polysaccharides from 23 different serotypes are widely used, as are conjugate vaccines with polysaccharides from between 5 and 11 different serotypes (see, e.g., Zielen et al. (2000) *Infect. Immun.* 68:1435-1440). For example, PrevNar™ contains antigens from seven serotypes (4, 6B, 9V, 14, 18C, 19F, and 23F) with each saccharide individually conjugated to $CRM_{197}$ by reductive amination, with 2 μg of each saccharide per 0.5 ml dose (4 μg of serotype 6B), and with conjugates adsorbed on an aluminum phosphate adjuvant. Where pneumococcal conjugates are included in a vaccine to be assayed, the composition preferably includes at least serotypes 6B, 14, 19F and 23F.

2. A Capsular Saccharide from *H. influenzae* B (Hib).

The capsular saccharides may be unconjugated or conjugated. The carrier protein for the conjugate may be, for example, $CRM_{197}$, Dt, a tetanus toxoid or an outer membrane complex of *N. meningitidis*. The saccharide moiety of the conjugate may be a polysaccharide (e.g., full-length polyribosylribitol phosphate (PRP)), but it is typical to depolymerize the capsular polysaccharides to form oligosaccharides. A preferred Hib conjugate comprises an oligosaccharide covalently linked to $CRM_{197}$ via an adipic acid linker 3. A Protein Antigen from *Neisseria meningitidis* Serogroup B (See, e.g., WO2004/032958).

The composition may comprise one or more of these further antigens. Such antigens may or may not be adsorbed to an aluminum salt.

The Vaccine Composition

The meningococcal capsular saccharide vaccines assayed as disclosed herein will typically include a pharmaceutically acceptable carrier. Such carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. Typically the carriers and diluents will not affect the practice of the methods disclosed herein. However, if a carrier or a diluent would interfere with a preferred assay, the capsular saccharide to be assayed can be separated from the carrier or diluent prior to the step of the assay that would be adversely affected.

The vaccines may include an antimicrobial, particularly if packaged in a multiple dose format.

The vaccines may comprise detergent, e.g., a TWEEN™ (polysorbate), such as TWEEN 80™. Detergents are generally present at low levels, e.g., <0.01%.

The vaccines may include sodium salts (e.g., sodium chloride and/or sodium phosphate). These can be used for tonicity. A concentration of 10±2 mg/ml NaCl is typical, e.g., about 8.8 mg/ml. A concentration of 1.2 mg/ml sodium phosphate is typical.

The vaccines will generally include a buffer, e.g., a phosphate buffer.

The vaccines may comprise a sugar alcohol (e.g., mannitol) or a disaccharide (e.g., sucrose or trehalose), which may comprise about 15-30 mg/ml (e.g., 25 mg/ml), particularly if they are to be lyophilized or if they include material which has been reconstituted from lyophilized material. Typical vaccines, however, will not be lyophilized, i.e., all meningococcal capsular saccharides are present in aqueous form, from the packaging stage to the administration stage. However, in certain embodiments, one or more of the capsular saccharides may be lyophilized while the remaining capsular saccharides are in liquid form, e.g., the serogroup A capsular saccharide is lyophilized while the serogroups C, W135, and Y capsular saccharides are in liquid form. In such case the assay may be performed on the liquid component(s) and the separately reconstituted lyophilized component(s) or the assay may be performed on the combined vaccine where the lyophilized component(s) are reconstituted with the liquid component(s).

The vaccines will be formulated for administration directly to a patient. Direct delivery formulations may be for parenteral injection (e.g., subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration (e.g., to the thigh or the upper arm) is preferred. Injection may be via a needle (e.g., a hypodermic needle), but needle-free injection may alternatively be used. A typical intramuscular dose is 0.5 ml.

Meningococcal capsular saccharides from multiple serogroups are administered in admixture within a single composition. The vaccines may be administered as a single dose, or may be administered more than once in a multiple dose schedule. Multiple doses may be used in a primary immunization schedule and/or in a booster immunization schedule. A primary dose schedule may be followed by a booster dose schedule of the meningococcal capsular saccharides. Suitable timing between priming doses (e.g., between 4-16 weeks), and between priming and boosting, can be routinely determined. The vaccines may conveniently be administered at the same time as other vaccines, e.g., at the same time as a D-T-P vaccine, or at the same time as a pneumococcal conjugate vaccine, or at the same time as an influenza vaccine, or at the same time as a MMR or MMRV vaccine. These vaccines will generally be administered separately but during the same visit to the doctor.

Bacterial infections can affect various areas of the body and so the vaccines may be prepared in various forms. For example, the vaccines may be prepared as injectables, either as liquid solutions or suspensions. Solid forms suitable for solution in, or suspension in, liquid vehicles prior to injection can also be prepared (e.g., a lyophilized composition). The vaccines may be prepared for topical administration, e.g., as an ointment, cream or powder. The vaccines be prepared for oral administration, e.g., as a tablet or capsule, or as a syrup (optionally flavored). The vaccines may be prepared for pulmonary administration, e.g., as an inhaler, using a fine powder or a spray. The vaccines may be prepared as a suppository or pessary. The vaccines may be prepared for nasal, aural or ocular administration, e.g., as spray, drops, gel or powder. In general, however, the meningococcal capsular saccharide vaccines are formulated for intramuscular injection. One of skill in the art would recognized that certain of the foregoing vaccine formulations would need to be tested prior to formulation and/or after formulation where the vaccine is processed to a liquid form suitable for use in the assays, e.g., lyophilized forms will be reconstituted with liquid; tablets, capsules, powders, and suppositories dissolved in a suitable liquid, etc.

The meningococcal capsular saccharide vaccines may optionally include an adjuvant such as alum and/or MF59™. One of skill in the art can readily determine whether an adjuvant would interfere with the practice of the methods disclosed herein and can easily pre-process the vaccine sample to remove the adjuvant or otherwise prevent the adjuvant from interfering, e.g., the capsular saccharide can be "desorbed" from aluminum phosphate prior to applying the methods disclosed herein.

Bactericidal Antibodies

The antibodies used in the compositions, methods and kits disclosed herein may be obtained from any source so long as the antibody binds to the capsular saccharide in the vaccine for which immunogenicity, potency, or both, needs to be assessed and is bactericidal or binds to the same epitope as a bactericidal antibody. Preferably, the bactericidal antibodies are IgG antibodies. For the purposes of this disclosure, bactericidal antibodies include any antibody that binds to an epitope bound by bactericidal antibodies. Therefore, bactericidal antibodies include natural and synthetic antibodies (e.g., engineered antibodies such as chimeric antibodies, humanized antibodies, CDR-grafted antibodies, veneered antibodies, phage-display isolated antibodies, minibodies, other engineered scaffold proteins, etc.). Preferably, the bactericidal antibodies will not cross-react (i.e., they will only bind to the capsular saccharide of interest and not bind to capsular saccharides of from other serogroups in the vaccine). One of skill in the art can readily screen for bactericidal antibodies do not cross react (see, e.g., Example 2, "Specificity," below). Monoclonal antibodies are preferred, but polyclonal antibodies may be used in the practice of the disclosed methods. One of skill in the art could readily remove cross-reacting antibodies in a polyclonal antibody sample including, by way of example, by running the polyclonal antibody sample through a chromatograph column with immobilized capsular saccharides from the other serogroups in the vaccine.

One of skill in the art would understand that the capsular saccharide of interest in any form may be used to generate bactericidal antibodies that may be used in the invention disclosed herein. Any method that can be used to generate antibodies may be used, such as immunization of an animal with a humoral immune system, antibody phage display screened against the capsular saccharide of interest, etc. By way of example, capsular polysaccharides, capsular oligosaccharides and conjugates of either may be used (and the vaccine itself or individual capsular saccharide components thereof if the vaccine has two or more antigens and polyclonal antibodies are to be used). In certain embodiments, the bactericidal antibody may be in the form of an antibody containing serum sample, polyclonal antibodies, antigen-purified polyclonal antibodies or monoclonal antibodies. The bactericidal antibody preferably binds to a specific capsular saccharide in the vaccine of interest and to the optional control saccharide if used.

Control Saccharide

When the compositions, methods and kits disclosed herein measure binding by a competition assay, a control saccharide will be used that will compete with the vaccine for binding to the bactericidal antibody. One of skill in the art can readily select the form of control saccharide, which can include any of the forms discussed above in the section titled "Meningococcal Capsular Saccharide Vaccines."

Assessing Binding of the Bactericidal Antibody to the Vaccine

Any method that can quantitatively measure the binding of the bactericidal antibody to the vaccine may be used with the compositions, methods and kits disclosed herein. The methods can directly measure binding such as in a sandwich assay or indirectly measure binding by measuring binding of the bactericidal antibody to a control saccharide in the presence of the vaccine (as a competitor).

In certain embodiments, the binding measurement to the vaccine will be compared to a standard of a known concentration such as a reference lot of a vaccine or purified capsular polysaccharide. Such comparison may be performed by plotting the results for the reference and standard curves on a graph. The relative positions of the curves can be used to determine the immunogenicity, potency, or both, of the test vaccine.

The measurements will typically be taken by detection of a label such as a radioisotope, a fluorophores or an enzyme (e.g., alkaline phosphatase or horseradish peroxidase). The label may be applied to a number of components of the assay such as the bactericidal antibody, the antigen being measured or a secondary antibody that binds to the bactericidal antibody or to the antigen. Exemplary methods are described below.

ELISA (Enzyme-Linked ImmunoSorbent Assay). ELISA involves at least one bactericidal antibody that binds to a specific meningococcal capsular saccharide in the vaccine of interest. The test vaccine (direct measurement) or the control saccharide (indirect competition measurement) may be immobilized on a solid support (such as multiwell plate) either non-specifically (via adsorption to the surface) or specifically (via capture by the bactericidal antibody specific to the capsular saccharide of interest, in a "sandwich" ELISA). After the capsular saccharide component of the test vaccine has been immobilized, a secondary antibody for detection may be added which binds to the capsular saccharide component (e.g., to the capsular saccharide or to a carrier protein of a capsular saccharide conjugate component) or to the bactericidal antibody depending upon the assay. The label to be detected may be bound to the secondary antibody or may be bound to a tertiary antibody that binds to the secondary antibody.

Immunoprecipitation. Immunoprecipitation involves precipitating the capsular polysaccharide interest in the vaccine out of solution using a bactericidal antibody. The immunoprecipitated complexes can be measured by any number of analytical techniques available to one of skill in the art. The bactericidal antibody:capsular saccharide complexes may be brought out of solution by insoluble antibody-binding proteins such as protein A or protein G. As an alternative to precipitation, the insoluble antibody-binding proteins may be coupled to beads.

Dot Blotting. Dot blotting may be used to measure capsular saccharide conjugates in a test vaccine. The test vaccine is applied to a membrane (such as nitrocellulose or PVDF). The bactericidal antibody is allowed to bind to the capsular saccharide and is then detected.

Radioimmunoassay. Radioimmunoassays may be used in measuring binding of the bactericidal antibody to the vaccine. In one embodiment, vaccine is mixed with a known quantity of radiolabeled capsular saccharide (such as the control saccharide) and the bactericidal antibody. The unlabeled vaccine will compete with the radiolabeled capsular saccharide allowing measuring of the binding and thereby assessing the immunogenicity, potency, or both, of the vaccine.

Other methods that can be used include cytometric bead assay, Luminex assay, Western blot, agglutination, nephelometry, turbidimetry, and others.

Kits

The methods and compositions disclosed herein may be embodied in a kit for the practice of the assays. Exemplary kits will include a multiwell plate for serial dilutions, at least two control saccharide to bind to the surface of the wells corresponding to the serogroup of the meningococcal capsular saccharide to be assayed, and at least two bactericidal antibodies, each of which binds to one of the control saccharides and one of the at least two the serogroup of the meningococcal capsular saccharide to be assayed. The kits may also include a bactericidal antibody dilution buffer, which may include a reagent that stabilized the bactericidal antibody over time to prevent heterogeneity. Exemplary reagents are detergents such as TWEEN 20™. The kits may also include a vaccine dilution buffer. In certain embodiments, the control saccharides may be: native capsular polysaccharides from the serogroups to be assayed, capsular oligosaccharides from the serogroups to be assayed, synthetic saccharides from the serogroups to be assayed, or conjugates of any of the preceding. The bactericidal antibodies in the kit may be formulated for storage at −20° C. in a buffer that includes a serum albumin protein.

General

The term "comprising" encompasses "including" as well as "consisting", e.g., a composition "comprising" X may consist exclusively of X or may include something additional, e.g., X+Y.

The word "substantially" does not exclude "completely", e.g., a composition which is "substantially free" from Y may be completely free from Y. Where necessary, the word "substantially" may be omitted from the definition of the invention. The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a cell substrate is used for reassortment or reverse genetics procedures, it is preferably one that has been approved for use in human vaccine production, e.g., as in Ph Eur general chapter 5.2.3.

Identity between polypeptide sequences is preferably determined by the Smith-Waterman homology search algorithm as implemented in the MPSRCH program (Oxford Molecular), using an affine gap search with parameters gap open penalty=12 and gap extension penalty=1.

EXAMPLES

Example 1

Optimization of the ELISA Method for the Antigenicity of a Tetravalent *N. meningitidis* ACWY Capsular Saccharide Conjugate Vaccine This Example 1 describes experiments conducted to determine conditions and parameters for an in vitro antibody binding assay that can be used to measure the immunogenicity and potency of capsular polysaccharide vaccines comprising *N. meningitidis* ACWY capsular saccharides. Briefly, the assay monitors changes in the antigenicity of such vaccines that may occur during the manufacturing or conjugation processes. The principle of the assay is a competitive ELISA, in which the vaccine competitively inhibits binding of a bactericidal serogroup-specific antibody to a native capsular polysaccharide or surrogate therefore.

In one form, the reference capsular saccharide is immobilized to an ELISA microtiter plate. The test vaccine is added to the ELISA to compete with the immobilized reference capsular saccharide binding to the bactericidal serogroup-specific antibody. The antigenic properties of the test vaccine can be measured by the comparison with a standard lot of proven immunogenicity and potency in humans.

Basic Antibody Binding Assay Procedure.

The bactericidal monoclonal antibodies (mAbs) Anti-A, Anti-C, Anti-W and Anti-Y were analyzed in an ELISA assay, modified from a method designed for specific determination of IgG antibody responses in mice sera. Microtiter plates were coated with the capsular polysaccharide at a final concentration of 2.0 µg/ml, in PBS pH 7.4. Plates were sealed, incubated overnight at 2-8° C., then washed and saturated with a PBS pH 7.4 solution containing 1% porcine gelatin, as blocking reagent, for two hours incubation at 37° C. Then plates were fixed with a saline solution, containing 4% Polyvinyl-pyrrolidone (Serva) and 10% sucrose, and incubated at room temperature for two hours; after the incubation, the fixing solution was aspirated and the plates were left overnight on the bench to dry.

In a separate polypropylene microtiter plate (NUNC), specific competitors (the native polysaccharides, oligosaccharides-CRM conjugates or a tetravalent ACWY conjugate vaccine) were diluted with buffer solution (1% Bovine Serum Albumin in PBS pH 7.4+0.01% TWEEN 20™) with three-fold or five-fold dilution steps, depending on the antigen (see Table 1). Then, the same volume of mAbs, at a fixed dilution, was added into the wells and allowed to interact directly with the competitor at room temperature. After this step the mixture was transferred to the coated and saturated plates and incubated for two hours at 37° C. Plates were then washed and a goat anti-mouse IgG antibody conjugated to Alkaline Phosphatase was diluted 1:1500 in the dilution buffer and added to the plates. The secondary antibody was incubated for 1.5 hours at 37° C. and, after washing, plates were left for 30 min at room temperature with a chromogenic substrate solution (1 mg/ml p-Nitro Phenyl Phosphate from Sigma). The absorbance values were read at a wavelength of 405-620 nm.

The monoclonal antibodies Anti-A, Anti-C, Anti-W and Anti-Y were each bactericidal antibodies specifically directed against one of the four A, C, W135 and Y meningococcal capsular saccharides, A, C, W135 and Y, respectively.

TABLE 1

Plate layout for MenA and MenC antigens (columns 1 and 12, rows A and H = blank; row B = mAb Anti-A or Anti-C, at fixed dilution, without any competitor; rows C-G = mAb Anti-A or Anti-C, at fixed dilution, added with the competitor (the native polysaccharide or oligosaccharide-CRM conjugate or a tetravalent ACWY conjugate vaccine) at 10 three- (mAb Anti-C) or five-fold (mAb Anti-A) dilutions, starting from 10000 ng/ml (MenA) or 5000 ng/ml (MenC, MenW135 and MenY).

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   | 10000 | 10000 | 10000 | 10000 | 10000 | 10000 | 10000 | 10000 | 10000 | 10000 |   |
| C |   | 10000 | 2000 | 400 | 80 | 16 | 3.2 | 0.64 | 0.128 | 0.26 | 0.0051 |   |
| D |   | 10000 | 2000 | 400 | 80 | 16 | 3.2 | 0.64 | 0.128 | 0.26 | 0.0051 |   |
| E |   | 10000 | 2000 | 400 | 80 | 16 | 3.2 | 0.64 | 0.128 | 0.26 | 0.0051 |   |
| F |   | 10000 | 2000 | 400 | 80 | 16 | 3.2 | 0.64 | 0.128 | 0.26 | 0.0051 |   |
| G |   | 10000 | 2000 | 400 | 80 | 16 | 3.2 | 0.64 | 0.128 | 0.26 | 0.0051 |   |
| H |   |   |   |   |   |   |   |   |   |    |    |    |

TABLE 1-continued

Plate layout for MenA and MenC antigens (columns 1 and 12, rows A and H = blank; row B = mAb Anti-A or Anti-C, at fixed dilution, without any competitor; rows C-G = mAb Anti-A or Anti-C, at fixed dilution, added with the competitor (the native polysaccharide or oligosaccharide-CRM conjugate or a tetravalent ACWY conjugate vaccine) at 10 three- (mAb Anti-C) or five-fold (mAb Anti-A) dilutions, starting from 10000 ng/ml (MenA) or 5000 ng/ml (MenC, MenW135 and MenY).

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   | 10000 | 10000 | 10000 | 10000 | 10000 | 10000 | 10000 | 10000 | 10000 | 10000 |   |
| C |   | 5000 | 1667 | 556 | 185 | 62 | 21 | 7 | 2.3 | 0.8 | 0.3 |   |
| D |   | 5000 | 1667 | 556 | 185 | 62 | 21 | 7 | 2.3 | 0.8 | 0.3 |   |
| E |   | 5000 | 1667 | 556 | 185 | 62 | 21 | 7 | 2.3 | 0.8 | 0.3 |   |
| F |   | 5000 | 1667 | 556 | 185 | 62 | 21 | 7 | 2.3 | 0.8 | 0.3 |   |
| G |   | 5000 | 1667 | 556 | 185 | 62 | 21 | 7 | 2.3 | 0.8 | 0.3 |   |
| H |   |   |   |   |   |   |   |   |   |    |    |    |

Assay Optimization

Saccharide Coating:

We compared plates coated with the native polysaccharides with plates coated with oligosaccharide-CRM conjugates. We compared the inhibition curves of the monoclonal antibodies using two different competitors: a negative control for which less competition was expected, and a reference from a Menveo vaccine lot that had been tested in clinical trials. The experiment was carried out using two plates for each antigen: one coated with the native polysaccharide (PS) and one coated with the oligosaccharide-CRM conjugate. The final mAbs dilution in plates coated with native PS was:

anti-A 1:10000
anti-C 1:40000
anti-W 1:250
anti-Y 1:800

The final mAbs dilution in plates coated with oligosaccharide-CRM was:

anti-A 1:40000
anti-C 1:160000
anti-W 1:1000
anti-Y 1:10000

The competitors were diluted with a 5-fold (MenA) or 3-fold (MenC, MenW135, MenY) step dilution, starting from the same concentration both for the reference vaccine and the negative control: 10 μg/ml for MenA and 5 μg/ml for MenCWY. As shown in FIGS. 1A-1H, each coating produced a comparable trend for the MenA, MenW135 and MenY curves, whereas the oligosaccharide-CRM conjugate coating showed partial inhibition for the MenC curve, even at the highest competitor concentration. Therefore, further optimization experiments in these Examples used plates coated with the native polysaccharides for all four antigens.

Secondary Antibody (Ab II):

In this experiment, we compared the signal strength from two kinds of secondary antibodies: alkaline phosphatase conjugate (AP) and horseradish peroxidase conjugate (HRP). The secondary antibodies were tested by analyzing the monoclonal antibodies at a fixed dilution (Anti-A 1:10000; Anti-C 1:10000; Anti-W 1:2000; and Anti-Y 1:200), without adding any competitor.

The mean optical density and variance coefficient for each plate are shown in Table 2, below. The two secondary antibody conjugates produced essentially identical results except that the Anti-Y plate using the HRP secondary antibody showed a CV% significantly lower than the Anti-Y plate using the AP secondary antibody. However, since the results obtained with the AP secondary antibody were acceptable for the four antigens, this secondary antibody was selected for the experiments that follow.

TABLE 2

Mean OD and CV % across the plate for the two secondary antibodies.

|   | Mean | DS | CV % |
|---|---|---|---|
| Anti-MenA Ab + AP secondary Ab | 1428 | 196 | 14 |
| Anti-MenA Ab + HRP secondary Ab | 1273 | 125 | 10 |
| Anti-MenC Ab + AP secondary Ab | 1346 | 201 | 15 |
| Anti-MenC Ab + HRP secondary Ab | 1179 | 145 | 12 |
| Anti-MenW Ab + AP secondary Ab | 1214 | 136 | 11 |
| Anti-MenW Ab + HRP secondary Ab | 882 | 111 | 13 |
| Anti-MenY Ab + AP secondary Ab | 1182 | 194 | 16 |
| Anti-MenY Ab + HRP secondary Ab | 1473 | 73 | 5 |

Monoclonal and Secondary Antibody Dilution Buffers:

In order to select the most appropriate dilution buffer in which to dilute the anti-capsular saccharide antibodies and the secondary antibody, four different buffers were tested. Monoclonal antibodies without competitors were diluted with four buffers and tested in the same plate (one row for blank, three rows each for the mAb diluted in one of the four buffers).

Buffer 1: PBS 1×+0.01% TWEEN 20™+1% BSA

Buffer 2: PBS 0.5×+0.05% TWEEN 20™+1% BSA

Buffer 3: PBS 1×+0.05% TWEEN 20™

Buffer 4: PBS 1×+0.01% TWEEN 20™+0.5% BSA

The four buffers produced similar results (See Table 3). Since buffer 1 was already in use, buffer 1 was used in the experiments that follow.

TABLE 3

Comparison of four different buffers

|  | Mean | DS | CV % |
|---|---|---|---|
| Anti-MenA Buffer 1 | 1480 | 209 | 14 |
| Anti-MenA Buffer 2 | 884 | 101 | 11 |
| Anti-MenA Buffer 3 | 1380 | 212 | 15 |
| Anti-MenA Buffer 4 | 1099 | 221 | 20 |
| Anti-MenC Buffer 1 | 666 | 41 | 6 |
| Anti-MenC Buffer 2 | 306 | 20 | 7 |
| Anti-MenC Buffer 3 | 570 | 47 | 8 |
| Anti-MenC Buffer 4 | 541 | 69 | 13 |
| Anti-MenW Buffer 1 | 746 | 63 | 8 |
| Anti-MenW Buffer 2 | 737 | 64 | 9 |
| Anti-MenW Buffer 3 | 576 | 86 | 15 |
| Anti-MenW Buffer 4 | 427 | 61 | 14 |
| Anti-MenY Buffer 1 | 640 | 57 | 9 |
| Anti-MenY Buffer 2 | 594 | 36 | 6 |
| Anti-MenY Buffer 3 | 659 | 53 | 8 |
| Anti-MenY Buffer 4 | 651 | 52 | 8 |

Stability of Pre-Diluted Antibodies.

To verify whether the anti-capsular saccharide antibodies were stable at 2-8° C. after dilution with the dilution buffer, a diluted solution of each primary antibody was prepared using two different buffers (buffer 1: PBS 1×+0.01% TWEEN 20™+1% BSA; buffer 2: PBS 1×). The primary antibodies were diluted in both buffers as follow:

anti-A: 1:5000 (final in plate 1:10000)
anti-C: 1:10000 (final in plate 1:20000)
anti-W: 1:125 (final in plate 1:250)
anti-Y: 1:400 (final in plate 1:800)

The primary antibodies preparations were analyzed, for each antigen, at day 1, day 2 and day 3, by competing with Menveo vaccine and a negative control. Buffer 2 proved to be unsuitable for MenA and MenC as the primary antibodies appeared to have disappeared by the end of the second day. No differences between the two tested buffers were observed for MenW 135 and MenY over the three days tested, indicating that these diluted mAbs are stable at 2-8° C. up to 3 days.

Evaluation of the mAbs Stability Stored at −20° C.

To evaluate a potential source of experimental variability, we verified the protein concentration of a subset of monoclonal aliquots by using the BCA test. This revealed heterogeneity in the protein content of the aliquots stored at −20° C., in buffered saline solution. To reduce this heterogeneity the mAbs were prediluted in PBS 1×+1% BSA at different protein concentration, depending on the antigen (anti-A 1:1000; anti-C 1:1000; anti-W 1:20; anti-Y 1:50). These preparations were divided in 1 ml aliquots and stored at −20° C.

The protein concentration of each mAb preparation was tested in a random subset of samples. mAb aliquots were thawed just before their use and further diluted to the working dilution (1:5 for anti-A, anti-C and anti-W and 1:8 for anti-Y). Each aliquot was used only one time. After thawing and dilution and addition of the competitor, the mAb dilution in the plate was as follows:

anti-A: 1:10000
anti-C: 1:10000
anti-W: 1:200
anti-Y: 1:800

For the experiments that follow, if not expressly stated otherwise, the mAbs were used in the experiments at these concentrations and dilutions.

Evaluation of Coating Stability.

In order to verify the stability of coated plates after their preparation, two experiments were carried out:

Day 2: the first day plates are ready to be used after preparation (corresponds to day 0 for coating stability evaluation)

Day 8: six days after plate coating and saturation.

At day 2, two plates/antigen were tested such that each plate was used to generate six inhibition curves for analysis: three by competing mAbs with the Menveo vaccine Reference lots and three with the Menveo vaccine test lots.

At day 8 one plate/antigen was analyzed, with the same plate scheme described above.

mAbs aliquots used in the experiments were prediluted as described above. Menveo vaccine was diluted, after reconstitution, with 5-fold dilution steps for MenA and 3-fold dilution steps for MenC, MenW135 and MenY. The results showed a significant difference between the two sets of plates in the MenA response curves generated. The response curves for MenC, MenW 135, MenY showed no relevant differences between freshly prepared plates and plates stored at 4° C. for 6 days.

Negative Controls.

In order to verify the sensitivity of the method, negative controls which would show less competition for binding to the mAbs were prepared and tested. The Menveo vaccine lot tested and demonstrated to be immunogenic and potent in humans was used as a reference sample.

In each plate both the vaccine and the negative control were run in triplicate, with step dilution 1:5 for MenA and 1:3 for MenC, MenW135, MenY. mAbs were tested at a fixed dilution, as described above.

The inhibition curves obtained with the negative controls presented a different trend in comparison with the reference sample. The negative controls, as expected had a clearly lower inhibition activity (See, e.g., FIGS. 6A-6D). The analysis of the curves indicated that the negative control curves and the Menveo vaccine reference lot curves show wide separation for the undiluted samples and early dilution steps, whereas the curves converge at higher dilution (i.e., no inhibition).

Robustness—Coating Homogeneity.

Six plates/antigen (same coating preparation) were analyzed for each antigen. The 96 wells of each plate were filled with 100 µl of the same solution (different for each antigen). The solutions consisted of the mAb at the fixed dilution above and the Menveo vaccine reference lot at a selected concentration. The vaccine concentration was chosen, for each mAb, in the middle part of the linear region of the inhibition curves.

The vaccine was diluted at the following concentrations, depending on the antigen:

MenA: 6 ng/ml (final concentration in plate: 3 ng/ml)
MenC: 124 ng/ml (final concentration in plate: 62 ng/ml)
MenW: 1112 ng/ml (final concentration in plate: 556 ng/ml)
MenY: 370 ng/ml (final concentration in plate: 185 ng/ml)

Results (mean ODs and CV%) are shown in Table 4. As indicated by the determined CV% values, tested conditions didn't yield significant differences in responses.

TABLE 4

|  | Mean | DS | CV % |
|---|---|---|---|
| Anti-MenA Plate 1 | 1336 | 106 | 7.9 |
| Anti-MenA Plate 2 | 1566 | 167 | 10.7 |
| Anti-MenA Plate 3 | 1288 | 142 | 11.0 |
| Anti-MenA Plate 4 | 1435 | 151 | 10.5 |
| Anti-MenA Plate 5 | 1260 | 165 | 13.1 |
| Anti-MenA Plate 6 | 1434 | 125 | 8.7 |
| Anti-MenA - Overall | 1386 | 177 | 12.8 |
| Anti-MenC Plate 1 | 1274 | 103 | 8.1 |

TABLE 4-continued

|  | Mean | DS | CV % |
|---|---|---|---|
| Anti-MenC Plate 2 | 1255 | 131 | 10.5 |
| Anti-MenC Plate 3 | 1287 | 91 | 7.1 |
| Anti-MenC Plate 4 | 1579 | 110 | 6.9 |
| Anti-MenC Plate 5 | 1338 | 87 | 6.5 |
| Anti-MenC Plate 6 | 1439 | 81 | 5.6 |
| Anti-MenC - Overall | 1362 | 153 | 11.2 |
| Anti-MenW Plate 1 | 934 | 105 | 11.2 |
| Anti-MenW Plate 2 | 898 | 81 | 9.0 |
| Anti-MenW Plate 3 | 884 | 86 | 9.7 |
| Anti-MenW Plate 4 | 854 | 86 | 10.0 |
| Anti-MenW Plate 5 | 848 | 78 | 9.2 |
| Anti-MenW Plate 6 | 1033 | 76 | 7.3 |
| Anti-MenW - Overall | 908 | 106 | 11.7 |
| Anti-MenY Plate 1 | 663 | 73 | 11.6 |
| Anti-MenY Plate 2 | 785 | 53 | 6.7 |
| Anti-MenY Plate 3 | 701 | 72 | 10.2 |
| Anti-MenY Plate 4 | 795 | 90 | 11.3 |
| Anti-MenY Plate 5 | 795 | 79 | 10.0 |
| Anti-MenY Plate 6 | 799 | 74 | 9.3 |
| Anti-MenY Plate - Overall | 751 | 97 | 12.9 |

Robustness—Incubation times. Three conditions were tested (see Table 5)

TABLE 5

Three different conditions tested.

|  | Incubation Time 1 | Incubation Time 2 | Incubation Time 3 |
|---|---|---|---|
| Ab I (mAb + Menveo) | 1 hour 50 minutes | 2 hours | 2 hours 10 minutes |
| Ab II | 1 hour 20 minutes | 1 hour 30 minutes | 1 hour 40 minutes |
| Development | 27 minutes | 30 minutes | 33 minutes |

Incubation time 2 corresponds to the normal incubation periods applied previously. For each condition, one plate/antigen was tested; in each plate, three inhibition curves were analyzed by competing the mAbs with the Menveo vaccine Reference lot. mAbs aliquots used in the experiments were prediluted as described above. Menveo vaccine was diluted, after reconstitution, with 5-fold dilutions for MenA and 3-fold dilutions for MenC, MenW135 and MenY.

The results showed no relevant differences among tested incubation times.

Robustness—Coating Concentrations.

Three coating concentrations for each native polysaccharide were tested:

1-1 µg/ml
2-2 µg/ml
3-5 µg/ml

For each concentration, four plates/antigen (named plate a, b, c and d) were tested. For each antigen, plates a and b were tested on the first day and plates c and d were tested on the second day. In each plate six inhibition curves were analyzed by competing the mAbs with the Menveo vaccine Reference lot. mAbs aliquots were used prediluted as described above. Menveo vaccine was diluted, after reconstitution, with 5-fold dilution steps for MenA and 3-fold dilution steps for MenC, MenW135 and MenY.

The results showed no relevant differences among tested concentrations.

Reproducibility.

For reproducibility experiments, the experimental scheme was as follow:

2 operators 2 plates/antigen/operator 3 days, 1 experiment/operator/day

In each plate, six inhibition curves were analyzed: three by competing the mAbs with the Menveo vaccine Reference lot and three with the Menveo vaccine test lot. The test lot is comparable to the Reference lot since it was produced by the same process and proved to be immunogenic and potent in clinical trials to a similar degree as the Reference lot.

During the second and the third day, four inhibition curves (two for each vaccine lot) were tested. The plate layout was designed to be similar to that in Table 1 on the basis of statistical evaluation of edge effects. mAbs aliquots were used prediluted as described in above. Menveo vaccine, after reconstitution, was diluted with 5-fold dilution steps for MenA and 2-fold dilution steps (instead of 3-fold as in the preceding experiments) for MenC, MenW135 and MenY.

The reproducibility data was processed for the relative potency evaluation, which is a measure of both a vaccine's immunogenicity and potency using an excel sheet. Potency evaluation was performed using the Parallel Line Method as described in the European Pharmacopoeia 6.0. According to this model, the relationship between the logarithmic transformation of the dose and the response (OD or a transformation) can be represented as a straight line, over the range of doses used; the model is based on the parallelism assumption between the unknown and the standard preparation. The horizontal distance between the two lines is the estimation of the potency of the unknown preparation relative to the standard.

In particular, after choosing the linear range of each curve, relative potency is calculated as:

$$RelativePotency = antilog\left(-\frac{Intercept_{SAM} - Intercept_{STD}}{b_{COM}}\right)$$

where:

$b_{COM}$ is the common slope $Intercept_{SAM}$ is the intercept of the Sample curve, assuming a common slope $Intercept_{STD}$ is the intercept of the Standard curve, assuming a common slope In Table 6, mean potency values and coefficient of variation percentage are described. Given the exponential nature of the potency, the CV% was calculated as the standard deviation of the natural log-potencies, multiplied by 100%.

The acceptance criteria for the discrimination of invalid plates are:

R square of the Reference and test vaccine curves: >0.95 p-value non-parallelism: >0.05

TABLE 6

| | | Potency MenA | | | | | |
|---|---|---|---|---|---|---|---|
| | | 16 Feb. 2010 | | 24 Feb. 2010 | | 25 Feb. 2010 | |
| Operator | Plate | Potency | Ln-Potency | Potency | Ln-Potency | Potency | Ln-Potency |
| Op1- CB | plate 1 | 0.3875 | -0.9480 | 0.3547 | -1.0365 | 0.5347 | -0.6261 |
| Op1- CB | plate 2 | 0.4429 | -0.8144 | 0.3813 | -0.9641 | | |
| Op2 - FG | plate 1 | 0.4289 | -0.8466 | 0.3069 | -1.1813 | 0.4429 | -0.8144 |
| Op2 - FG | plate 2 | 0.5095 | -0.6744 | 0.2698 | -1.3101 | 0.4941 | -0.7049 |

| | Potency | Ln-Potency |
|---|---|---|
| mean | 0.4058 | -0.9019 |
| DS | | 0.2130 |
| CV % | 21 | |

☐ invalid plate

| | | Potency MenC | | | | | |
|---|---|---|---|---|---|---|---|
| | | 18 Feb. 2010 | | 24 Feb. 2010 | | 25 Feb. 2010 | |
| Operator | Plate | Potency | Ln-Potency | Potency | Ln-Potency | Potency | Ln-Potency |
| Op1- CB | plate 1 | 1.1206 | 0.1139 | 1.0538 | 0.0524 | 0.9906 | -0.0094 |
| Op1- CB | plate 2 | 1.1594 | 0.1479 | 0.9720 | -0.0284 | 1.0111 | 0.0110 |
| Op2 - FG | plate 1 | 1.0959 | 0.0916 | 1.1183 | 0.1118 | 1.1135 | 0.1075 |
| Op2 - FG | plate 2 | 1.2051 | 0.1866 | 1.2924 | 0.2565 | 1.1829 | 0.1680 |

| | Potency | Ln-Potency |
|---|---|---|
| mean | 1.1060 | 0.1008 |
| DS | | 0.0842 |
| CV % | 8 | |

| | | Potency MenW | | | | | |
|---|---|---|---|---|---|---|---|
| | | 16 Feb. 2010 | | 24 Feb. 2010 | | 25 Feb. 2010 | |
| Operator | Plate | Potency | Ln-Potency | Potency | Ln-Potency | Potency | Ln-Potency |
| Op1- CB | plate 1 | 0.9218 | -0.0814 | 0.8446 | -0.1689 | 0.8762 | -0.1322 |
| Op1- CB | plate 2 | 0.8548 | -0.1568 | 0.8241 | -0.1935 | 0.9613 | 0.0395 |
| Op2 - FG | plate 1 | 0.9042 | -0.1007 | 0.8607 | -0.1500 | 0.9548 | 0.0463 |
| Op2 - FG | plate 2 | 0.8332 | -0.1824 | 0.7838 | -0.2436 | 0.8551 | 0.1566 |

| | Potency | Ln-Potency |
|---|---|---|
| mean | 0.8714 | -0.1377 |
| DS | | 0.0609 |
| CV % | 6 | |

| | | Potency MenY | | | | | |
|---|---|---|---|---|---|---|---|
| | | 18 Feb. 2010 | | 24 Feb. 2010 | | 25 Feb. 2010 | |
| Operator | Plate | Potency | Ln-Potency | Potency | Ln-Potency | Potency | Ln-Potency |
| Op1- CB | plate 1 | 0.8649 | -0.1451 | 0.9047 | -0.1002 | 0.8980 | -0.1076 |
| Op1- CB | plate 2 | 0.8971 | -0.1086 | 0.9210 | -0.0823 | 1.1147 | 0.1086 |
| Op2 - FG | plate 1 | 0.9580 | -0.0429 | 0.9166 | -0.0871 | 0.8199 | -0.1986 |
| Op2 - FG | plate 2 | 0.9360 | -0.0661 | 1.0059 | 0.0059 | 1.1492 | 0.1391 |

| | Potency | Ln-Potency |
|---|---|---|
| mean | 0.9445 | -0.0571 |
| DS | | 0.0984 |
| CV % | 10 | |

Comparison of 3 Menveo Vaccine Test Lots with the Reference Lot.

Three recently produced vaccine lots were analyzed in comparison with the Reference lot. Each lot was tested in triplicate, in each plate four inhibition curves were analyzed: two by competing the mAbs with the Menveo vaccine Reference lot and two with the Menveo vaccine test lot under investigation (lot 1, 2 or 3).

Results, expressed as potency and CV% values, are described in Table 7:

Potency MenA

| vaccine | Operator | Plate | 26 Feb. 2010 Potency | Ln-Potency | Operator | vaccine | 26 Feb. 2010 Potency | Ln-Potency | Operator | vaccine | 03 Mar. 2010 Potency | Ln-Potency |
|---|---|---|---|---|---|---|---|---|---|---|---|---|
| lot 1 | Op1-CB | plate 1 | 0.6581 | -0.4185 | Op2-FG | lot 2 | 0.9377 | -0.0644 | Op2-FG | lot 3 | 0.7868 | -0.2398 |
| lot 1 | Op1-CB | plate 2 | 0.6752 | -0.3927 | Op2-FG | lot 2 |  |  | Op2-FG | lot 3 | 0.9138 | -0.0901 |
| lot 1 | Op1-CB | plate 3 | 0.7365 | -0.3058 | Op2-FG | lot 2 | 0.9036 | -0.1014 | Op2-FG | lot 3 | 0.9652 | -0.0354 |

|  | Potency | Ln-Potency |
|---|---|---|
| mean | 0.7178 | -0.2060 |
| DS |  | 0.1534 |
| CV % | 15 |  |

☐ invalid plate

Potency MenC

| vaccine | Operator | Plate | 26 Feb. 2010 Potency | Ln-Potency | Operator | vaccine | 26 Feb. 2010 Potency | Ln-Potency | Operator | vaccine | 03 Mar. 2010 Potency | Ln-Potency |
|---|---|---|---|---|---|---|---|---|---|---|---|---|
| lot 1 | Op1-CB | plate 1 | 0.7305 | -0.3140 | Op2-FG | lot 2 | 0.7185 | -0.3306 | Op2-FG | lot 3 | 0.7190 | -0.3299 |
| lot 1 | Op1-CB | plate 2 | 0.7071 | -0.3466 | Op2-FG | lot 2 | 0.6993 | -0.3577 | Op2-FG | lot 3 | 0.7781 | -0.2509 |
| lot 1 | Op1-CB | plate 3 | 0.6854 | -0.3778 | Op2-FG | lot 2 | 0.7160 | -0.3341 | Op2-FG | lot 3 | 0.7300 | -0.3147 |

|  | Potency | Ln-Potency |
|---|---|---|
| mean | 0.7200 | -0.3285 |
| DS |  | 0.0355 |
| CV % | 4 |  |

Potency MenW

| vaccine | Operator | Plate | 26 Feb. 2010 Potency | Ln-Potency | Operator | vaccine | 26 Feb. 2010 Potency | Ln-Potency | Operator | vaccine | 03 Mar. 2010 Potency | Ln-Potency |
|---|---|---|---|---|---|---|---|---|---|---|---|---|
| lot 1 | Op1-CB | plate 1 | 0.9279 | -0.0749 | Op2-FG | lot 2 | 0.8925 | -0.1137 | Op2-FG | lot 3 | 0.8207 | -0.1975 |
| lot 1 | Op1-CB | plate 2 | 0.9202 | -0.0832 | Op2-FG | lot 2 | 0.9835 | -0.0166 | Op2-FG | lot 3 | 1.0497 | 0.0485 |
| lot 1 | Op1-CB | plate 3 | 0.9633 | -0.0374 | Op2-FG | lot 2 | 0.9196 | -0.0839 | Op2-FG | lot 3 | 1.0161 | 0.0159 |

|  | Potency | Ln-Potency |
|---|---|---|
| mean | 0.9415 | -0.0603 |
| DS |  | 0.0734 |
| CV % | 7 |  |

Potency MenY

| vaccine | Operator | Plate | 26 Feb. 2010 Potency | Ln-Potency | Operator | vaccine | 26 Feb. 2010 Potency | Ln-Potency | Operator | vaccine | 03 Mar. 2010 Potency | Ln-Potency |
|---|---|---|---|---|---|---|---|---|---|---|---|---|
| lot 1 | Op1-CB | plate 1 | 0.7135 | -0.3376 | Op2-FG | lot 2 | 0.8479 | -0.1650 | Op2-FG | lot 3 | 0.8627 | -0.1476 |
| lot 1 | Op1-CB | plate 2 | 0.7631 | -0.2703 | Op2-FG | lot 2 | 0.8236 | -0.1941 | Op2-FG | lot 3 | 0.8022 | -0.2204 |
| lot 1 | Op1-CB | plate 3 | 0.7857 | -0.2412 | Op2-FG | lot 2 | 0.8242 | -0.1934 | Op2-FG | lot 3 | 0.8276 | -0.1892 |

|  | Potency | Ln-Potency |
|---|---|---|
| mean | 0.8044 | -0.2176 |
| DS |  | 0.0585 |
| CV % | 6 |  |

Discussion of Results

Plate Coatings.

The comparison between the two coating procedures did not show relevant differences for antigens MenA, MenW135 and MenY, whereas for antigen MenC the coating with the CRM-conjugate resulted in a partial inhibition of the monoclonal antibody at similar antibody concentration.

Plain polysaccharides are preferred and were chosen as coating antigen for the final assay protocol.

Secondary Antibody (Ab II).

The absorbance values of the four monoclonal tested at a fixed dilution showed similar results by using alkaline phosphatase versus horseradish peroxidase.

For the final assay protocol, the alkaline phosphatase was selected as the preferred condition for all antigens.

Monoclonal and Secondary Antibody Dilution Buffers.

All tested buffers showed similar responses. Buffer 1 (PBS 1×+0.01% TWEEN 20™+1% BSA) was selected for the final assay protocol.

Stability of mAb Dilutions.

The results demonstrated that mAbs were stable at +2-8° C. up to 3 days once diluted in the dilution buffer 1: PBS 1×+0.01% TWEEN 20™+1% BSA. Buffer 2 (PBS) showed in adequate stability for anti-A and anti-C mAbs.

mAbs Stability at −20° C.

The monoclonal aliquots were diluted with PBS+1% BSA and checked for the protein content and homogeneity. The four mAbs were differently diluted depending on the antigen (see paragraph) and stored as 1 ml aliquots at −20° C.

Coating Stability.

Results obtained with antigen MenA showed a significant difference in response curves between the freshly prepared plates and plates stored for 6 days after preparation. For MenC, MenW135, MenY antigens, no relevant differences were observed between day 0 and day 6 at 4° C.

Negative Controls.

The assay sensitivity was demonstrated by the inhibition curves obtained with the negative controls, which presented a lower inhibition activity in comparison with the standard vaccine.

Robustness—Coating Homogeneity.

The coating homogeneity was evaluated for the four mAbs as described above and the results indicated that there were no relevant differences in the CV% of absorbance values when treating the single plates as the mean values determined for all analyzed plates. For the four antigens individual and mean CV% are lower than 15%.

Robustness—Incubation Times.

The results didn't reveal significant differences among the different tested conditions. The selected incubation times for the primary Ab, for the secondary Ab and for the colorimetric reaction were 2 hours; 1 hour and 30 minutes, and 30 minutes, respectively.

Robustness—Coating Concentrations.

The coating concentration selected for the final assay protocol was 2 µg/ml of plain polysaccharide. The results indicated there weren't relevant differences among the tested coating concentrations, apart from the 1 µg/ml concentration, which resulted in an increase of the inhibition curves curvature. This feature of response curves is not appropriate for a relative potency determination.

Reproducibility.

Reproducibility data showed acceptable results, as indicated by the CV% of the potency values that are under 25% for MenA and under 15% for MenC, MenW135 and MenY.

Test of 3 Menveo Vaccine Lots in Comparison with the Reference Lot.

Results obtained by comparing, in the same plate, the vaccine Reference lot and a recently produced Menveo vaccine batch (three recent batches tested in total), demonstrated the similarity of lots under investigation. As shown in Table 7, the CV% of the potency values is below 20%.

Example 2

Validation of the ELISA Method for the Antigenicity of a Tetravalent *N. meningitidis* ACWY Capsular Saccharide Conjugate Vaccine Protocol Used For Validation.

This example summarizes validation of an embodiment of the in vitro antibody immunogenicity and potency assay that is to evaluate the antigenicity of a tetravalent *N. meningitidis* ACWY capsular saccharide conjugate vaccine. The assay is a competitive ELISA in which the vaccine competes with bactericidal serogroup specific monoclonal antibodies (anti-MenA, anti-MenC, anti-MenW135 and anti-MenY) in binding to native capsular saccharide controls. The inhibition curves obtained with a reference vaccine lot of known potency and immunogenicity in humans was compared to those obtained with a test vaccine lot under using a relative potency calculation, which is a measure of a vaccine's immunogenicity and potency. The validation included reconstituting the CRM-MenA lyophilized product phase with the MenC, W, Y conjugate product filled in syringes and with the MenC, W, Y conjugate product filled in vials.

Assay Procedure.

Microtiter plates were coated with the capsular polysaccharide at a final concentration of 2.0 µg/ml, in PBS pH 7.4. Plates were sealed, incubated overnight at 2°-8° C., then washed and saturated with a PBS pH 7.4 solution containing 1% porcine gelatin, as a blocking reagent, for a two-hour incubation at 37° C. Then plates were fixed with a saline solution, containing 4% Polyvinyl-pyrrolidone and 10% sucrose, and incubated at room temperature for two hours. After incubating, the fixing solution was aspired and plates were left to dry overnight on the bench.

In a different polypropylene microtiter plate the specific competitors (Menveo Reference vaccine tested in human clinical trials and Menveo test lot) were diluted with buffer solution (1% Bovine Serum Albumin in PBS pH 7.4 with 0.01% TWEEN 20™) with two-fold (MenCWY) or five-fold dilution (MenA), depending on the antigen. Then, the same volume of mAbs (anti-A, anti-C, anti-W and anti-Y), at a fixed dilution, was added to the wells and allowed to interact directly with the competitor at room temperature. After this step the mixture was transferred to the coated and saturated plates and incubated for two hours at 37° C. Plates were then washed and a goat-anti-mouse IgG antibody conjugated to Alkaline Phosphatase was added. The secondary antibody was incubated for 1.5 hours at 37° C. and, after washing, plates were left for 30 min at room temperature with a chromogenic substrate solution. Plates were blocked with a NaOH solution and then absorbance values read at a wavelength of 405-620 nm.

The response curve of a vaccine lot under investigation is determined by a relative potency evaluation with respect to the reference vaccine, using the Parallel-Line Model, as described in the European Pharmacopoeia 6.0. According to this model, the relationship between the logarithmic transformation of the dose and the response (OD or a transformation) can be represented as a straight line over the range of doses used; the model is based on the parallelism assumption between the unknown and the reference vaccine. The horizontal distance between the two lines indicates the potency and immunogenicity of the unknown lot relative to the reference lot.

Validation Procedure and Results.

Validation analyses were performed in the QCIM laboratories (GMP compliant) by an RC operator, appropriately trained, and by two QCIM operators for the concomitant transfer of the method.

The following parameters were evaluated:
Precision:
  Repeatability
  Reproducibility
Linearity
Specificity
Accuracy
Range Robustness
  Coating stability
  Precision—Repeatability.

Repeatability of the method was evaluated by the analysis of 6 replicates of each antigen (6 plates each containing the Reference vaccine and the test vaccine, CRM-MenA lyophilized component and the MenCWY liquid component from pre-filled syringe and MenCWY liquid component from vial), distributed as shown in Table 1 above. Each antigen was tested by the RC operator in the same analytical session.

Results are displayed as Potency value, natural log Potency value and Coefficient of Variation percentage (CV%) of potency values.

The Coefficient of Variation of the potency was calculated using the Taylor expansion to approximate the variance of a function. The resulting Coefficient of Variation percentage of the potency was: CV%=SD(ln Potency)*100. Results are reported in Table 8, below. For each antigen, the CV% of the relative potency values must be <15%.

TABLE 8

Repeatability of the assay calculated by potency values obtained with six repetitions of Menveo vaccine Lot 1.

|  | MenA Potency values | lnPotency values | MenW Potency values | lnPotency values |
|---|---|---|---|---|
| Lot 1 | 0.766 | −0.2666 | 0.923 | −0.0801 |
|  | 0.702 | −0.3538 | 0.913 | −0.0910 |
|  | 0.896 | −0.1098 | 0.938 | −0.0640 |
|  | 0.785 | −0.2421 | 0.956 | −0.0450 |
|  | 0.701 | −0.3552 | 0.944 | −0.0576 |
|  | 0.853 | −0.1590 | 1.072 | 0.0695 |
| Mean | 0.784 |  | 0.958 |  |
| CV % | 10.0 |  | 5.8 |  |

|  | MenC Potency values | lnPotency values | MenY Potency values | lnPotency values |
|---|---|---|---|---|
| Lot 1 | 0.723 | −0.3243 | 0.869 | −0.1404 |
|  | 0.767 | −0.2653 | 0.807 | −0.2144 |
|  | 0.807 | −0.2144 | 0.788 | −0.2383 |
|  | 0.787 | −0.2395 | 0.946 | −0.0555 |
|  | 0.75 | −0.2877 | 0.925 | −0.0780 |
|  | 0.741 | −0.2998 | 0.937 | −0.0651 |
| Mean | 0.763 |  | 0.879 |  |
| CV % | 4.0 |  | 7.9 |  |

Reproducibility.

The reproducibility parameter was evaluated by testing three different vaccine lots by three operators on different days. The RC operator tested each lot in double, for each antigen, during three different analytical sessions, while the two QC operators tested each lot in single, for each antigen, during three different analytical sessions. The vaccine lots used were as follows:

Lot 1: CRM-MenA liquid phase; MenCWY lyophilized
Lot 2: CRM-MenA liquid phase; MenCWY lyophilized
Lot 3: CRM-MenA liquid phase; MenCWY lyophilized Results are shown in Tables 9-12, below. For each of the antigens MenC, MenW and MenY, and for each vaccine lot the CV% of 12 relative potency determinations must be <20%. For the antigen MenA, and for each vaccine lot the CV% of 12 relative potency determinations must be <25%. For each of the antigens MenC, MenW and MenY, and for each vaccine lot the CV% of 6 relative potency determinations of QC operators must be <20%. For the antigen MenA, and for each vaccine lot the CV% of 6 relative potency determinations of QC operators must be <25%. For each antigen and for each vaccine lot, the t-test for the significance of the differences between CR/QC operators must be >0.01.

TABLE 9

Reproducibility of the assay calculated by potency values obtained by testing MenA antigen of three different Menveo vaccine lots.

|  | Operator CR | | Operator QCa | | Operator QCb | |
|---|---|---|---|---|---|---|
| Lot 1 | 0.823 | −0.1948 | 0.705 | −0.3496 | 0.691 | −0.3696 |
|  | 0.558 | −0.5834 | 0.688 | −0.3740 | 0.847 | −0.1661 |
|  | 0.687 | −0.3754 | 0.957 | −0.0440 | 0.630 | −0.4620 |
|  | 0.680 | −0.3857 |  |  |  |  |
|  | 0.749 | −0.2890 |  |  |  |  |
|  | 0.873 | −0.1358 |  |  |  |  |
| Total mean CV % | 0.741 15.2 | | QC Operators Mean CV % | 0.753 15.6 | | |
| Lot 2 | 0.609 | −0.4959 | 0.706 | −0.3481 | 0.593 | −0.5226 |
|  | 0.603 | −0.5058 | 0.655 | −0.4231 | 0.916 | −0.0877 |
|  | 0.870 | −0.1393 | 0.614 | −0.4878 | 0.551 | −0.5960 |
|  | 1.169 | 0.1561 |  |  |  |  |
|  | 0.877 | −0.1312 |  |  |  |  |
|  | 0.596 | −0.5175 |  |  |  |  |
| Total mean CV % | 0.730 23.4 | | QC Operators mean CV % | 0.673 18.0 | | |
| Lot 3 | 0.762 | −0.2718 | 0.598 | −0.5142 | 0.726 | −0.3202 |
|  | 0.595 | −0.5192 | 0.804 | −0.2182 | 0.870 | −0.1393 |
|  | 0.947 | −0.0545 | 0.809 | −0.2120 | 0.762 | −0.2718 |
|  | 1.245 | 0.2191 |  |  |  |  |
|  | 0.702 | −0.3538 |  |  |  |  |
|  | 0.980 | −0.0202 |  |  |  |  |
| Total mean CV % | 0.817 20.8 | | QC Operators mean CV% | 0.762 13.0 | | |

TABLE 10

Reproducibility of the assay calculated by potency values obtained by testing MenC antigen of three different Menveo vaccine lots.

|  | Operator CR | | Operator QCa | | Operator QCb | |
|---|---|---|---|---|---|---|
| Lot 1 | 0.787 | −0.2395 | 0.848 | −0.1649 | 0.819 | −0.1997 |
|  | 0.684 | −0.3798 | 0.719 | −0.3299 | 0.823 | −0.1948 |
|  | 0.801 | −0.2219 | 0.752 | −0.2850 | 0.660 | −0.4155 |
|  | 0.777 | −0.2523 |  |  |  |  |
|  | 0.727 | −0.3188 |  |  |  |  |
|  | 0.773 | −0.2575 |  |  |  |  |
| Total mean CV % | 0.764 7.7 | | QC Operators mean CV % | 0.770 9.6 | | |
| Lot 2 | 0.730 | −0.3147 | 0.772 | −0.2588 | 0.802 | −0.2206 |
|  | 0.782 | −0.2459 | 0.722 | −0.3257 | 0.934 | −0.0683 |
|  | 0.840 | −0.1744 | 0.894 | −0.1120 | 0.776 | −0.2536 |
|  | 0.934 | −0.0683 |  |  |  |  |
|  | 0.780 | −0.2485 |  |  |  |  |
|  | 0.958 | −0.0429 |  |  |  |  |
| Total mean CV % | 0.827 9.9 | | QC Operators mean CV % | 0.817 9.7 | | |
| Lot 3 | 0.693 | −0.3667 | 0.784 | −0.2433 | 0.648 | −0.4339 |
|  | 0.712 | −0.3397 | 0.837 | −0.1779 | 0.869 | −0.1404 |
|  | 0.731 | −0.3133 | 0.666 | −0.4065 | 0.768 | −0.2640 |
|  | 0.786 | −0.2408 |  |  |  |  |
|  | 0.794 | −0.2307 |  |  |  |  |
|  | 0.694 | −0.3653 |  |  |  |  |
| Total mean CV % | 0.749 9.2 | | QC Operators mean CV % | 0.762 11.9 | | |

TABLE 11

Reproducibility of the assay calculated by potency values obtained by testing MenW antigen of three different Menveo vaccine lots.

|  | Operatore CR | | Operatore QCa | | Operatore QCb | |
| --- | --- | --- | --- | --- | --- | --- |
| Lot 1 | 1.168 | 0.1553 | 1.237 | 0.2127 | 1.103 | 0.0980 |
|  | 1.089 | 0.0853 | 0.955 | −0.0460 | 1.033 | 0.0325 |
|  | 1.091 | 0.0871 | 0.890 | −0.1165 | 1.033 | 0.0325 |
|  | 1.146 | 0.1363 |  |  |  |  |
|  | 0.989 | −0.0111 |  |  |  |  |
|  | 0.875 | −0.1335 |  |  |  |  |
| Total mean | 1.051 |  | QC Operators mean |  | 1.042 |  |
| CV % | 10.6 |  | CV % | 11.4 |  |  |
| Lot 2 | 1.115 | 0.1089 | 0.966 | −0.0346 | 1.062 | 0.0602 |
|  | 1.064 | 0.0620 | 1.139 | 0.1302 | 1.024 | 0.0237 |
|  | 1.194 | 0.1773 | 1.093 | 0.0889 | 0.972 | −0.0284 |
|  | 1.194 | 0.1773 |  |  |  |  |
|  | 0.945 | −0.0566 |  |  |  |  |
|  | 1.140 | 0.1310 |  |  |  |  |
| Total mean | 1.076 |  | QC Operators mean |  | 1.043 |  |
| CV % | 8.0 |  | CV % | 6.5 |  |  |
| Lot 3 | 0.873 | −0.1358 | 1.014 | 0.0139 | 1.111 | 0.1053 |
|  | 1.115 | 0.1089 | 0.879 | −0.1290 | 0.948 | −0.0534 |
|  | 0.961 | −0.0398 | 0.964 | −0.0367 | 1.041 | 0.0402 |
|  | 1.102 | 0.0971 |  |  |  |  |
|  | 0.929 | −0.0736 |  |  |  |  |
|  | 0.989 | −0.0111 |  |  |  |  |
| Total mean | 0.994 |  | QC Operators mean |  | 0.993 |  |
| CV % | 8.5 |  | CV % | 8.1 |  |  |

TABLE 12

Reproducibility of the assay calculated by potency values obtained by testing MenY antigen of three different Menveo vaccine lots.

|  | Operator CR | | Operator QCa | | Operator QCb | |
| --- | --- | --- | --- | --- | --- | --- |
| Lot 1 | 0.900 | −0.1054 | 0.795 | −0.2294 | 0.915 | −0.0888 |
|  | 0.921 | −0.0823 | 0.899 | −0.1065 | 0.989 | −0.0111 |
|  | 0.851 | −0.1613 | 0.787 | −0.2395 | 0.945 | −0.0566 |
|  | 0.848 | −0.1649 |  |  |  |  |
|  | 0.838 | −0.1767 |  |  |  |  |
|  | 0.763 | −0.2705 |  |  |  |  |
| Total mean | 0.871 |  | QC Operators mean |  | 0.888 |  |
| CV % | 7.9 |  | CV % | 9.3 |  |  |
| Lot 2 | 1.155 | 0.1441 | 0.881 | −0.1267 | 0.959 | −0.0419 |
|  | 0.998 | −0.0020 | 0.980 | −0.0202 | 1.009 | 0.0090 |
|  | 0.908 | −0.0965 | 0.879 | −0.1290 | 0.947 | −0.0545 |
|  | 0.722 | −0.3257 |  |  |  |  |
|  | 0.819 | −0.1997 |  |  |  |  |
|  | 0.925 | −0.0780 |  |  |  |  |
| Total mean | 0.932 |  | QC Operators mean |  | 0.943 |  |
| CV % | 11.7 |  | CV % | 5.6 |  |  |
| Lot 3 | 0.755 | −0.2810 | 0.949 | −0.0523 | 0.927 | −0.0758 |
|  | 0.990 | −0.0101 | 0.848 | −0.1649 | 0.941 | −0.0608 |
|  | 0.887 | −0.1199 | 0.944 | −0.0576 | 0.918 | −0.0856 |
|  | 0.882 | −0.1256 |  |  |  |  |
|  | 0.997 | −0.0030 |  |  |  |  |
|  | 0.949 | −0.0523 |  |  |  |  |
| Total mean | 0.916 |  | QC Operators mean |  | 0.921 |  |
| CV % | 7.6 |  | CV % | 4.2 |  |  |

The t-test results for each antigen and lot are reported in Table 13, below.

| | | Mean Comparison | | |
| --- | --- | --- | --- | --- |
| Antigen | Lot | Difference* | p-value | Acceptance Criteria |
| MenA | 1 | −0.0205 | 0.72 | ≥0.01 |
|  | 2 | 0.0862 | 0.33 |  |
|  | 3 | 0.0697 | 0.38 |  |
| MenC | 1 | −0.0195 | 0.78 |  |
|  | 2 | 0.0345 | 0.70 |  |
|  | 3 | −0.0460 | 0.57 |  |
| MenW | 1 | 0.0255 | 0.79 |  |
|  | 2 | 0.0869 | 0.21 |  |
|  | 3 | 0.0015 | 0.98 |  |
| MenY | 1 | −0.0549 | 0.43 |  |
|  | 2 | −0.0469 | 0.66 |  |
|  | 3 | −0.0226 | 0.74 |  |

*data are evaluated in logarithm based step-dil

The t-test for each group/antigen/lot showed no significant differences between means. The p-value in each case was well above the defined acceptance criteria.

Linearity.

The linearity parameter was evaluated by analyzing vaccine reference results from the repeatability experiments. Considered on a natural log transformation, the OD response was expressed as a linear function of the vaccine concentration by the Ordinary Least Squares (OLS) method. Each curve was evaluated as resulted from two replicates. At least five consecutive points inside the linear range were considered and the following parameters were evaluated:

Plot of the response vs. vaccine concentrations

R-squared

P-value associated with the linear regression

Results are shown in FIGS. 2A-2F, FIGS. 3A-3F, FIGS. 4A-4F, FIGS. 5A-5F and in Table 14.

Acceptance criteria

The coefficient of determination (R-squared) must be >0.95 p-value for significance of linear regression must be >0.05.

TABLE 14

Linear Regression

| Antigen | Plate | No of consecutive concentration points | p-value | R-squared |
| --- | --- | --- | --- | --- |
| MenA | 1 | 7 | 0.00 | 0.97 |
|  | 2 | 7 | 0.00 | 0.99 |
|  | 3 | 6 | 0.00 | 1.00 |
|  | 4 | 6 | 0.00 | 0.99 |
|  | 5 | 7 | 0.00 | 0.99 |
|  | 6 | 7 | 0.00 | 0.99 |
| MenC | 1 | 7 | 0.00 | 0.99 |
|  | 2 | 7 | 0.00 | 0.99 |
|  | 3 | 7 | 0.00 | 0.97 |
|  | 4 | 8 | 0.00 | 0.99 |
|  | 5 | 7 | 0.00 | 0.98 |
|  | 6 | 7 | 0.00 | 0.99 |
| MenW | 1 | 7 | 0.00 | 0.99 |
|  | 2 | 7 | 0.00 | 0.99 |
|  | 3 | 7 | 0.00 | 0.96 |
|  | 4 | 6 | 0.00 | 0.98 |
|  | 5 | 6 | 0.00 | 0.99 |
|  | 6 | 7 | 0.00 | 0.99 |
| MenY | 1 | 9 | 0.00 | 0.99 |
|  | 2 | 9 | 0.00 | 0.99 |
|  | 3 | 9 | 0.00 | 0.99 |
|  | 4 | 8 | 0.00 | 0.99 |
|  | 5 | 9 | 0.00 | 0.99 |
|  | 6 | 8 | 0.00 | 0.99 |

Specificity.

The specificity of the method was evaluated by analyzing, for each antigen, the competition of the monoclonal antibody against both the homologous and the non-homologous monovalent bulk CRM-conjugates. Monovalent bulk vaccines were diluted to reach, as starting concentration, the amount of each vaccine component contained in the drug final product. Subsequent dilutions were as follows: 1/5 dilution steps for MenA and 1/2 dilution steps for MenC, MenW and MenY. The results are shown in Table 15. Exemplary plots for MenW135 are shown in FIGS. 7A-7B.

Acceptance criteria:

The Reference vaccine must have an $R^2 \geq 0.95$.

Homologous monovalent bulk vaccines must have a p-value for parallelism≥0.05.

Non-homologous monovalent bulk vaccines must have a p-value for parallelism<0.05.

TABLE 15

Specificity of the assay evaluated by the p-values for parallelism obtained by testing the homologous and non-homologous monovalent bulk vaccines.

|  | Bulk CRM-MenA | Bulk CRM-MenC | Bulk CRM-MenW | Bulk CRM-MenY |
|---|---|---|---|---|
| mAb anti-A | 0.21 | 0.00 | 0.00 | 0.00 |
| mAb anti-C | 0.00 | 0.66 | 0.00 | 0.00 |
| mAb anti-W | 0.00 | 0.00 | 0.66 | 0.00 |
| mAb anti-Y | 0.00 | 0.00 | 0.00 | 0.80 |

Accuracy.

The accuracy parameter was satisfied accomplishing the linearity, precision and specificity of the method.

Range.

The range parameter was defined as the linear portion of curves which satisfied the validity criteria of the analysis. On the basis of the linearity results, at least five consecutive points are within the linear region.

Robustness—Coating Stability.

This parameter was evaluated by testing one plate/Ag at different time-points and competing the mAb binding with the Reference and Test Lot 1 vaccines. The plate scheme is shown in Table 1 above. After the coating and post-coating procedures, the plates were stored at 2-8° C. and analyzed at the following time-points: day 0, 3, 6, 10, 15 and 21. The results from day 0 were used in the reproducibility experiment by the operator QCb described above. The results are shown in Table 16.

Acceptance criteria:

For each antigen, the recovery percentage of the potency value calculated with respect to the potency value at time 0 must not exceed 20%. The criterion is considered not fulfilled if this value is higher than 20% for at least two consecutive stability time-points.

TABLE 16

Coating stability evaluated by the recovery percentages of the potency values at different time points. Results that exceed ±20% are underlined.

|  | MenA | | MenC | | MenW | | MenY | |
|---|---|---|---|---|---|---|---|---|
|  | Potency Value | recovery % | Potency Value | recovery % | Potency Value | recovery % | Potency Value | recovery % |
| DAY0 | 0.691 |  | 0.819 |  | 1.103 |  | 0.915 |  |
| DAY3 | 0.965 | <u>140</u> | 0.757 | 92 | 1.079 | 98 | 0.92 | 101 |
| DAY6 | 0.736 | 107 | 0.728 | 89 | 0.979 | 89 | 0.899 | 98 |
| DAY10 | 0.837 | <u>121</u> | 0.818 | 100 | 0.901 | 82 | 0.734 | 80 |
| DAY15 | 0.778 | 113 | 0.735 | 90 | 0.984 | 89 | 0.993 | 109 |
| DAY21 | 0.737 | 107 | 0.782 | 95 | 0.972 | 88 | 0.806 | 88 |

Discussion of Results

Precision.

The parameters tested to check the precision of the method fulfilled the set acceptance criteria.

Precision—Repeatability.

The CV% of the potency values, determined for the four antigens, varied from 4.0% to 10.0%, within the indicated limit of 15% (Table 8).

Precision—Reproducibility.

The CV% of the potency values between RC and QC operators, determined for the MenA, varied from 15.2% to 23.4% within the indicated limit of 25%; for MenC, MenW and MenY, CV% varied from 7.6% to 11.7% within the indicated limit of 20%. The CV% of the potency values obtained by QC operators for MenA ranged from 13.0% to 18.0% within the indicated limit of 25%; for MenC, MenW and MenY, CV% obtained by QC operators varied from 9.3% to 11.9% within the indicated limit of 20% (Tables 9-12). The p-value determined for each antigen and lot varied from 0.21 to 0.98, well above the indicated limit of 0.01.

Linearity.

Vaccine reference curves showed a linear pattern on no less than six consecutive points. The R-squared varied from 0.96 to 1.00, so all were above the selected limit of 0.95. P-value to test the significance of the linear model was lower than the selected limit of 0.01.

Specificity.

The p-values for parallelism calculated for response curves of the unrelated monovalent bulk vaccines were in all cases below 0.05, while the p-values calculated for the response curves of homologous monovalent bulks ranged from 0.21 to 0.80, thus fulfilling the acceptance criteria.

Accuracy.

The accuracy parameter was satisfied accomplishing the linearity, precision and specificity of the method.

Range.

The linear portion of the dilution curve was included in the range of concentrations defined above.

Robustness—Coating Stability.

Two values did not meet the 20% criterion. For MenA antigen, for day 3 the recovery compared to day 0 was 140%, and for day 10 the recovery was 121%. However, since these two time points are not consecutive, no decreasing trend was observed.

Example 3

This example describes experiments which evaluate the sensitivity of an embodiment of the in vitro antibody binding assay that is used to evaluate the immunogenicity and potency of a tetravalent N. meningitidis by monitoring changes in the antigenicity of such vaccines.

This example evaluates the assay's capacity to discriminate between standard vaccine (potent and immunogenic) and artificially altered (sub-potent and sub-immunogenic) vaccine batches. To this purpose "sub potent" and "sub-immunogenic" vaccine batches (or batches with inactivated active product ingredient) were generated at different free saccharide contents or with de-O-acetylated polysaccharide.

The Relative Potency of these samples, which is a measure of a vaccine's immunogenicity and potency, was measured in comparison with a Reference Menveo vaccine lot.

The principle of the assay is a competitive ELISA, in which a bactericidal serogroup-specific monoclonal antibody is inhibited in binding to the native capsular polysaccharide by the addition of the Menveo vaccine. The assay is a competitive ELISA in which the vaccine competes with bactericidal serogroup-specific monoclonal antibodies (anti-MenA, anti-MenC, anti-MenW135 and anti-MenY) in binding to native capsular saccharide controls.

In order to verify whether is possible to discriminate between a Reference Menveo vaccine and ad hoc modified batches, the in vitro antibody binding assay was applied running each test in triplicate.

temperature for two hours; after the incubation time the fixing solution was drawn and plates were left to dry overnight on the bench.

In a different polypropylene microtiter plate (NUNC) specific competitors (Menveo vaccine or tetravalent bulks) were diluted with buffer solution (1% Bovine Serum Albumin in PBS pH 7.4+Tween 20 0.01%) with two-fold or five-fold dilution steps, depending on the antigen (see Table 17). Then, the same volume of monoclonal antibodies (mAbs), used at a fixed dilution, was added into the wells and allowed to interact directly with the competitor at room temperature. Within 10 minutes the mixture was transferred to the coated and saturated plates and incubated for two hours at 37° C. Plates were then washed and a goat anti-mouse IgG antibody conjugated to Alkaline Phosphatase was added to the plates. The secondary antibody was incubated for 1.5 hours at 37° C. and, after washing, plates were incubated for 30 min at room temperature with a chromogenic substrate solution. Absorbance values were read at the dual wavelength 405-620/650 nm.

Plate layout used for the analysis is described in Table 17.

TABLE 17

Plate layout for MenA and MenC antigens (columns 1 and 12, rows A, B, G and H = blank; rows C-F = mAb A1 or C2, at fixed dilution, added with the competitors at 10 two-fold (MenC) or 10 five-fold (MenA) dilutions, starting from 10000 ng/ml (MenA) or 5000 ng/ml (MenC). MenW$_{135}$ and MenY have the same plate layout as MenC.

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | | | | | | | | | | | |
| C | REF VACCINE | 10000 | 2000 | 400 | 80 | 16 | 3.2 | 0.64 | 0.128 | 0.0256 | 0.00512 | |
| D | | 10000 | 2000 | 400 | 80 | 16 | 3.2 | 0.64 | 0.128 | 0.0256 | 0.00512 | |
| E | TEST VACCINE | 10000 | 2000 | 400 | 80 | 16 | 3.2 | 0.64 | 0.128 | 0.0256 | 0.00512 | |
| F | | 10000 | 2000 | 400 | 80 | 16 | 3.2 | 0.64 | 0.128 | 0.0256 | 0.00512 | |
| G | | | | | | | | | | | | |
| H | | | | | | | | | | | | |

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | | | | | | | | | | | |
| C | REF VACCINE | 5000 | 2500 | 1250 | 625 | 313 | 156 | 78 | 39 | 20 | 10 | |
| D | | 5000 | 2500 | 1250 | 625 | 313 | 156 | 78 | 39 | 20 | 10 | |
| E | TEST VACCINE | 5000 | 2500 | 1250 | 625 | 313 | 156 | 78 | 39 | 20 | 10 | |
| F | | 5000 | 2500 | 1250 | 625 | 313 | 156 | 78 | 39 | 20 | 10 | |
| G | | | | | | | | | | | | |
| H | | | | | | | | | | | | |

Methods

In Vitro Potency Assay

Microtiter plates were coated with the capsular polysaccharide, 2.0 mcg/ml in PBS pH 7.4. Plates were sealed, incubated overnight at 2°-8° C., then washed and saturated with a PBS pH 7.4 solution containing 1% porcine gelatin, as blocking reagent, for two hours incubation at 37° C. Then plates were fixed with a saline solution, containing 4% Polyvinylpyrrolidone (Serva) and 10% sucrose, and incubated at room Preparation of Conjugate Samples with Different Level of Free Polysaccharide Conjugate samples with different level of un-conjugated polysaccharide, ranging from 10% to 95%, were prepared by mixing the bulk conjugate material with the hydrolyzed polysaccharides having shorter chain lengths, added at a different amount, ranging from 10% to 95%. (Table 18).

TABLE 18

Saccharide and protein concentrations in tested samples.

| Sample | Saccharide concentration (µg/mL) | Protein content (µg/mL) | Saccharide/Protein |
|---|---|---|---|
| $CRM_{197}$-MenA Lot GFB001A | 1901.64 | 4523.7 | 0.342 |
| $CRM_{197}$-MenC Lot TRMENC01 | 641.0 | 1012.9 | 0.63 |
| $CRM_{197}$-$MenW_{135}$ Lot GFB007W | 1468.9 | 2181.4 | 0.67 |
| $CRM_{197}$-MenY Lot GFB008Y | 2993.9 | 4794.0 | 0.62 |
| Hydrolyzed MenA Lot MS2910109 | 5057.0 | N/A | N/A |
| Hydrolyzed MenC Lot 1 VCR | 3560.0 | N/A | N/A |
| Hydrolyzed $MenW_{135}$ Lot MS030210 | 6755.0 | N/A | N/A |
| Hydrolyzed MenY Lot MS050210 | 7360.0 | N/A | N/A |

N/A: Not Applicable

Preparation and characterization of de-O-acetylated conjugate samples Groups A, C, $W_{135}$ and Y polysaccharides conjugated to $CRM_{197}$ were de-O-acetylated by addition of 1 M $Na_2CO_3$ (10% as v/v) and incubation at room temperature for 2 hours. The samples were neutralized by addition of aqueous HCl 1:1 v/v and purified by 30 kDa MWCO Microcon centrifugal filter (Millipore), in order to remove the salts used for de-Oacetylation, and reconstituted in 10 mM sodium phosphate pH 7.2 as buffer.

The complete de-O-acetylation of polysaccharides was assessed by $_1$H NMR analysis (FIGS. 8A-8D). For all polysaccharides, the O-acetyl (OAc) signals disappeared and free Acetate (Acetate) was generated after the basic treatment (see spectral window 2.5÷1.5 ppm in the right box). As a consequence of the O-acetylation removal, the NAc signals were slightly shifted and, in addition, resolved in a single peak for $CRM_{197}$-MenC.

The saccharide content of meningococcal A conjugate was estimated by a home-built dosage of mannosamine-6-phosphate using HPLC-Pad analysis. The saccharide content of C, $W_{135}$ and Y samples was estimated by the Svennerhom colorimetric assay. The protein content of all samples was estimated by colorimetric MicroBCA commercial kit assay (Pierce), as reported in Table 19.

TABLE 19

Saccharide and protein content of de-O-acetylated samples.

| Sample | Saccharide content (µg/mL) | Protein content (µg/mL) | Saccharide/Protein |
|---|---|---|---|
| $CRM_{197}$-MenA | 319.7 | 985.8 | 0.32 |
| $CRM_{197}$-MenC | 450.9 | 887.0 | 0.51 |
| $CRM_{197}$-$MenW_{135}$ | 637.6 | 776.7 | 0.82 |
| $CRM_{197}$-MenY | 876.2 | 1190.9 | 0.74 |

Figure 9:
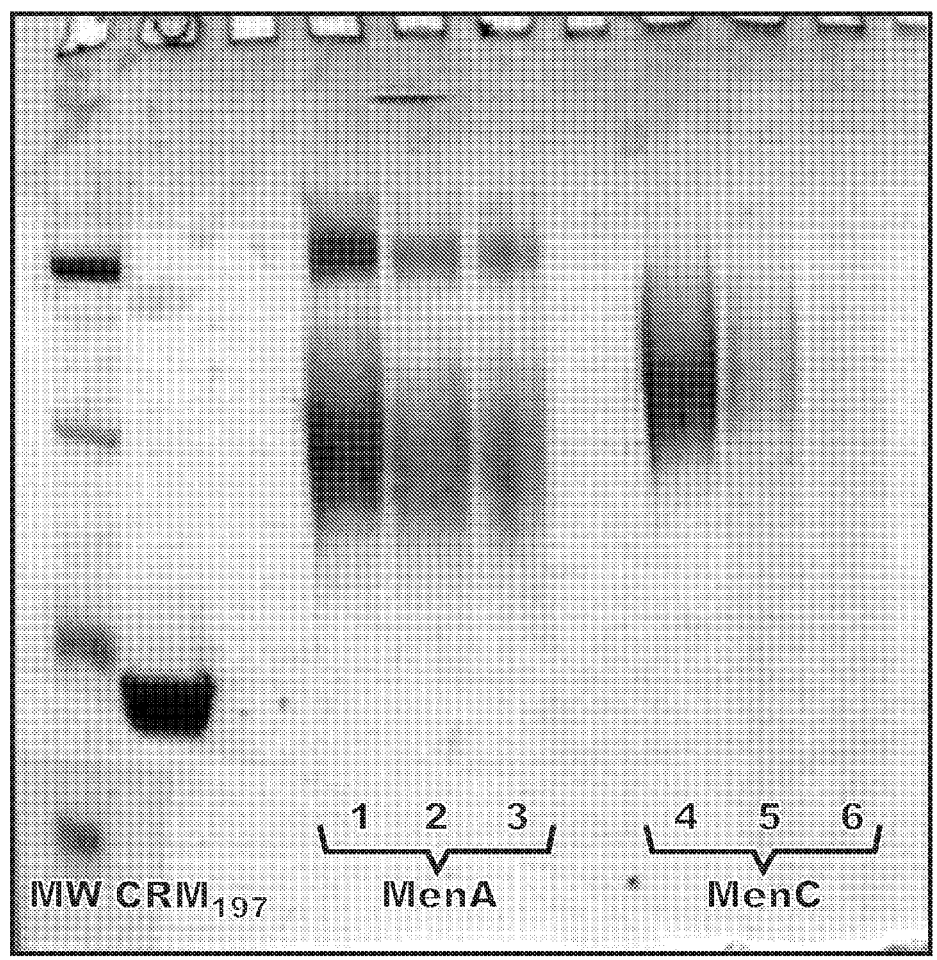
FIG. 9: Coomassie-stained SDS-Page gel (7% Tris Acetate) of $CRM_{197}$-MenA (Line 1: Starting material, Line 2: 30 kDa Retentate, Line 3: 30 kDa Permeate) and $CRM_{197}$-MenC (Line 4: Starting material, Line 5: 30 kDa Retentate, Line 6: 30 kDa Permeate).
Figure 10:
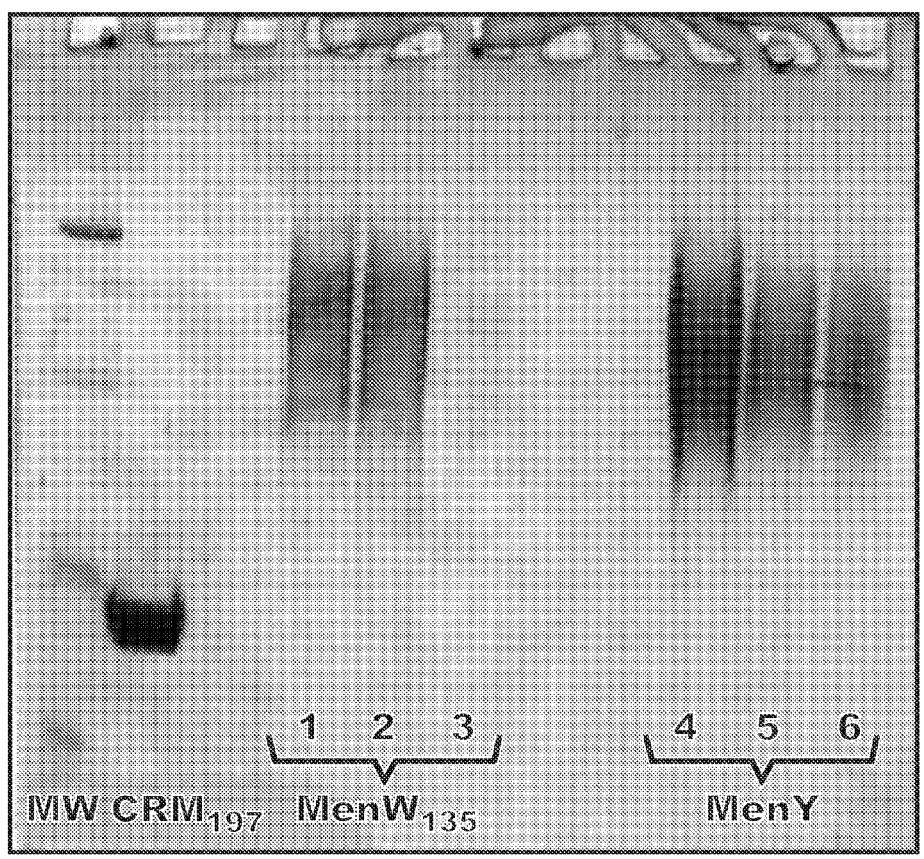
FIG. 10: Coomassie-stained SDS-Page gel (7% Tris Acetate) of $CRM_{197}$-MenW135 (Line 1: Starting material, Line 2: 30 kDa Retentate, Line 3: 30 kDa Permeate) and $CRM_{197}$-MenY (Line 4: Starting material, Line 5: 30 kDa Retentate, Line 6: 30 kDa Permeate).

In addition the de-O-acetylated conjugates were characterized by SDS-Page analysis (FIGS. 9 and 10).

Results

For each antigen, 5 monovalent vaccine batches, at different free saccharide percentages were prepared and tested in the final drug presentation (MenAC$W_{135}$Y tetravalent combination), to verify assay performance sensitivity. The free saccharide content added to each liquid monovalent bulk (10%, 25%, 50%, 75% and 95%) resulted in an increase of the total amount initially present in each bulk sample.

Table 20 reports the free saccharide content, expressed as percent of the total saccharide, present in each product used for generating the altered batches and the amount present in the reference vaccine.

TABLE 20

Free saccharide percentages in the monovalent liquid samples and in the reference lots.

| | Free saccharide content (%) | | | |
|---|---|---|---|---|
| | MenA | MenC | MenW | MenY |
| Bulk MenA-$CRM_{197}$ (Lot GFB001A) | <4.6 | | | |
| MenA-$CRM_{197}$ Lyo (REF Lot 039011) | <5 | | | |
| Bulk MenC-$CRM_{197}$ (Lot TRMENC01) | | <1 | | |
| MenCWY-$CRM_{197}$ (REF Lot 091201) | | <10 | | |
| Bulk MenW-$CRM_{197}$ (Lot GFB007W) | | | 4.8 | |
| MenCWY-$CRM_{197}$ (REF Lot 091201) | | | <12 | |
| Bulk MenY-$CRM_{197}$ (Lot GFB008Y) | | | | 2.1 |
| MenCWY-$CRM_{197}$ (REF Lot 091201) | | | | <13 |

The limit specifications for free saccharide content in the drug product, for the four conjugates, are the following:
<10% for MenA;
<17% for MenC, MenW135 and MenY.

Relative potency values determined in each test were compared to the cut off level assigned to each antigen (see Table 21).

TABLE 21

Cut-off relative potency values for the four antigens

| Antigen | 3 sigma LL |
|---|---|
| MenA | 0.421 |
| MenC | 0.495 |
| MenW | 0.690 |
| MenY | 0.679 |

Each bulk sample to be tested was prepared combining the corresponding altered bulk with the monovalent bulk samples of the other conjugates, to obtain the final drug product (MenACW135Y polysaccharide-CRM conjugate).

Moreover, a de-O-acetylated sample for each conjugate was prepared with the aim to investigate the impact of the polysaccharide acetylation status on in vitro potency readouts.

All samples were analyzed in triplicate, using the plate layout described in Table 17. The Menveo vaccine batch used as reference is a MenA lyophilized batch reconstituted with the liquid MenCW135Y batch.

Results referring to samples containing different free saccharide degree are shown in FIGS. 11-14.

Figure 15:
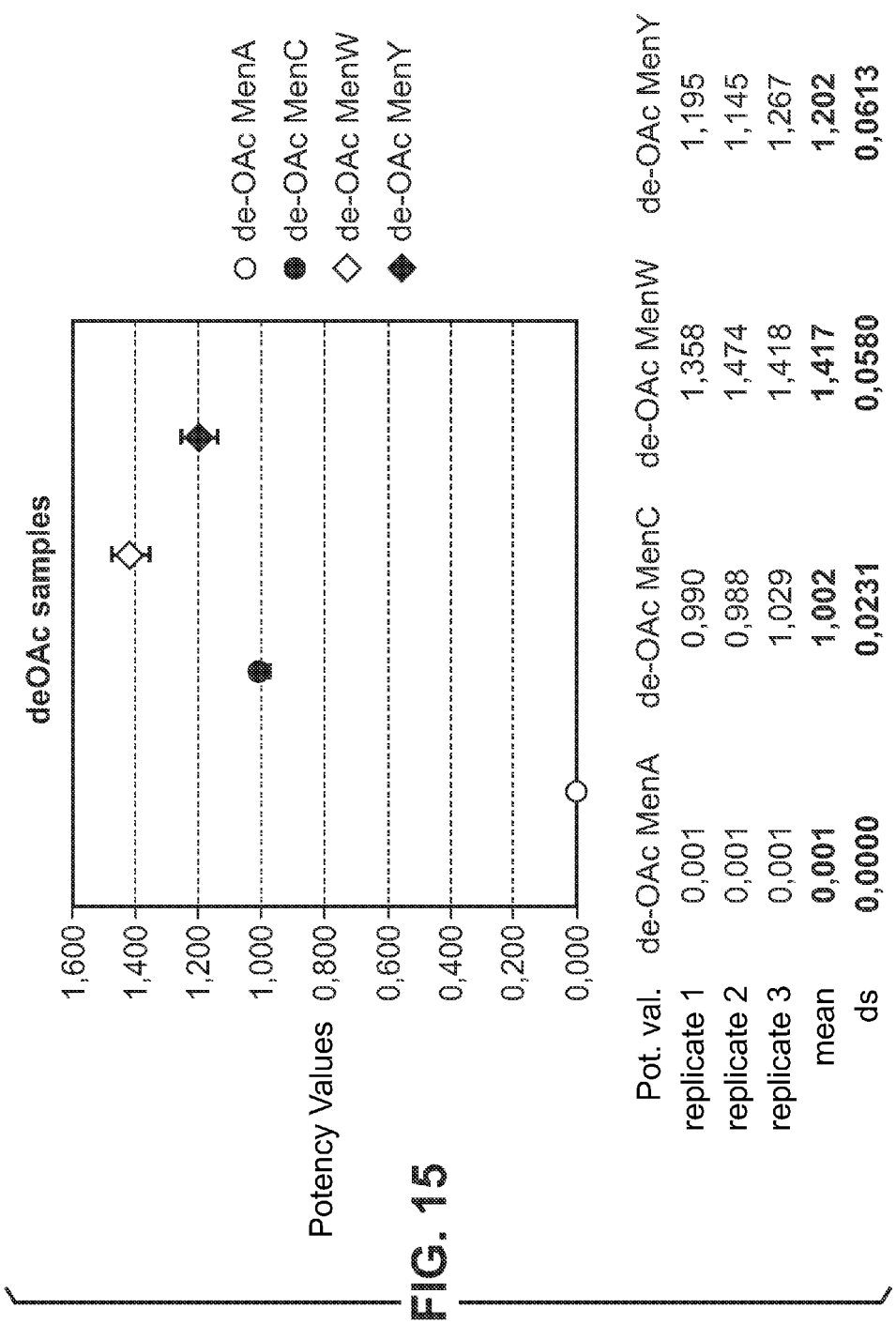
FIG. 15: Potency values of the three replicates for the MenA, MenC, MenW135 and MenY de-Oacetylated samples. The mean value and standard deviation are also shown.

Results of the drug product with the de-O-acetylated samples are shown in FIG. 15.

The relative potency evaluation was obtained by using a validated excel sheet. Potency values were calculated using the Parallel Line Method as described in the European Pharmacopoeia 6.0. According to this model, the relationship between the logarithmic transformation of the dose and the response (OD or a transformation) can be represented as a straight line, over the range of doses used; the model is based on the parallelism assumption between the unknown and the standard preparation. The horizontal distance between the two lines is the estimation of the potency of the unknown preparation relative to the standard.

In particular, after choosing the linear range of each curve, relative potency is calculated as:

$$RelativePotency = antilog\left(-\frac{Intercept_{SAM} - Intercept_{STD}}{b_{COM}}\right)$$

where:
bCOM is the common slope
InterceptSAM is the intercept of the Sample curve, assuming a common slope
InterceptSTD is the intercept of the Standard curve, assuming a common slope The acceptance criteria for the discrimination of invalid plates are:
R square of the Reference and test vaccine curves: >0.95
p-value for non-parallelism: >0.05

Discussion & Conclusion
Samples at Different Free Saccharide Content
MenA

All tested samples, added with increasing amounts of free saccharide, resulted in invalid plates ($R^2$ and/or p-value for non parallelism were not met) with the exception of two replicates for the sample added with 10% free saccharide.

Figure 11:
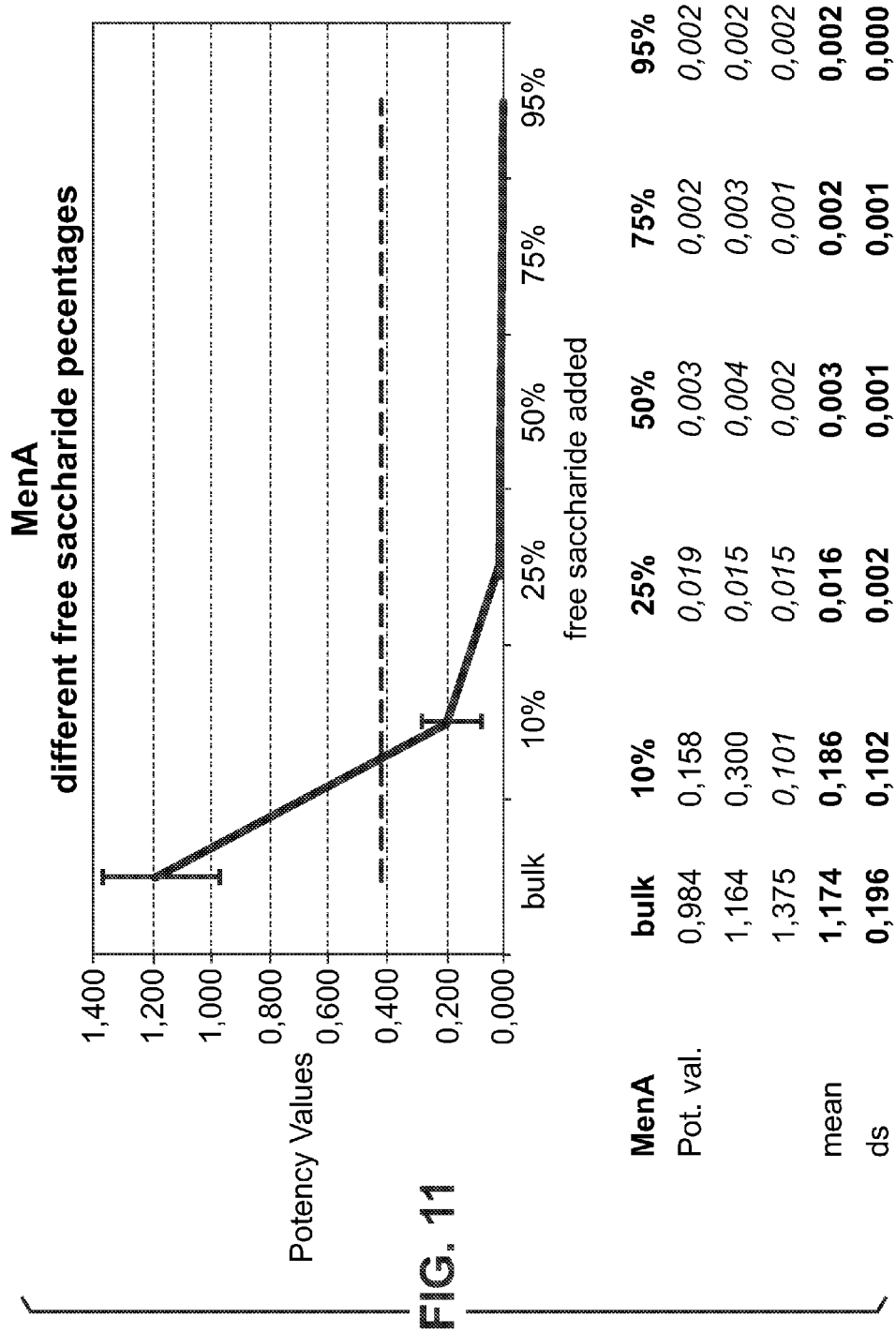
FIG. 11: Potency values of the three replicates for each different sample (monovalent MenA-$CRM_{197}$ bulk Lot GFB001A added with different free saccharide % combined with MenC-$CRM_{197}$, MenW135-$CRM_{197}$ and MenY-$CRM_{197}$ monovalent bulks) for MenA antigen. The mean value, standard deviation and lower cut off value are also shown. Values in italics indicate invalid plates.
Figure 12:
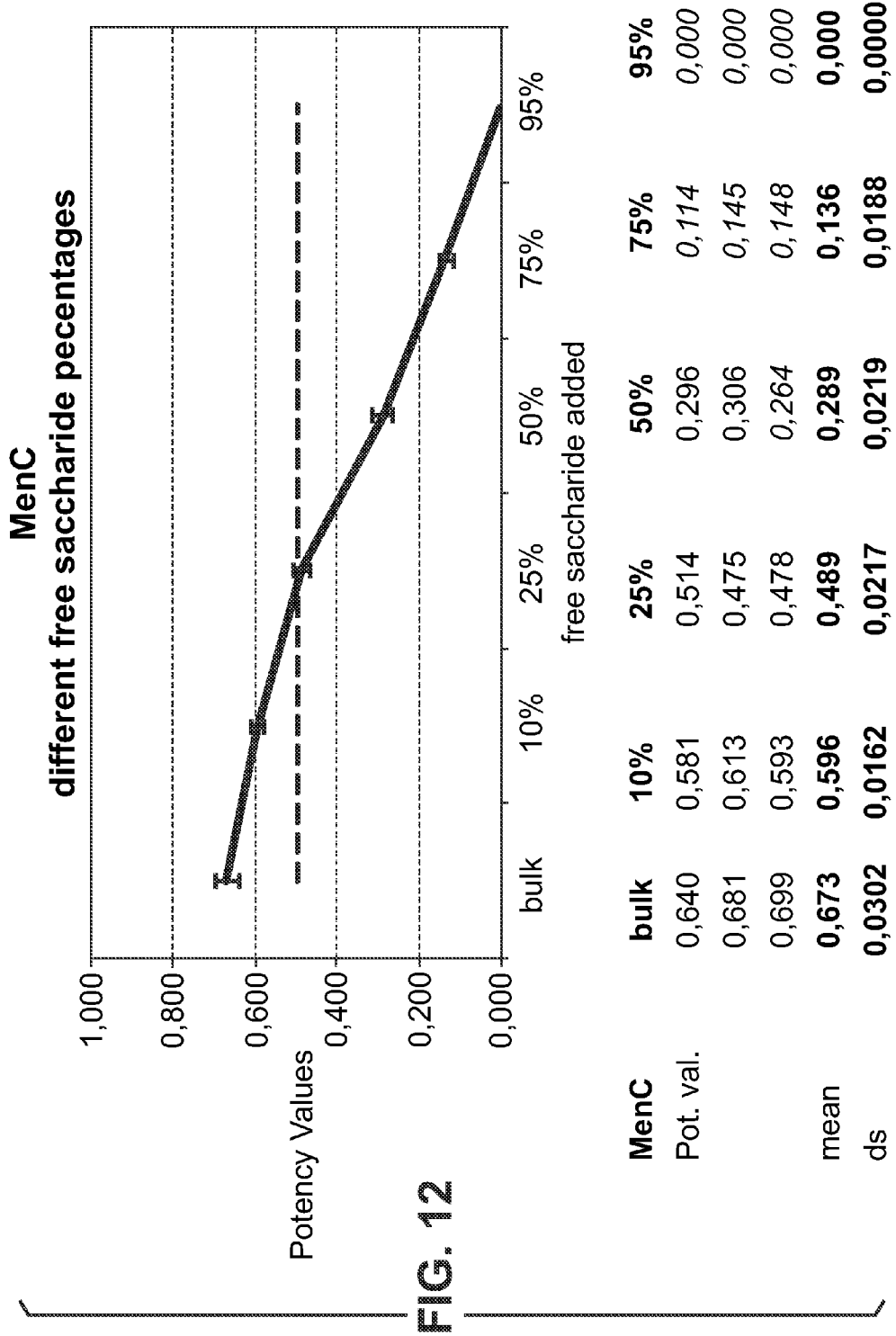
FIG. 12: Potency values of the three replicates for each different sample (monovalent MenC-$CRM_{197}$ bulk Lot TRMENC01 added with different free saccharide % combined with MenA-$CRM_{197}$, MenW135-$CRM_{197}$ and MenY-$CRM_{197}$ monovalent bulks) for MenC antigen. The mean value, standard deviation and lower cut off value are also shown. Values in italics indicate invalid plates.

Obtained results indicate that this in vitro immunogenicity and potency test discriminates between the Reference lot and samples with an increased content of free saccharide with respect to set specifications (addition of 10% to 95%) (see FIG. 11 and Table 21; release specification for the free saccharide content in the final drug product<10%, bulk free saccharide content<4.6%, lower cut-off potency value=0.421).

MenC

One sample with a free saccharide addition of 50% and all samples with 75% and 95% free saccharide added (bulk free saccharide content<1%) gave invalid plates ($R^2$ and/or p-value for non parallelism were not met).

Mean potency values for the samples added with 25% and 50% free saccharide were in the range 0.289-0.489, below the lower cut-off limit (0.495). Accordingly to the release specifications (free saccharide content<17%), the sample with 10% free saccharide added showed a mean relative potency of 0.596 (FIG. 5), in the acceptance range above the cut-off value of 0.495.

Obtained results indicate that this in vitro immunogenicity and potency test discriminates between the Reference lot and samples with an added content of free saccharide, from 25% to 95%.

MenW135

The samples containing 95% free saccharide gave invalid plates ($R^2$ and/or p-value for non parallelism were not met).

Figure 13:
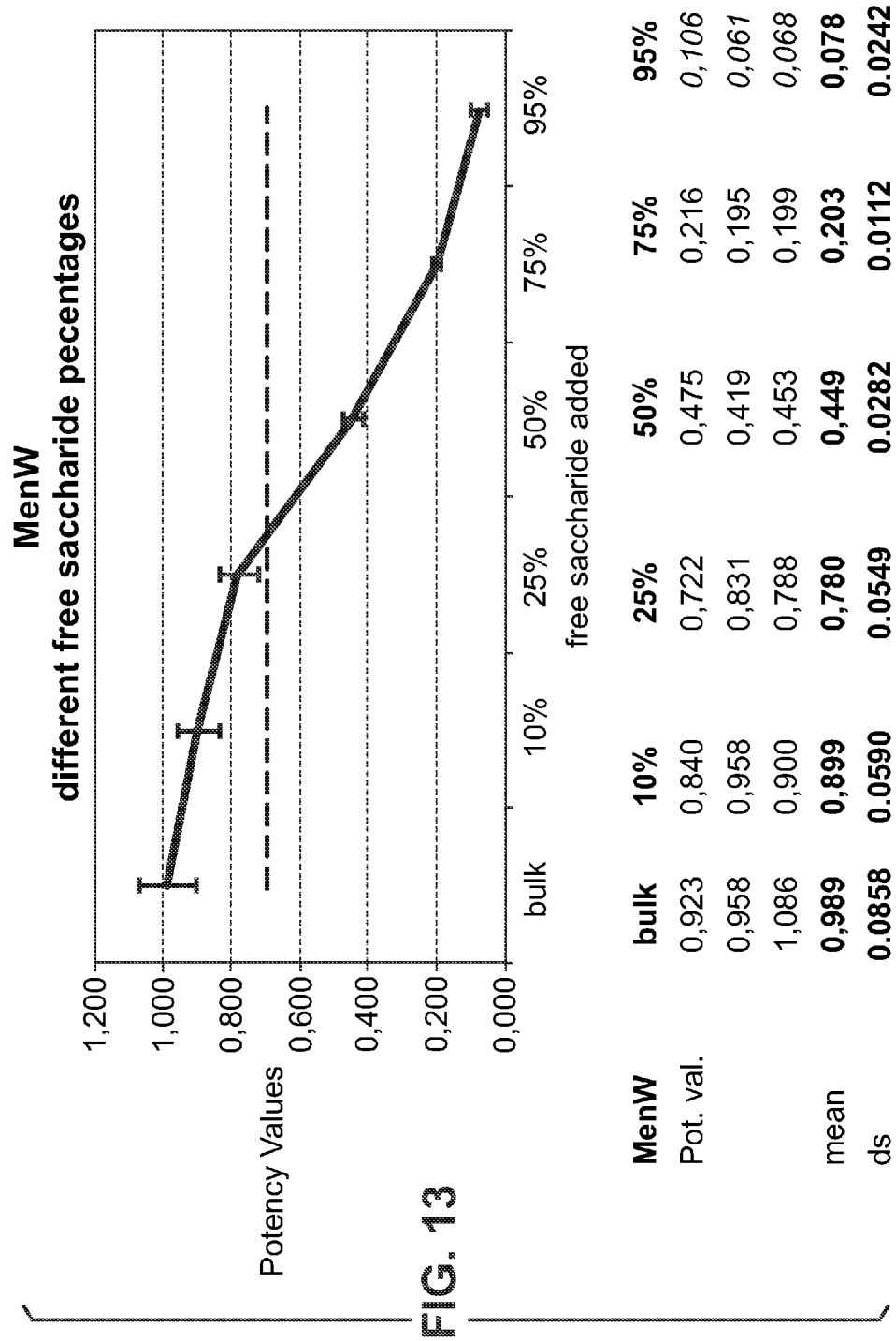
FIG. 13: Potency values of the three replicates for each different sample (monovalent MenW135-$CRM_{197}$ bulk Lot GFB007W added with different free saccharide % combined with MenA-$CRM_{197}$, MenC-$CRM_{197}$ and MenY-$CRM_{197}$ monovalent bulks) for MenW135 antigen. The mean value, standard deviation and lower cut off value are also shown. Values in italics indicate invalid plates.
Figure 14:
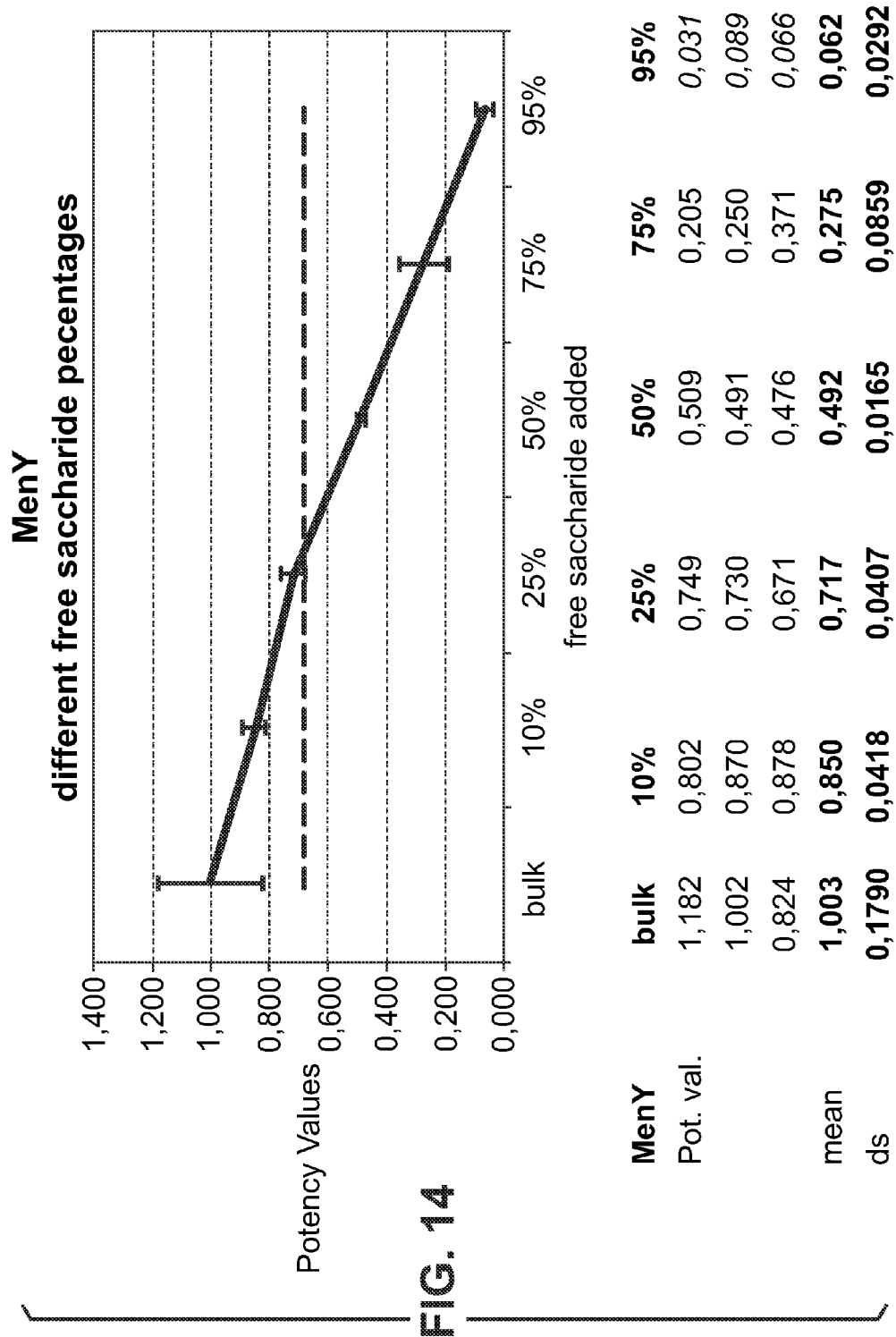
FIG. 14: Potency values of the three replicates for each different sample (monovalent MenY-$CRM_{197}$ bulk Lot GFB008Y added with different free saccharide % combined with MenA-$CRM_{197}$, MenC-$CRM_{197}$ and Men W135-$CRM_{197}$ monovalent bulks) for MenY antigen. The mean value, standard deviation and lower cut off value are also shown. Values in italics indicate invalid plates.

Obtained results showed a decreasing trend of potency values in the range of 10% to 95% free saccharide added (FIG. 13). Samples with 10% and 25% free saccharide added showed mean relative potency values above the lower cut-off limit of 0.690 (0.899 and 0.780 respectively).

These results indicate that the antigenic properties of these altered samples are maintained acceptable with the current immunogenicity and potency specifications up to 25% free saccharide added, even if they are out of the release specification for the free saccharide content (<17%).

MenY

The samples containing 95% free saccharide gave invalid plates ($R^2$ and/or p-value for non parallelism were not met).

Similarly to MenW135 antigen, determined potency values showed a decreasing trend in the range of 10% to 95% (FIG. 7) and samples with 10% and 25% free saccharide added revealed a mean relative potency value above the lower cut-off value of 0.679 (0.850 and 0.717 respectively).

These results indicate that, as observed for MenW135, the antigenic properties of these altered samples are maintained acceptable with the current immunogenicity and potency specifications up to 25% free saccharide added, even if they are out of the release specification limit for the free saccharide content (<17%).

De-O-acetylated samples

De-O-acetylated MenA sample resulted in potency values close to 0, showing a relevant difference in antigenic properties compared to the reference vaccine, thus confirming the well known importance of the molecule acetylation status in generating a bactericidal, protective immune response (FIG. 15) (Berry D S, et al. 2002, IAI 70:3707-3713).

No evident differences in potency values were detected for de-O-acetylated MenC, MenW135 and MenY samples with respect to the reference Menveo vaccine (potency value ~1), indicating that, for these serogroups, the functional epitope detected by monoclonal antibodies is not affect by the acetylation status of the polysaccharide.

Also this result is in line with published literature which indicates that the O-acetyl group is not relevant for protection in serogroups C, W135 and Y (Gudlavalleti S K, et al. 2007, Vaccine 25: 7972-7980).

REFERENCES

Berry D S, Lynn F, Lee C H, Frasch C E, Bash M C.: Effect of O acetylation of *Neisseria meningitidis* serogroup A capsular polysaccharide on development of functional immune responses; Infection and Immunity, 2002, 70(7), 3707-13.

Gudlavalleti S K, Lee C H, Norris S E, Paul-Satyaseela M, Vann W F, Frasch C E. Comparison of *Neisseria meningitidis* serogroup W135 polysaccharide-tetanus toxoid conjugate vaccines made by periodate activation of O-acetylated, non-O-acetylated and chemically de-O-acetylated polysaccharide. Vaccine, 25(46), 7972-7980 (2007).

Fusco P C, Farley E K, Huang C H, Moore S, Michon F. Protective meningococcal capsular polysaccharide epitopes and the role of O acetylation. Clin Vaccine Immunol, 14(5), 577-584 (2007).

What we claim is:

1. A method of assessing potency of a batch of a meningococcal capsular saccharide vaccine comprising:
(a) contacting in vitro a sample of the batch of the meningococcal capsular saccharide vaccine or a control saccharide mixed with the sample, with a bactericidal antibody;
(b) assessing the potency of the batch of the meningococcal capsular saccharide vaccine by measuring the binding of the bactericidal antibody to the meningococcal capsular saccharide vaccine or to the control saccharide; and
(c) releasing the batch of the meningococcal capsular saccharide vaccine if the potency meets a regulatory potency requirement(s) for release,
wherein the meningococcal capsular saccharide vaccine comprises at least two saccharides selected from (i) an *N. meningitidis* serogroup A capsular saccharide, (ii) an *N. meningitidis* serogroup C capsular saccharide, (iii) an *N. meningitidis* serogroup W135 capsular saccharide, and (iv) an *N. meningitidis* serogroup Y capsular saccharide, and wherein the bactericidal antibody binds to one of the at least two saccharides or to the control saccharide.

2. The method of claim 1, wherein the regulatory potency requirement(s) for release comprise a minimum potency requirement and a measurement reliability requirement determined by a regulatory agency.

3. The method of claim 2, wherein the measurement reliability requirement is a coefficient of variation of the measurements being less than a maximum value.

4. The method of claim 3, wherein the maximum value is a coefficient of variation of repeatability (all antigens) of 15%.

5. The method of claim 1, wherein the regulatory potency requirement(s) for release are as determined by the U.S. Food and Drug Administration or the European Medicines Agency.

6. The method of claim 1, wherein the at least two saccharides are (i) and (ii).

7. The method of claim 1, wherein the at least two saccharides are (ii) and (iv).

8. The method of claim 1, wherein the meningococcal capsular saccharide vaccine comprises all four saccharides (i)-(iv).

9. The method of claim 1, wherein the at least two saccharides are conjugated to a carrier protein.

10. The method of claim 1, wherein the control saccharide is mixed with the sample, the binding of the bactericidal antibody to the control saccharide is measured and the meningococcal capsular saccharide vaccine competes with the control saccharide for binding to the bactericidal antibody.

11. The method of claim 10, wherein the control saccharide is selected from the group consisting of: a native capsular polysaccharide from the same serogroup as one of the at least two saccharides, a capsular oligosaccharide from the same serogroup as one of the at least two saccharides, a synthetic saccharide, a conjugate of any of the preceding, or a combination of one or more of the preceding.

12. The method of claim 11 wherein the control saccharide is the native capsular polysaccharide.

13. The method of claim 11 wherein the control saccharide is the conjugate of the capsular oligosaccharide and the control saccharide is from one of serogroups A, Y, C, or W135.

14. The method of claim 10, wherein measuring the binding includes adding a secondary antibody that binds to the bactericidal antibody wherein the secondary antibody is conjugated to an enzyme that catalyzes a detectable reaction.

15. The method of claim 10, wherein measuring the binding includes serially diluting the meningococcal capsular saccharide vaccine.

16. The method of claim 15, wherein the serial dilution includes at least one, at least two, at least three, at least four, or at least five points in a linear portion of an inhibition curve calculated with measurements from the serial dilution.

17. The method of claim 16, wherein the potency is assessed by comparing the inhibition curve with a reference inhibition curve for a reference capsular saccharide of the same serogroup of known potency.

18. The method of claim 17, wherein the comparing is performed by taking the anti-natural log of the difference between the reference inhibition curve intercept for the reference capsular saccharide and the inhibition curve intercept for the meningococcal capsular saccharide vaccine divided by the common slope.

19. The method of claim 15, wherein the serial dilution is in a multiwell plate.

20. The method of claim 19, wherein the multiwell plate is a 96 well microtiter plate or a 384 well microtiter plate.

21. The method of claim 19, wherein the control saccharide is bound to a surface of at least one well of the multiwell plate.

22. The method of claim 15, wherein the serial dilution is a series of 2- or 3-fold dilutions if the control saccharide is from serogroups C, Y, or W135 or a series of 5-fold dilutions if the control saccharide is from serogroup A.

* * * * *